(12) United States Patent
O'Sullivan et al.

(10) Patent No.: US 7,960,505 B2
(45) Date of Patent: Jun. 14, 2011

(54) LANTIBIOTICS AND USES THEREOF

(75) Inventors: Daniel J. O'Sullivan, Plymouth, MN (US); Ju-Hoon Lee, Roseville, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 94 days.

(21) Appl. No.: 12/176,124

(22) Filed: Jul. 18, 2008

(65) Prior Publication Data

US 2009/0068121 A1 Mar. 12, 2009

Related U.S. Application Data

(60) Provisional application No. 60/961,374, filed on Jul. 20, 2007.

(51) Int. Cl.
*C07K 2/00* (2006.01)
*A61K 38/00* (2006.01)
(52) U.S. Cl. .................. 530/300; 530/324; 424/93.4
(58) Field of Classification Search .................. None
See application file for complete search history.

(56) References Cited

U.S. PATENT DOCUMENTS

| | | | |
|---|---|---|---|
| 5,260,271 | A | 11/1993 | Blackburn et al. |
| 5,691,301 | A | 11/1997 | Blackburn et al. |
| 6,746,672 | B2 | 6/2004 | O'Sullivan |
| 2002/0128186 | A1 | 9/2002 | Hillman |
| 2004/0191233 | A1 | 9/2004 | O'Sullivan |
| 2004/0192581 | A1 | 9/2004 | Walsh et al. |
| 2005/0250681 | A1 | 11/2005 | Molina |
| 2005/0250682 | A1 | 11/2005 | Molina |
| 2005/0266050 | A1 | 12/2005 | Smith et al. |
| 2006/0024414 | A1 | 2/2006 | Turek et al. |

OTHER PUBLICATIONS

Saleh et al 2004 ( Abstract only, 9th Egyptian conference for dairy science and technology, International Agriculture Centre, Cairo, Egypt, Oct. 9-11, 2004).*
Altermann et al., "GAMOLA: a new local solution for sequence annotation and analyzing draft and finished prokaryotic genomes," *OMICS*, 2003 Summer, 7(2):161-169.
Berger et al., "Similarity and differences in the *Lactobacillus acidophilus* group identified by polyphasic analysis and comparative genomics," *J. Bacteriol.*, Feb. 2007, 189(4):1311-1321. Available online Dec. 1, 2006.
Bowie et al., "Deciphering the message in protein sequences: tolerance to amino acid substitutions," *Science*, Mar. 16, 1900, 247(4948):1306-1310.
Fleischmann et al., "Whole-genome comparison of Mycobacterium tuberculosis clinical and laboratory strains," *J Bacteriol.*, Oct. 2002, 184(19):5479-5490.
Frank et al., "Oriloc: prediction of replication boundaries in unannotated bacterial chromosomes," *Bioinformatics*. Jun. 2000, 16(6):560-561.
Fukushima et al., "Effect of a probiotic formula on intestinal immunoglobulin A production in healthy children," *Int. J. Food Microbiol.*, Jun. 30, 1998, 42(1-2):39-44.
Garver et al., "Detection, identification and characterization of bacteriocin-producing lactic acid bacteria from retail food products," *Int. J. Food Microbiol.*, Sep. 1993, 19(4):241-258.
Gill et al., "Metagenomic analysis of the human distal gut microbiome," *Science*, Jun. 2, 2006, 312(5778):1355-1359.
Gostner et al, "Effect of isomalt consumption on faecal microflora and colonic metabolism in healthy volunteers," *Br. J. Nutr.*, Jan. 2006, 95(1):40-50.
Hopkins et al., "Age and disease related changes in intestinal bacterial populations assessed by cell culture, 16S rRNA abundance, and community cellular fatty acid profiles," *Gut.*, Feb. 2001, 48(2):198-205.
Ishibashi et al, "Bifidobacteria: their significance in human intestinal health," *Mal. J. Nutr.*, Sep. 1997, 3:149-159.
Islam, "Iron reversible inhibition by bifidobacteria and microbial diversity of the human intestine," M.S. thesis. University of Minnesota, Minneapolis, MN, Oct. 2005 cover date, 141 pgs. Publicly available Mar. 2006.
Kleerebezem et al., "Complete genome sequence of *Lactobacillus plantarum* WCFS1," *Proc. Natl. Acad. Sci. USA*, Feb. 18, 2003, 100(4):1990-1995. Available online Feb. 3, 2003.
Klijn et al., "Lessons from the genomes of bifidobacteria," *FEMS Microbiol Rev.*, Aug. 2005, 29(3):491-509. Available online Aug. 28, 2005.
Kuipers et al., Quorum sensing-controlled gene expression in lactic acid bacteria, *J. Biotechnol.*, 1998, 64:15-21.
Kullen et al., "Evaluation of using a short region of the recA gene for rapid and sensitive speciation of dominant bifidobacteria in the human large intestine," *FEMS Microbiol Lett.*, Sep. 15, 1997, 154(2):377-383.
Kunst et al., "The complete genome sequence of the gram-positive bacterium *Bacillus subtilis*," *Nature*, Nov. 20, 1997, 390(6657):249-256 and Table 1 (18 total pgs.).
Lane et al., "Rapid determination of 16S ribosomal RNA sequences for phylogenetic analyses," *Proc. Natl. Acad Sci. USA*, Oct. 1985, 82(20): 6955-6959.
Lee et al., "Sequence analysis of two cryptic plasmids from Bifidobacterium longum DJO10A and construction of a shuttle cloning vector," *Appl. Environ. Microbiol.*, Jan. 2006, 72(1):527-535.
Lee, "Comparative and functional genomic analysis of *Bifidobacterium longum*," Ph.D. thesis, University of Minnesota, Minneapolis, MN, Jun. 2007 cover date; 270 pgs. Publicly available online Jan. 6, 2008. Abstract available Sep. 13, 2007.
Lee et al., "Comparative genomic analysis of the gut bacterium *Bifidobacterium longum* reveals loci susceptible to deletion during pure culture growth," *BMC Genomics*, May 27, 2008, 9:247; article and additional files 1-13, 29 pgs. total.
Mackiewicz et al., "Where does bacterial replication start? Rules for predicting the oriC region," *Nucleic Acids Res.*, Jul. 16, 2004, 32(13):3781-3791.

(Continued)

*Primary Examiner* — Larry R Helms
*Assistant Examiner* — Padma V Baskar
(74) *Attorney, Agent, or Firm* — Mueting Raasch & Gebhardt, P.A.

(57) ABSTRACT

The present invention provides isolated lantibiotics that inhibit Gram negative and Gram positive microbes. The lantibiotic includes an amino acid sequence, wherein the amino acid sequence of the compound and the amino acid sequence of SEQ ID NO:21 or SEQ ID NO:22 have at least 80% identity. The lantibiotics have the characteristic of inhibiting growth of a Gram negative microbe in conditions that do not damage the outer membrane of the Gram negative microbe. The present invention also provides methods for making and using the lantibiotics.

13 Claims, 21 Drawing Sheets

OTHER PUBLICATIONS

Makarova et al., "Comparative genomics of the lactic acid bacteria," *Proc. Natl. Acad. Sci. USA*, Oct. 17, 2006, 103(42):15611-15616. Available online Oct. 9, 2006.

McInerney, "GCUA: general codon usage analysis," *Bioinformatics*, 1998,14(4):372-373.

Min et al., "Transfer RNA-dependent amino acid biosynthesis: an essential route to asparagine formation," *Proc. Natl. Acad. Sci. USA*, Mar. 5, 2002, 99(5):2678-2683.

Mitsuoka et al., "[The fecal flora in man. I. Composition of the fecal flora of different age groups]" [German-language article, English-language abstract], *Zentralbl Bakteriol [Orig A]*, Mar. 1973, 223(2):333-342.

Molenaar et al., "Exploring *Lactobacillus plantarum* genome diversity by using microarrays," *J. Bacteriol.*, Sep. 2005, 187(17):6119-6127.

Mota-Meira et al., "MICs of mutacin B-Ny266, nisin A, vancomycin, and oxacillin against bacterial pathogens," *Antimicrob. Agents Chemother.*, Jan. 2000, 44(1): 24-29.

Muñoa et al., "Selective medium for isolation and enumeration of Bifidobacterium spp," *Appl. Environ. Microbiol.*, Jul. 1988, 54(7):1715-1718.

Nei et al., "Simple methods for estimating the numbers of synonymous and nonsynonymous nucleotide substitutions," *Mol. Biol. Evol.*, Sep. 1986, 3(5):418-426.

Nes et al., "Exploration of antimicrobial potential in LAB by genomics," *Curr. Opin. Biotechnol.*, Apr. 2004, 15(2):100-104.

Nilsson et al., "Bacterial genome size reduction by experimental evolution," *Proc. Natl. Acad. Sci. USA*, Aug. 23, 2005, 102(34):12112-12116. Available online Aug. 12, 2005.

Olasz et al., "Target specificity of insertion element IS30," *Mol. Microbiol.*, May 1998, 28(4):691-704.

O'Sullivan, "Primary Sources of Probiotic Cultures," in *Probiotics in food safety and human health*, Goktepe et al. eds., CRC Press, Boca Raton, FL, 2006, pp. 91-107.

O'Sullivan, "Evolutionary Adaptation Responses in Bifidobacteria: Comparative and Functional Genomics," 2nd International Symposium on Propionibacteria and Bifidobacteria: Dairy and Probiotic Applications, Wadahl, Norway, Jun. 5-8, 2007, abstract (2 pgs.) and presentation (38 pgs.); 40 pgs.

O'Sullivan, "Evaluation of a Novel Bacteriocin for Extending the Shelf-Life of Dairy Products," Midwest Dairy Foods Research Center annual meeting, St. Paul, MN, Jul. 20, 2007, abstract (2 pgs.) and presentation (17 pgs.); 19 pgs.

Price et al., "A possible role for DNA restriction in bacterial evolution," *Microbiol. Sci.*, Oct. 1986, 3(10):296-299.

Pridmore et al., "The genome sequence of the probiotic intestinal bacterium *Lactobacillus johnsonii* NCC 533," *Proc. Natl. Acad. Sci. USA*, Feb. 24 2004, 101(8):2512-2517.

Ratnaike, "Acute and chronic arsenic toxicity," *Postgrad. Med. J.*, Jul. 2003, 79(933):391-396.

Ross et al., "Isolation and characterization of the lantibiotic salivaricin A and its structural gene salA from *Streptococcus salivarius* 20P3," *Appl. Environ. Microbiol.*, Jul. 1993, 59(7):2014-2021.

Sambrook et al., *Molecular Cloning: A Laboratory Manual*, Books 1-3, Cold Spring Harbor Laboratory Press, Cold Spring Harbor, NY, 1989; title page, publisher's page and table of contents only, 31 pgs.

Schell et al., "The genome sequence of Bifidobacterium longum reflects its adaptation to the human gastrointestinal tract," *Proc. Natl. Acad. Sci. USA*, Oct. 29, 2002, 99(22):14422-14427. Available online Oct. 15, 2002.

Servin, "Antagonistic activities of *lactobacilli* and bifidobacteria against microbial pathogens," *FEMS Microbiol. Rev.*, Oct. 2004, 28(4):405-440. Available online Feb. 21, 2004.

Skouloubris et al., "A noncognate aminoacyl-tRNA synthetase that may resolve a missing link in protein evolution," *Proc. Natl. Acad. Sci. USA*, Sep. 30, 2003, 100(20):11297-11302. Available online Sep. 17, 2003.

Slesarev et al., "The complete genome of hyperthermophile Methanopyrus kandleri AV19 and monophyly of archaeal methanogens," *Proc. Natl. Acad. Sci. USA*, Apr. 2, 2002, 99(7):4644-4649.

Sofia et al., "Analysis of the *Escherichia coli* genome. V. DNA sequence of the region from 76.0 to 81.5 minutes," *Nucleic Acids Res.*, Jul. 11, 1994, 22(13):2576-2586.

Su et al, "Detection and quantification of *Bifidobacterium lactis* LAFTI B94 in human faecal samples from a consumption trial," *FEMS Microbiol. Lett.*, Mar. 1, 2005, 244(1):99-103. Available online Jan. 21, 2005.

Tatusov et al., "The COG database: a tool for genome-scale analysis of protein functions and evolution," *Nucleic Acids Res.*, Jan. 1, 2000, 28(1):33-36.

Tatusova et al., "BLAST 2 Sequences, a new tool for comparing protein and nucleotide sequences," *FEMS Microbiol. Lett.*, May 15, 1999, 174(2):247-250.

van Kraaij et al., "Lantibiotics: biosynthesis, mode of action and applications," *Nat. Prod. Rep.*, Oct. 1999, 16(5):575-587.

van Kranenburg et al, "Functional analysis of three plasmids from *Lactobacillus plantarum*," *Appl. Environ. Microbiol.*, Mar. 2005, 71(3):1223-1230.

Ventura et al, "Prophage-like elements in bifidobacteria: insights from genomics, transcription, integration, distribution, and phylogenetic analysis," *Appl. Environ. Microbiol.*, Dec. 2005, 71(12):8692-8705.

Wescombe et al., "Purification and characterization of streptin, a type A1 lantibiotic produced by *Streptococcus pyogenes*," *Appl. Environ. Microbiol.*, May 2003, 69(5):2737-2747.

Xie et al., "Lacticin 481: in vitro reconstitution of lantibiotic synthetase activity," *Science*, Jan. 30, 2004, 303(5658):679-681.

Xu et al., "A genomic view of the human-Bacteroides thetaiotaomicron symbiosis," *Science*, Mar. 28, 2003, 299(5615):2074-2076.

Yoshioka et al., "Development and differences of intestinal flora in the neonatal period in breast-fed and bottle-fed infants," *Pediatrics*, Sep. 1983, 72(3):317-321.

Zawilak et al., "Identification of a putative chromosomal replication origin from Helicobacter pylori and its interaction with the initiator protein DnaA," *Nucleic Acids Res.*, Jun. 1, 2001, 29(11):2251-2259.

Rollema et al., "Improvement of Solubility and Stability of the Antimicrobial Peptide Nisin by Protein Engineering," *App. Environ. Microbiol.*, Aug. 1995;61(8):2873-2378.

\* cited by examiner

Fig. 1
A
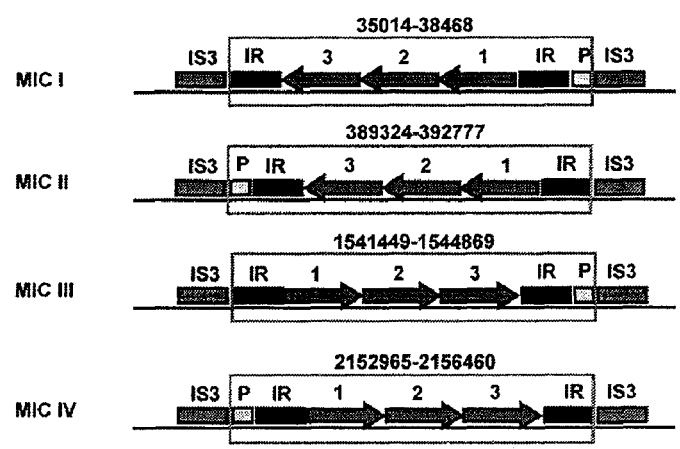
B
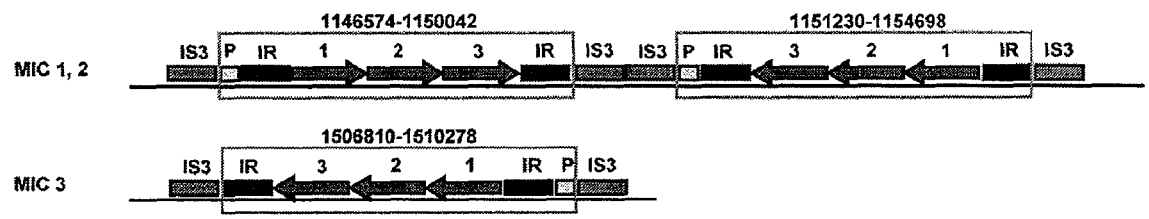

Fig. 5
A
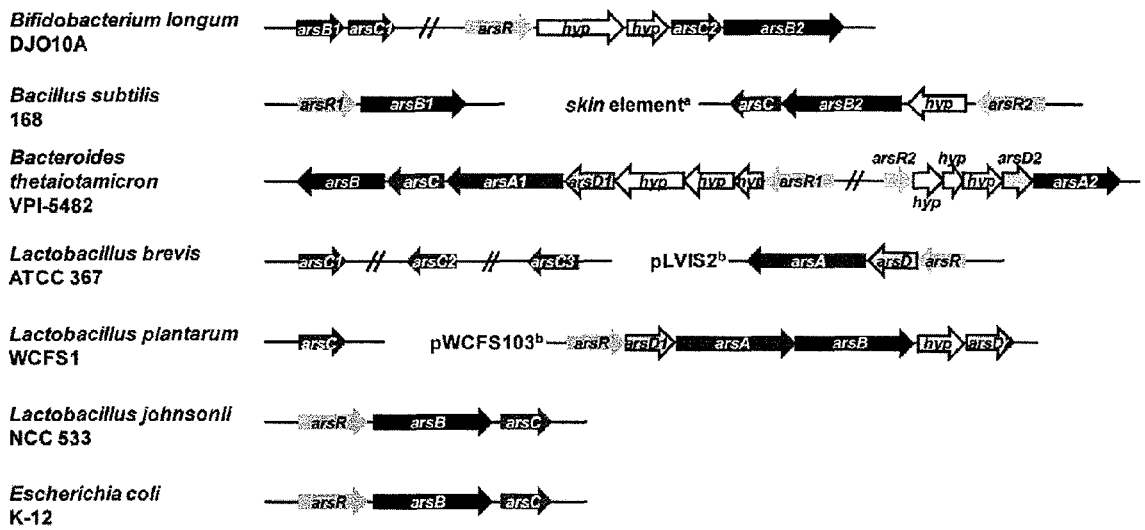
B
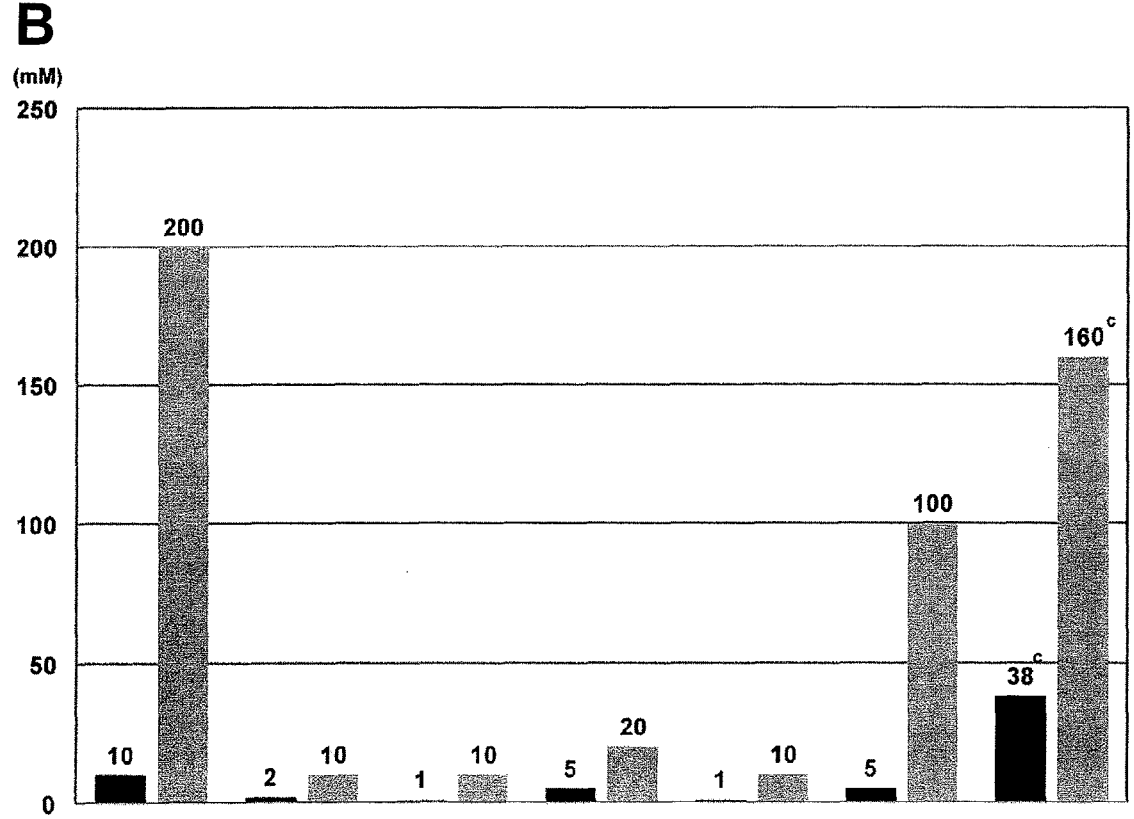

Fig. 9

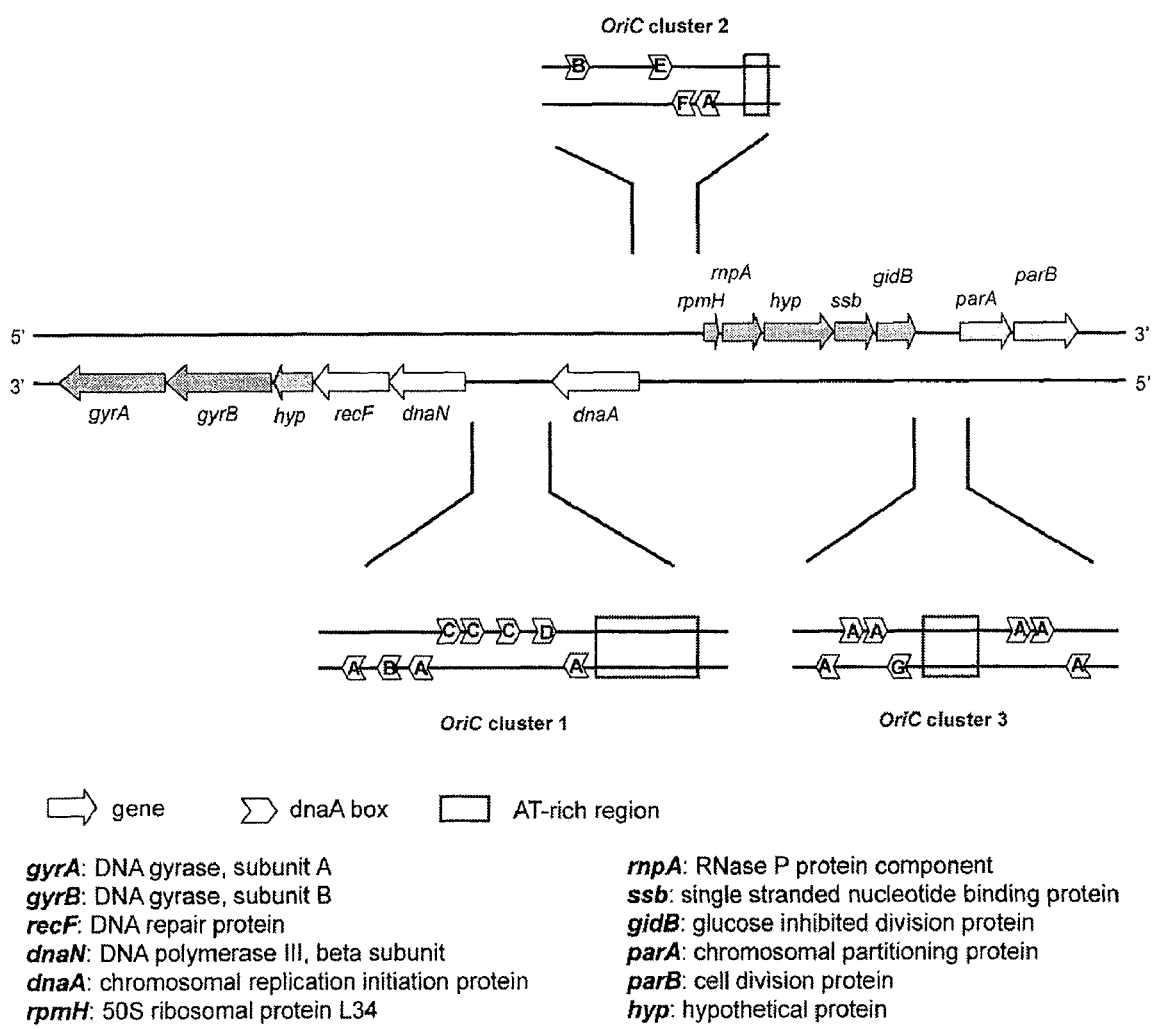

→ gene    ▷ dnaA box    ☐ AT-rich region gyrA: DNA gyrase, subunit A
gyrB: DNA gyrase, subunit B
recF: DNA repair protein
dnaN: DNA polymerase III, beta subunit
dnaA: chromosomal replication initiation protein
rpmH: 50S ribosomal protein L34 rnpA: RNase P protein component
ssb: single stranded nucleotide binding protein
gidB: glucose inhibited division protein
parA: chromosomal partitioning protein
parB: cell division protein
hyp: hypothetical protein Fig. 14
A
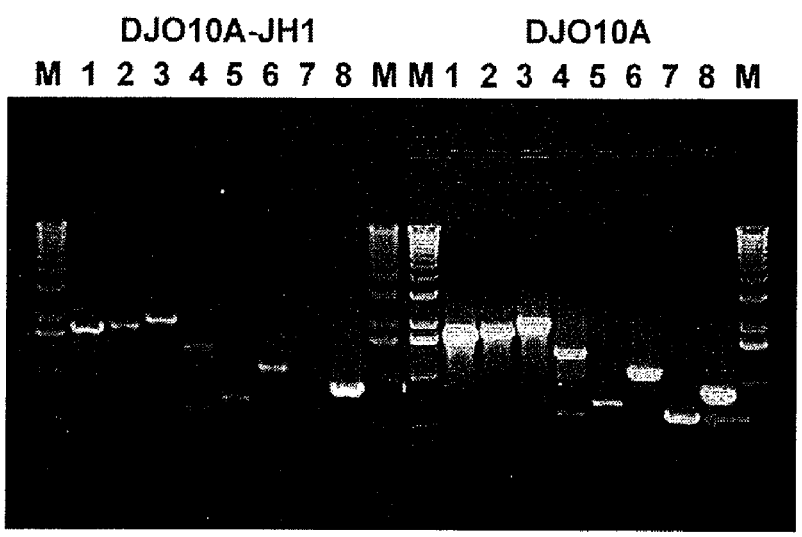
B
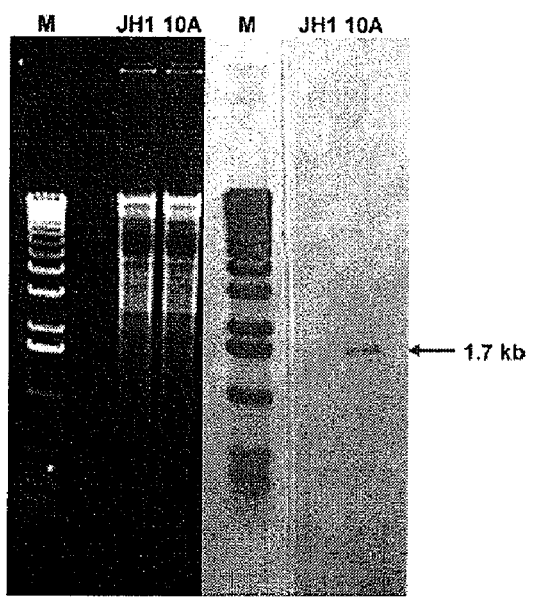

Fig. 16

SEQ ID NO:23

```
1978650                                       c tactccaact tgacaaaaca cagcggtagc
1978681 gcctgcgcgg ttcggcgcgc ctgcggccgg ccttgcgccg cggcggggcc ggcgatgtag
1978741 tatccgcccg tccacgggcc cgtcttcagc cgtttcggcc ggtacggccg gtaggactcg
1978801 ttctcgttgg acgggaacca cgtgtcgcgt ttgatctccc tgccgaccgt cgaggcgttg
1978861 cggccgagca tcagaccgat cctgcggatg ctggtgccgt tgccgatctc gatctggatg
1978921 acctggcgtt cctcttccga caggtgcgaa catgcttctc ccataggtgc aacatcoctt
1978981 cggactggtt atccggacaa tctccaatcc aacgggtgtt gcactttcaa ttagacaacg
1979041 gggcgggcat gttcgtacga aaaacgtcta tcatgtgcgc tatggggaat ccaaatgaaa
1979101 tcagactggc gatagtcgat aacgacgact tcgtgctgat gggtttggca gcgttcttgt
1979161 cgcgtcatct gccgaatgtt cggttagctt ggaaggcgaa taccggaacc gatgctctgg
1979221 aatatgcgac ggatcccgca aatgaagcgg acattctgct ggttgacatg agtctggagg
1979281 acatgcccgg agacatggtg tgccgggaaa tcagaagtcg taacaggatg ttgccgttgc
1979341 tggcggtgac atcgttcagt ttaattcgct atgcgcgacg tgctgctgag ggtggtgctc
1979401 aaggcattgt gtcaaaagct gattttccag cactgtgtaa agcggtcaag ctcgtcagcg
1979461 atggtcatac tctctgtgtt cgagtaggag gggagactat tggattcgag gatgtagatg
1979521 ctgcatatca tcgtctggtt cgacttcccg tgaatagaat cgaaagattg tcggaacggg
1979581 aaaaatatgc catggaacta tattcacagt cgtataagcc cactcagatt gcccggatga
1979641 tggatgtttc ggcagggacg gtgaaaacct atcttgaccg tgttcagaac aaactccatc
1979701 ttacttccag agcccaactg attgcctatt ggtggaggcg gaacgatgg tgagacgatt
1979761 ggcaatggaa acgatactg tggttcgcaa gaaatgcttg ggagtatcga aaaaaaatct
1979821 tgttctatcg atagtggcca tgacatgtct tgccgcatgt atcgccgaat ggattcttga
1979881 ttctcctgag agtttgaatg atgggtttat tcgcatcgtg tacatgcttg ctgtgagtat
1979941 gttgccgtta tatccggtac cggcaacatg ggggattatc gtcatcgcat ttctgaatga
1980001 attgatgcct tgcttatcgc aatgcgatga gtcatggggt gttctggtgt ctcttgcgat
1980061 tcaaggctat gctgctgttt ggtggaatgg tgtgacggca acggtgctgt tgtctattag
1980121 cgctttgctg aattatgcga tatatcggga gaatagtgaa tttggttcgt tcgatggttc
1980181 cattaatttg gtggtgttgc tttggtttgt gtttctttta ggggtttggc tacggcaaag
1980241 gaacagactt gaaaagaaaa aagagttaga aagaaagct gaaattgttc gatataactt
1980301 acagcttgct gagggatgc atgatgccat gtctggtgag ttgacacgaa tgttggtcat
1980361 agtgcaggaa ggtatcgatg catcgaagga agaagagctt aagcgatgga gaaaattgca
1980421 gaacggtatc aataaggtat tccaagatct gcattcggtt atgaattatc tatcggatga
1980481 tgaccataaa caagatgagg tatttcatgt aagtcttgcc gaacatattc aagctacatt
1980541 gactgaaagt gaccgtcggt tgcatgacaa agggttttgc ggtcattcat ctcttcgcgg
1980601 tgtatccagc gcaatgttga actcgtggaa tcaaataatc gttaacctgt tgcgtgaaat
1980661 ttacacgaat attgaacgct atgctgacaa aagtgaatat tccgtcattg tcacattttc
1980721 aaataatgct gttgatattg ttcaggtgaa taatgtcga caaaagagtc ggcgatgtgt
1980781 gactttggga gcaagaaaag ggctaagtat atattcccgt ttgatatctg acaaggagg
1980841 attcatcaga tatgaaaaag acggcgaaga atggtctttc tattgcatgt taccgctact
1980901 gacctaattt ctgatatggc ataatggaaa ccatacaggg catagtgaat atgttgatat
1980961 ttcttcctcc gttgaactgt tgcttggagt gctggctgac gctccgaatg tcaaaccaag
1981021 taccgtaagt attaaagcg gtgttctcat gagggttcct ttgcgtcggg gtgtgtcaat
1981081 gatcattgca caacatggat tcatataaaa gtccttgtcc cctaatggca tacaagtcat
1981141 tgcgaagcgg gagaaagcgc gtcatgctta cagtagctct tcgcctgaag gcaggaatt
1981201 aggtaaggag gcctatatga gcatcaatga gaagtccatt gtcggtgaat ccttcgagga
1981261 tctgtcggcg gccgatatgg cgatgctgac cggtcgcaac gatgatggcg tcgcgccggc
1981321 gtcgctgtcg ttcgcggttt ccgttctgag cgtgtctttc tcggcatgtt cggtaacgt
1981381 cgtcacccga cttgcatcct gtgggaactg caagtgaacg ttgctttaca tgggtcaggt
1981441 atggattgcg taaaacatcc gacccatacc tgacacttgt tatcgttaag gggaagtggc
1981501 atgaaggcga ttctgtttcg tgactgcaag gcatgttcc agtcattcaa gaactggggt
1981561 atggttctta tcattatggt cacggcaata ttcgtggaga tggttccag tggcgcaggc
1981621 attctagacc catttacttg ggctgtcttt tttggaccgt ttttcatcta ttcgtcatgc
1981681 tcggtgatgg tctccatcct gtatcaggat ttccgagatg gactgtttga gctctatata
```

Fig. 16 (continued)

```
1981741 cagtctggtc gttcctattg gagctactgc tggtgtaagt gcctgtttcc tgttatcctg
1981801 acagtgattt ccgtgctttt gaatctggct tttatgcgtg ttttgtcatc aggctttcag
1981861 ataaccgctg gagcagatga tgcaattggt gctcttatcg tatcagtctt aggaacaatc
1981921 gtctgttctt tgggcgcaat gccgatggtt tatgtctccc ggaacagcga tccgacaatg
1981981 gcacaactgg ttttggtgtt gattgcgatc ctgctccaat ggcatatac gcttgtggtc
1982041 gtcaacgtga tgccgctgtg cctgttctcg gtcggttatg tcgtattggt agtggtcgcc
1982101 atcggtattt caaccggagt attctctcga tattttatca acaccaatat cgagctgtga
1982161 catctactgg attcgaagct tttggaaagg tggattttcca tgaccagcat ggtggcctat
1982221 gtcgcttcgc gtaatccgca gtcgcagacg ttgcggtcgg ttcgtctgat acaggatgcg
1982281 gtcagtggga acattgacgc ggaatggacg attctgacgc cgaatgacac gacgatcttg
1982341 ccgtcggatg gtactgcgag cgagttttcc accggtgtcg atcatatcga gctgaacgga
1982401 ctggacgatt ccgcccggt caaaaaagca atcgaacgat gcgattatct gattctcggt
1982461 tcgccgacct atggccataa cgtttccggc gacatgaaga ttctgatgga tcgactcacc
1982521 tattggggc atttgttcca tctggcggc aaaccgggca tggcaatggt cagcgccaca
1982581 accaacgggt tccttgaagt cggcgaactg atggaacggt tcatggaatc actgggcatc
1982641 atcattgatg aaaccgcata ccacaccact tttacgccat tcgatgaggc aatggccgat
1982701 cagaccgccg cggccatcgt gcgggcgctg aacacactgc gggatggcgt cgtgcctgaa
1982761 accagcgaaa ggcaggagct ggcattccaa tcctacaagc gtgactacgc ccgacgagac
1982821 ggtagcgatg cagaatcgcg gtattggcgg gaacgcggca tgttcgactg tgcgacgttc
1982881 catgaatacg tcgaaacgcg gcggaagctg ccggaatccg tccacgccga acgtaggggg
1982941 gactttccat gaacggtaac gttggaacga cctgggcggc ttctgccacg acccttgagg
1983001 aacggtgcat ggcggcaacc gctatgccgg atgctttgcg acagtatcgg gcatcgcatg
1983061 cggaagacat gctttcggca acggtggaat ggaaaaaccg acggaaccca ctgcgggacg
1983121 aggactatca aggcatcgcc gacgcgctcg gcgatgacgc atccgtggtc gaaaccgtca
1983181 tcgcggatcg ggaacggaaa ctgagcggcc atgtcgagcc ggcatggtcc gttgaactgc
1983241 agacgattct gaaccgttac gacagcgagg aagagcgagt cgaacgcacg gggtatgcca
1983301 ccgccttcgc accgttcgtc gcgtacgtga agcggaact gcaagcgcat atgtcggcct
1983361 gttcattgcc gatgaatgac gagcgcctta tcgaacagtg cctgagcgca tacgtcgagc
1983421 gtctgttgag catcggattg aaaaccgtcg tatgggaatt gcatgtcgcg cgtcaggccg
1983481 gttcgttggg cgacggcgat gcgaagcgac aattgcggcg atatttcgaa ctgctggcca
1983541 ccgacgaata ccgtggccat atgtatgcga aatatccggt actgcttcgt tttgtcacgc
1983601 agacgacagt ccattacatc gatttcgtca aggaaatgct cgaccgcgta tccatggatc
1983661 gcgacgagct cgcctccttc gcaggcgtcg gcgatgattt caggttggaa gatatgtcca
1983721 tcgaccgtgg cgacgcgcac gacggtggaa gagccgtggc catgctcacc atcggcggac
1983781 ggaaaatcgt atacaagccg cgtgacctgc atatccatga gcttttcgcc ggattggtga
1983841 ggcgatgcga acggacgaag ggtttccttc cgatgcgagt gtcggacgtg ctgacgaaat
1983901 ccggctacgc ctatgaggaa tcgtggaac acggcacctg cgaggatgca cgtcaggtgg
1983961 agcgctatta caccagatac ggtcagctgc tcggattggt atggctcctg cacggcgacg
1984021 acatgcacca cgagaacatc atcgccagcg gggaatatcc gatggtcgtc gatttcgaga
1984081 cgatcgccac gaaccatgtg accatggaca tgcccgacgg caccgatgcc gacatccgcg
1984141 tatccacgat attgcgggat tcactggcat cctcctgtct gttgccggcg aaaacggcga
1984201 tgtcggccga cggtacatcc gtcgacatca gcgccttcga aaccggtgag cagacgatgc
1984261 ccggcatcgt cgcgtccccg gtgggattgg actccgccga tgcccattac gagaggaacg
1984321 ccgtgacgtt cagcaaggac ggctgcgcgg tgacattgga tgacgccgtt gtggatccgt
1984381 atcattacaa gcgacagatt ctccaaggat tccgcaatac ggtcgccgcg gcgatgacca
1984441 tcgacgcgga tgaatgggat gcgatgctgt ccggcgagga tacgaccgtg cgtgtgctgg
1984501 tgcgcaacac cagcgcctac gcccgatttg cggatttcat ccatcatccg tcggcgttga
1984561 aggacatgct ggacgtcgaa gccatactgg agaacctgta tgtctaccca ttccgtgaca
1984621 agcgcatctt cgcaagcgaa taccggcaga tgctcgccgg ggacatcccc atgttcaccg
1984681 cacagctgac gggacatgat ctgcacgctc ccgatgaac gaccattgac ggcgtctgcg
1984741 aacgttcggt acgcgaacgg gtgcttgaca ccatcgggca tcttgacgaa caggccgcat
1984801 tgcaatcgcg cattatccgc aacgccttgc gcatggaacc cggcatggag gacgcgcatc
1984861 cgacggcttc ggtgtcgtcg gacacggatg cggagcatta cccaatcgaa ctcggcacga
1984921 ggatagccga cacggccatc ctccaggaaa ccgatggcac cgtatcatgg cttacagcga
1984981 accgatccga caccatggcc gcggacaaga ccgtggatga acgtacgaa ccgggggcgc
1985041 cgacttcggg actctacgac ggcatggccg ggacgggcat gttcgccgcc gaactgtatc
1985101 ggcggacaca cgatgagcgc tggcgtgacc tgtgcacgcg tatgatgcgg agtctgatgc
```

Fig. 16 (continued)

```
1985161  gccgcaagga  cagaggcatt  acgtattccg  gcttcacttc  cggcctgtcg  cgaagctatt
1985221  gcgcgttacg  catggccaat  gccggcatca  cgtcgcccga  agctcgccgt  tgcatgacgc
1985281  agacggttcg  tatgctgccg  gcatacatcg  acgatatgct  gccgaagctc  ctgcagcgcg
1985341  acaatcctca  accgtcattc  catctggatt  acctgaccgg  ggcgggcagt  tcgatcatgc
1985401  tgtatctgcg  gctgtacgac  gtattccatg  acatgcgcat  agtggaacaa  accagccggc
1985461  tggggagaac  cgtcatccgt  gcgtttccg   aaacccagcg  gaacgccgac  gaatccgatg
1985521  acatgccgta  tccaaccggt  gccgcgcacg  gactggaagg  catggccgtg  gcgttctgga
1985581  agctctacgc  ggcgacgggg  aatcgcgaat  tcgccgaatt  cgcccgaatg  ctttggcgga
1985641  aatcggacgc  tcgaagaagc  ggtgcgaaac  aggaggacgc  cggcaaatgg  tgccgtggga
1985701  aggtcggcgt  gctctgggca  cgcaatgagc  tggcggccac  tgccggcgcg  gacggcgaac
1985761  gtttcttcga  ggatgaaaac  ggacgggcgt  tcccagacaa  ggcagatatc  acggcgttgc
1985821  ttgggaacgc  ggattgggac  gacgacggcg  tgtgccatgg  acgatgcggc  atgatcgaca
1985881  ccctgatatc  catcggcaat  gccaacggtg  acgaatggta  tcgcatgcag  gcacagcgtc
1985941  tgatggacga  catgatcgcg  caggcccgtt  cgtcgggacg  tttccggctg  aggcaatccc
1986001  gtgaattcgt  ggatctgtcg  tacttccaag  ggccggtcgg  cgtcgcctac  acgatgcttc
1986061  gtctgaacga  cccgtccacg  ccctccatac  tcgcactgga  aacgcgatga  cggacatgac
1986121  ggatacgaac  acaaccgaat  cgacgacaag  gaaagacaat  atgaccgccg  accacatcaa
1986181  ccacgccgac  cgcaccgaca  acggcgaaca  tgccatcatc  gccgtcgaac  acgtcacctt
1986241  cggctacaag  aagaaacaga  ccgtgttgga  ggacatcgac  ttcaccgtgc  cgcaaggcca
1986301  gtcgctggcg  atcctcggat  acaacggcgt  cggcaagacc  acgctgttca  gactcatcgt
1986361  cggactgctg  cgcccccgtg  aagggcgatg  cgtgatcgat  aggcgtcggg  tgccgtcgat
1986421  gcgcgacgtg  ttccagatga  ccgagaacgg  caatctcgtc  ggcacgatga  ccgtgcgtga
1986481  caacatccac  ttccggcaac  tgctgttccg  gtccggcaag  ggaatcgcgg  acggcggcca
1986541  taccgtcgac  tcgaaacggc  tggaggatga  gccgctcgtc  cgtgccttcg  aattggaggg
1986601  gcatctcgac  aagaaggtgg  cggaactctc  gaccggtctg  cgcaaacggg  tcggcatcgt
1986661  cgccggcatg  ctgttcgacc  gcatgtcat   catgctcgac  gagccaagca  acgccattga
1986721  tccgatcacc  cgctcgctgc  tcgtcgatta  cgtcaaccag  cttcgcgccg  acgagcgcac
1986781  tttgctcacc  gtcacccatg  acctcgaata  ctgttggaat  gtggccgacc  ggatcatcat
1986841  ccttgacgac  aaacacctcg  tcaaggatat  gatgctcgcc  gaattcgacg  actatgaggc
1986901  gttcaccaag  gcgtccacgc  tcgggcgtga  ccgcacgcac  gtcgacttcg  gccttcccgc
1986961  gcgcggacgg  caagcatgag  atcatggcgt  cgtcaccgtg  tcccgtttat  cgaacaaggc
1987021  gagcacagcg  aatgcgggct  ggccgccgca  gcgatgatcc  tcgccgcatt  cgggcatccc
1987081  gtgaccatgg  acgagctgcg  ccgccggtac  ggcgctccac  gcggcggact  gagcctcgcg
1987141  aacatcgtaa  cggtgctgtc  cgactccggc  atccgcgtac  gcgcggtcac  gaccccagc
1987201  gccgaagcgt  tgaaaaccgt  catgacgcca  tgcatcctgc  attgggacga  caaccatttc
1987261  gtcgtgctcg  accattacgc  atacggccga  ttccgcatcg  ctgacccggc  gaacgggcgc
1987321  catgcctata  cgcccggcga  actcgcggcc  cactgttctg  gcgcggtgct  gattccgcaa
1987381  ccgacaaacg  acggctgcgc  aaccattccc  atacggcctc  gcagcggaac  cgtctccatc
1987441  ctgaccgggt  tcctccgccg  gaacatgccc  gccatcggtc  tgagcctgct  gttctcgctc
1987501  gtcgtccagg  gactgacatt  gatcgtgccc  gcaggcaccg  gctatatggt  cgaccatggg
1987561  tcgctcgccg  cccaaagcgg  tttcccgccg  ttggtcgcga  cgatgctgct  tgcctcgctg
1987621  ctggtctact  atgcggtcgg  cgcgttgaac  accgtgatgc  tcacccgcgt  gcaggtgcga
1987681  ttcggacgat  acctgtcccg  ccgatacatg  accggcgtgc  tcgatcggga  gttcccgttc
1987741  ttcgtgaacc  gttccggtgg  tgacctgatc  taccgcgcga  acctggtcat  ggtcgtcgaa
1987801  cagatcgtga  ccggcagtct  gccgtcgacg  gtcgtgtcga  tggtgttcct  cgtggtctac
1987861  ctgatcatga  tgatcgccta  ttcagtgcca  ttgacgatgc  tgaccctgac  ggtgtgcgcg
1987921  gcggtgctcg  tcgtatccgt  catttattcc  ctgcgcaaca  ggacgctggt  cgagcgtgcg
1987981  accgtcgcgc  aggctgacgt  gcaacgcgcc  ttcatcgaaa  ccttctccgg  catcgaaact
1988041  gtcaaaagcc  tcaatttgga  aagccactgc  tacgaccgct  ggtcagcgcg  tctgggagcg
1988101  cagctcgact  accagactcg  gcaagggcgg  ctttcggcat  tgctgtcaag  cctgtcctcg
1988161  gcgctggtgt  tcgtgttgcc  gctatgcgtg  gtcgccttcg  gcatgacctt  cgtgggacgc
1988221  ggcacgctcg  cactgggtgc  cgtcgtcgga  ttcatgtcat  ggcgtccgc   attcgtcacg
1988281  ccattctccg  gcatcgtcgg  cgtcatcagc  cagatcatgg  cgttcgccac  ctatatgcgc
1988341  aagatttgcg  agatgattcc  cgccggtgaa  ggcggcggtg  cgtcgcttga  atgcgacgaa
1988401  ccgggtggcg  aaccgggtga  cgtcggactg  ggtgacggcg  gacggtccgc  atgtggtggg
1988461  ccgagtggtg  acgaatcggg  tgatggcata  ctcgaacggt  tgcatgccac  cggcgtggga
1988521  tactcgtaca  cggcgttcga  cgctcccgtt  ctctccgatg  tcgattgcga  catccgcaaa
```

Fig. 16 (continued)

```
1988581 ggcgacaaga tcgccatcgt cggccccact ggctcgggca aagcacgct gctgaaactg
1988641 ctcgccggac tcatcgaacc cgtctgtggc acggtgacca tcaacggcgg cggatgccgg
1988701 atttacgacg cggacagccg atggaaggcc ggcaggctgg cgtatgtgca tcaggaatcc
1988761 acgtgttca acgaaacctt gcgcgacaat atcacgctgc accgtccgtg gctgacggat
1988821 gacgacatcg tcagggcgtg cgaggttgcc ggcatcaacg aggggatgat ggatccggtc
1988881 gtcggcttgg acgccatggt cagtgaacgc ggcatgaacc tgtccggcgg ccaacggcag
1988941 aaggtcgcca tcgcgcgtgc ggtcgtcgga agaccggact tcctacttat ggacgaaccc
1989001 accagtgctc tggacaacga taccgagcga catgtcatga cggcgttgct cgactccgac
1989061 aatgcgtgca tcgtcgtggc gcacagactc gcatcgattc gggatttcga ccgcatccat
1989121 gtcatggatc atgggcagat cgtcgaatcc ggtacgcatg acgaactgct gcaggccggc
1989181 ggattgtatt cgcggctgta ccggcaggag tgagtgtccc cttacaccct tacgccttta
1989241 aaccccttacc ctttacacct tatcccttac accctcggct catgaggccc cccggattca
1989301 atttgtaagc gcaacgcttg tgttcgggct ggctgccttc gattgtagct tggcgatctc
1989361 ctcgtcccat acctcgttgg gcgttttgta gccgaggagc ttcatggggg tgtcgttgat
1989421 ctccccgacg atcgcgtcga ggtcctcctg ggccaagtcc tcgaacccgg ttcctttggg
1989481 cagatagcgg cggatcctgc cgttcctgtt ctcgttgctg ccacgctgcc aggaactgta
1989541 cgggtcggcg aagtacgtga gcatgcccag cgcctcgtcc accagcatgt gcaggctcgc
1989601 ctccgtgccg ttgtcccacg tgcggtcgac gcgcgcggcc ggcgggatgt ccttgaagat
1989661 ctcgtattcg gccctggccg tggcggacgc gctcttgtcg tcgacgagcc gggcgaacag
1989721 cctgcggctc ctgcgctcca cctgcgtgtt catgcagcgc ctcgacggcg cggcgccgac
1989781 caccgtgtcc gactgtattt cgtcaagtcg gtgtttcgtg tttagtcatg tattttttc
1989841 gggtttaggc agttgcatgc attttcctta tttttccggt tgcgcggagg tgttcctgcc
1989901 gaacatgagg gcctcactga cgcggcggct ctggccggtg aactcgagga gccgccgtg
1989961 gtgcacgatg cggtcgatga tcgctgcggc gagtttgtcg tccgcgaaga ccgtgcccca
1990021 tttactgaac tcgatgttcg tggtgaatat gatgctccgt ctttcgtagc tgcccgcgat
1990081 gatctggtag agcaggcgcg ccccgtcgat gtcgaagggt acgtagccga actcgtccag
1990141 tatgatcagg tcggcacggc cgatgtcccg gagcatcgtc tcgagcgtgc cgtcgcgttt
1990201 ggccttgccc agctggagga cgagctcggc ggtctgatgg aaccgcacgc ccagccccat
1990261 gtcgatcgcc ttcatgccca gcccgatcgc gagatgtgtc tttccgcgcc cggtcttgcc
1990321 gtagaacacc aggtcctgcg cgcgcgggat gaaaccgagc ctaggagct catcgagcat
1990381 gtagccgtcg gggagcctga cgttcgtgaa gtcgtagccg tcgagaccct tgacgacggg
1990441 gaaccgggcg cggcgcagga gcctgtcgtg cttcgcgcgt tccctgttcg ccagttccgt
1990501 gtcgagcagg cggtggacgg cgtcgacctg gcggggcgtg gcccagccgg cgaattcgtc
1990561 gatgctcgcc ttggagatga acagcttgcg ggccttctcg tagagccctt cgtccgtctt
1990621 cgtgttcatc gcccgccttc ctgcacgccg acgtccgcgg tgaacgcgat gtcgtattca
1990681 ctcagatccg gcctgtcatc gtcgtattcg atacccgcca cgccctcggc gagcctggcc
1990741 gcgagcagtg tgacaccggc gcggtccgcc ccgccggtcg attcgaggat ggaaagcatc
1990801 gcctcgaccg cgttcgccca cccggattcc ctgtcaacgc gtttgagggt ctgcagcgcc
1990861 tcgttgcg
```

SEQ ID NO:2
MFVRKTSIMCAMGNPNEIRLAIVDNDDFVLMGLAAFLSRHLPNVRLAWKANTGTDALEYATDPA
NEADILLVDMSLEDMPGDMVCREIRSRNRMLPLLAVTSFSLIRYARRAAEGGAQGIVSKADFPA
LCKAVKLVSDGHTLCVRVGGETIGFEDVDAAYHRLVRLPVNRIERLSEREKYAMELYSQSYKPT
QIARMMDVSAGTVKTYLDRVQNKLHLTSRAELIAYWWRRERW

SEQ ID NO:4
MVRRLAMETILVVRKKCLGVSKKNLVLSIVAMTCLAACIAEWILDSPESLNDGFIRIVYMLAVS
MLPLYPVPATWGIIVIAFLNELMPCLSQCDESWGVLVSLAIQGYAAVWWNGVTATVLLSISALL
NYAIYRENSEFGSFDGSINLVVLLWFVFLLGVWLRQRNRLEKKKELEKKAEIVRYNLQLAEGMH
DAMSGELTRMLVIVQEGIDASKEEELKRWRKLQNGINKVFQDLHSVMNYLSDDDHKQDEVFHVS
LAEHIQATLSESDRRLHDKGFCGHSSLRGVSSAMLNSWNQIIVNLLREIYTNIERYADKSEYSV
IVTFSNNAVDIVQVNKCRQKSRRCVTLGARKGLSIYSRLISGQGGFIRYEKDGEEWSFYCMLPL
LT

Fig. 16 (continued)

SEQ ID NO:6
MSINEKSIVGESFEDLSAADMAMLTGRNDDGVAPASLSFAVSVLSVSFSACSVTVVTRLASCGN
CK

SEQ ID NO:8
MKAILFRDCKACFQSFKNWGMVLIIMVTAIFVEMVASGAGILDPFTWAVFFGPFFIYSSCSVMV
SILYQDFRDGLFELYIQSGRSYWSYCWCKCLFPVILTVISVLLNLAFMRVLSSGFQITAGADDA
IGALIVSVLGTIVCSLGAMPMVYVSRNSDPTMAQLVLVLIAILLQLAYTLVVVNVMPLCLFSVG
YVVLVVVAIGISTGVFSRYFINTNIEL

SEQ ID NO:10
MTSMVAYVASRNPQSQTLRSVRLIQDAVSGNIDAEWTILTPNDTTILPSDGTASEFSTGVDHIE
LNGLDDSARVKKAIERCDYLILGSPTYGHNVSGDMKILMDRLTYWGHLFHLAGKPGMAMVSATT
NGFLEVGELMERFMESLGIIIDETAYHTTFTPFDEAMADQTAAAIVRALNTLRDGVVPETSERQ
ELAFQSYKRDYARRDGSDAESRYWRERGMFDCATFHEYVETRRKLPESVHAER

SEQ ID NO:12
MAATAMPDALRQYRASHAEDMLSATVEWKNRRNPLRDEDYQGIADALGDDASVVETVIADRERK
LSGHVEPAWSVELQTILNRYDSEEERVERTGYATAFAPFVAYVKAELQAHMSACSLPMNDERLI
EQCLSAYVERLLSIGLKTVVWELHVARQAGSLGDGDAKRQLRRYFELLATDEYRGHMYAKYPVL
LRFVTQTTVHYIDFVKEMLDRVSMDRDELASFAGVGDDFRLEDMSIDRGDAHDGGRAVAMLTIG
GRKIVYKPRDLHIHELFAGLVRRCERTKGFLPMRVSDVLTKSGYAYEEFVEHGTCEDARQVERY
YTRYGQLLGLVWLLHGDDMHHENIIASGEYPMVVDFETIATNHVTMDMPDGTDADIRVSTILRD
SLASSCLLPAKTAMSADGTSVDISAFETGEQTMPGIVASPVGLDSADAHYERNAVTFSKDGCAV
TLDDAVVDPYHYKRQILQGFRNTVAAAMTIDADEWDAMLSGEDTTVRVLVRNTSAYARFADFIH
HPSALKDMLDVEAILENLYVYPFRDKRIFASEYRQMLAGDIPMFTAQLTGHDLHAPDGTTIDGV
CERSVRERVLDTIGHLDEQAALQSRIIRNALRMEPGMEDAHPTASVSSDTDAEHYPIELGTRIA
DTAILQETDGTVSWLTANRSDTMAADKTVDERYEPGAPTSGLYDGMAGTGMFAAELYRRTHDER
WRDLCTRMMRSLMRRKDRGITYSGFTSGLSRSYCALRMANAGITSPEARRCMTQTVRMLPAYID
DMLPKLLQRDNPQPSFHLDYLTGAGSSIMLYLRLYDVFHDMRIVEQTSRLGRTVIRAFPETQRN
ADESDDMPYPTGAAHGLEGMAVAFWKLYAATGNREFAEFARMLWRKSDARRSGAKQEDAGKWCR
GKVGVLWARNELAATAGADGERFFEDENGRAFPDKADITALLGNADWDDDGVCHGRCGMIDTLI
SIGNANGDEWYRMQAQRLMDDMIAQARSSGRFRLRQSREFVDLSYFQGPVGVAYTMLRLNDPST
PSILALETR

SEQ ID NO:14
MTADHINHADRTDNGEHAIIAVEHVTFGYKKKQTVLEDIDFTVPQGQSLAILGYNGVGKTTLFR
LIVGLLRPREGRCVIDRRRVPSMRDVFQMTENGNLVGTMTVRDNIHFRQLLFRSGKGIADGGHT
VDSKRLEDEPLVRAFELEGHLDKKVAELSTGLRKRVGIVAGMLFDPHVIMLDEPSNAIDPITRS
LLVDYVNQLRADERTLLTVTHDLEYCWNVADRIIILDDKHLVKDMMLAEFDDYEAFTKASTLGR
DRTHVDFGLPARGRQA

SEQ ID NO:16
MRSWRRHRVPFIEQGEHSECGLAAAAMILAAFGHPVTMDELRRRYGAPRGGLSLANIVTVLSDS
GIRVRAVTTPSAEALKTVMTPCILHWDDNHFVVLDHYAYGRFRIADPANGRHAYTPGELAAHCS
GAVLIPQPTNDGCATIPIRPRSGTVSILTGFLRRNMPAIGLSLLFSLVVQGLTLIVPAGTGYMV

Fig. 16 (continued)

```
DHGSLAAQSGFPPLVATMLLASLLVYYAVGALNTVMLTRVQVRFGRYLSRRYMTGVLDREFPFF
VNRSGGDLIYRANLVMVVEQIVTGSLPSTVVSMVFLVVYLIMMIAYSVPLTMLTLTVCAAVLVV
SVIYSLRNRTLVERATVAQADVQRAFIETFSGIETVKSLNLESHCYDRWSARLGAQLDYQTRQG
RLSALLSSLSSALVFVLPLCVVAFGMTFVGRGTLALGAVVGFMSLASAFVTPFSGIVGVISQIM
AFATYMRKICEMIPAGEGGGASLECDEPGGEPGDVGLGDGGRSACGGPSGDESGDGILERLHAT
GVGYSYTAFDAPVLSDVDCDIRKGDKIAIVGPTGSGKSTLLKLLAGLIEPVCGTVTINGGGCRI
YDADSRWKAGRLAYVHQESTVFNETLRDNITLHRPWLTDDDIVRACEVAGINEGMMDPVVGLDA
MVSERGMNLSGGQRQKVAIARAVVGRPDFLLMDEPTSALDNDTERHVMTALLDSDNACIVVAHR
LASIRDFDRIHVMDHGQIVESGTHDELLQAGGLYSRLYRQE
```

US 7,960,505 B2

LANTIBIOTICS AND USES THEREOF

CONTINUING APPLICATION DATA

This application claims the benefit of U.S. Provisional Application Ser. No. 60/961,374, filed Jul. 20, 2007, which is incorporated by reference herein.

BACKGROUND

Recent molecular studies into the microbial diversity of the human intestine reveal a much greater diversity than previously recognized and very little is currently known of the contribution of individual groups to the human organism (Gill et al., 2006, *Science*, 312:1355-1359). One numerically dominant group of microbes, the bifidobacteria, is often suggested to be associated with good intestinal health given their overriding dominance in the feces of breast fed infants (Yoshioka et al., 1983, *Pediatrics*, 72:317-321). This phenomenon led to their discovery in 1899 by the pediatrician Henri Tissier and his subsequent use of these bacteria for the treatment of infantile diarrhea (Tissier, 1906, *Crit Rev Soc Biol*, 60:359-361). The proposed beneficial effect of bifidobacteria is further supported by the decrease of these bacteria in geriatric individuals and the concomitant increase of other microbial groups, most notably clostridia and *E. coli* (Mitsuoka et al., 1973, *Zentralbl Bakteriol [Orig A]*, 223:333-342, Hopkins et al., 2001, *Gut*, 48:198-205, Ishibashi et al, 1997, *Mal J Nutr,* 3:149-159). This has led to the growing worldwide interest of including bifidobacteria in foods specifically for their potential intestinal health benefits (O'Sullivan, Primary Sources of Probiotic Cultures, In: *Probiotics in food safety and human health*. Edited by Goktepe et al., Boca Raton: Taylor & Francis/CRC Press, 2006:91-107). However, clinical feeding studies with bifidobacteria show that while the strains can be detected in subject's feces during feeding trials, they are rapidly lost upon cessation of the studies pointing to a possible loss of competitive fitness of the strains for competition within the human intestinal environment (O'Sullivan, Primary Sources of Probiotic Cultures, In: *Probiotics in food safety and human health*. Edited by Goktepe et al., Boca Raton: Taylor & Francis/CRC Press, 2006: 91-107, Fukushima et al., 1998, *Int J Food Microbiol*, 42:39-44, Su et al, 2005, *FEMS Microbiol Lett*, 244:99-103. This may be due to attenuation of the strains, as the fermentation environment is very different to the buffered and anaerobic environment of the human colon.

Bacteriocins are peptide based antimicrobial compounds produced by many types of bacteria and are inhibitory to closely related bacteria. Frequently, the inhibitory spectrum is within the genus of the producing bacterium. A lantibiotic is a type of bacteriocin that has a wide inhibitory spectrum and is also post-translationly modified. Specifically, modification enzymes modify some amino acids into lantionine residues. Nisin, which is produced by certain strains of the lactic acid bacterium *Lactococcus lactis*, is a lantibiotic with the widest inhibitory spectrum of any lantibiotic described to date that extends to most gram positive bacteria. Given its broad spectrum it is widely used as a preservative and a shelf life extender. Unfortunately, spoilage and pathogenic bacteria are not just gram positive. Many pathogens, such as *E. coli* and *Salmonella* are gram negative and many spoilage bacteria are also gram negative, such as *Pseudomonas* and *Klebsiella*.

SUMMARY OF THE INVENTION

The present invention provides a lantibiotic, entitled bisin, from a probiotic culture of *Bifidobacterium longum* that inhibits both gram positive and gram negative bacteria. This is the first bacteriocin described to date to have natural inhibitory action against both gram positive and gram negative bacteria. It therefore has potential to be an effective shelf life extender in dairy products, given that the enzymatic activities of gram negative bacteria, particularly *Pseudomonas*, are responsible for a lot of defects.

The potential to produce a lantibiotic was first recognized from the genome sequence of the *Bifidobacterium longum* strain described herein; however, initial attempts at detecting a lantibiotic produced by the strain were unsuccessful. Further experiments were required before growth conditions were found that caused a lantibiotic to be produced. Subsequently, bioassays were used to test its spectrum of inhibition and clearly showed effective inhibition against both gram positive and gram negative indicators.

The present invention provides an isolated biologically active compound that includes an amino acid sequence, wherein the amino acid sequence of the compound and the amino acid sequence of SEQ ID NO:21 or SEQ ID NO:22 have at least 80% identity. The polypeptide sequence may include at least one conservative substitution of the amino acid sequence of SEQ ID NO:21 or SEQ ID NO:22. The compound has the characteristic of inhibiting growth of a Gram negative microbe in conditions that do not damage the outer membrane of the Gram negative microbe. The Gram negative may be an *E. coli*, a *Serratia proteus*, or a *Salmonella* spp. In some aspects it is preferably not a *P. aeruginaosa*. The compound inhibits growth of a Gram positive microbe, such as a *Lactobacillus* spp., *Lactococcus* spp., a *Streptococcus* spp., a *Staphylococcus* spp., or a *Bacillus* spp. The compound may be produced by a *Bifidobacterium*. The present invention also includes a composition having the isolated biologically active compound and a food product, and a composition having the isolated biologically active compound and a pharmaceutically acceptable carrier.

The present invention also provides an isolated polynucleotide including: (a) a nucleotide sequence encoding a polypeptide, wherein the amino acid sequence of the polypeptide and the amino acid sequence of SEQ ID NO:21 or SEQ ID NO:22 have at least 80% identity, or (b) the full complement of the nucleotide sequence of (a). The isolated polynucleotide may be operably linked to a heterologous regulatory sequence. The present invention also provides a vector containing the isolated polynucleotide, and a cell containing the isolated polynucleotide.

The present invention further provides isolated lantibiotic, wherein the lantibiotic inhibits growth of a Gram negative microbe in conditions that do not damage the outer membrane of the Gram negative microbe. The lantibiotic may include an amino acid sequence, wherein the amino acid sequence of the compound and the amino acid sequence of SEQ ID NO:21 or SEQ ID NO:22 have at least 80% identity. The Gram negative may be an *E. coli*, a *Serratia proteus*, or a *Salmonella* spp. In some aspects it is preferably not a *P. aeruginaosa*.

The present invention provides a composition with a lantibiotic and a food product, wherein the lantibiotic has the characteristic of inhibiting growth of a Gram negative microbe in conditions that do not damage the outer membrane of the Gram negative microbe. The lantibiotic may be present on the surface of the food product, in the food product, or the combination. The lantibiotic may include an amino acid sequence, wherein the amino acid sequence of the lantibiotic and the amino acid sequence of SEQ ID NO:21 or SEQ ID NO:22 have at least 80% identity. The Gram negative may be an *E. coli*, a *Serratia proteus*, or a *Salmonella* spp.

The present invention provides a composition with a lantibiotic and a pharmaceutically acceptable carrier, wherein the lantibiotic includes the characteristic of inhibiting growth of a Gram negative microbe in conditions that do not damage the outer membrane of the Gram negative microbe. The lantibiotic may include an amino acid sequence, wherein the amino acid sequence of the lantibiotic and the amino acid sequence of SEQ ID NO:21 or SEQ ID NO:22 have at least 80% identity. The Gram negative may be an *E. coli*, a *Serratia proteus*, or a *Salmonella* spp.

The present invention also provides methods for producing the compounds described herein. The methods may include growing an isolated *Bifidobacterium* under conditions suitable for producing a lantibiotic, wherein the *Bifidobacterium* produces a lantibiotic. The method may further include isolating the lantibiotic. The growing may include growing the *Bifidobacterium*, preferably *B. longum*, on a surface. The present invention also includes a lantibiotic produced by the method.

Method for producing a lantibiotic may include growing a microbe that includes a polynucleotide encoding a polypeptide, wherein the amino acid sequence of the polypeptide and the amino acid sequence of SEQ ID NO:21 or SEQ ID NO:22 have at least 80% identity, wherein the microbe is grown under conditions suitable for producing the polypeptide, and wherein the microbe produces the polypeptide. The microbe may further include a polynucleotide encoding a polypeptide selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, or a combination thereof. The growing may include growing the *Bifidobacterium*, preferably *B. longum*, on a surface. The present invention also includes a polypeptide produced by the method. The method may further include isolating the polypeptide, for instance by extraction with a composition that includes an alcohol, such as methanol.

Further provided by the present invention are methods for using lantibiotics. A method may include adding the lantibiotic to a food product, wherein the lantibiotic includes the characteristic of inhibiting growth of a Gram negative microbe in conditions that do not damage the outer membrane of the Gram negative microbe. The method may include applying the lantibiotic to the surface of the food product, for instance, by bringing a surface of a casing, film, or packaging material comprising the lantibiotic into contact with the food product. The adding may include adding the lantibiotic to the food product. The lantibiotic may act as a food preservative.

The present invention provides a dentifrice, such as a mouthwash or a toothpaste, that includes a biologically active compound with an amino acid sequence, wherein the amino acid sequence of the compound and the amino acid sequence of SEQ ID NO:21 or SEQ ID NO:22 have at least 80% identity, wherein the compound has the characteristic of inhibiting growth of a Gram negative microbe in conditions that do not damage the outer membrane of the Gram negative microbe.

Also provided by the present invention is a method for using a lantibiotic that includes administering a composition with the lantibiotic to an animal, such as a human, wherein the subject has or is at risk of an infection by a microbe that is inhibited by the lantibiotic, and wherein the lantibiotic has the characteristic of inhibiting growth of a Gram negative microbe in conditions that do not damage the outer membrane of the Gram negative microbe. The composition may include a pharmaceutically acceptable carrier, and the composition may be administered topically.

The present invention also provides isolated biologically active polypeptides, wherein the amino acid sequence of the polypeptide and the amino acid sequence of SEQ ID NO:2, SEQ ID NO:4, SEQ ID NO:8, SEQ ID NO:10, SEQ ID NO:12, SEQ ID NO:14, or SEQ ID NO:16, have at least 80% identity. Also included in the invention are isolated polynucleotides encoding the polypeptides.

The present invention further provides a *Bifidobacterium* that produces a lantibiotic. The lantibiotic has the characteristic of inhibiting growth of a Gram negative microbe in conditions that do not damage the outer membrane of the Gram negative microbe. The Gram negative may be an *E. coli*, a *Serratia proteus*, or a *Salmonella* spp. The *Bifidobacterium* may be encapsulated or in tablet form, for instance, and may be present in a food product. The present invention also provides method that includes administering a *Bifidobacterium* to an animal in need thereof, wherein the *Bifidobacterium* will produce a lantibiotic that has the characteristic of inhibiting growth of a Gram negative microbe in conditions that do not damage the outer membrane of the Gram negative microbe.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Organization of mobile integrase cassettes (MIC) in *B. longum* DJO10A. (A) and NCC2705, (B). Orfs 1, 2 and 3 refer to three contiguous, but different xerC integrase genes. P, a conserved 20 bp palindrome (TTAAACCGACATCG-GTTTAA (SEQ ID NO:24), which has an 11 bp extension in MIC III. IR, 96 bp inverted repeat (IR) (GATTAAGC-CGGGTTTGTTGTTAAGCCGGGGAACGGT-TCGGGGTCTTGGT GGCTGGCCGTGTCCCATGTG-GTTTCCCGGCTTAACGTTCCGGGTTAT (SEQ ID NO:25)), that has a 3 bp extension in MIC I and II, a 5 bp extension in MIC III and a 1 bp extension in MIC 1, 2 and 3. IS, insertion sequence.

FIG. 5. Arsenic resistance of selected bacteria. (A) Genetic organization of arsenic resistance gene clusters compiled from the completed genome sequences of *Bifidobacterium longum* DJO10A, *Bacillus subtilis* 168 (Kunst et al., 1997, *Nature* 1997, 390:249-256), *Bacteroides thetaiotamicron* VPI-5482 (Xu et al., 2003, *Science* 2003, 299:2074-2076), *Lactobacillus brevis* ATCC 367 (Makarova et al., *Proc Natl Acad Sci USA* 103:15611-15616), *L. plantarum* WCFS1 (Kleerebezem et al., 2003, *Proc Natl Acad Sci USA* 2003, 100:1990-1995), *L. johnsonii* NCC 533 (Pridmore et al., 2004, *Proc Natl Acad Sci USA* 2004, 101:2512-2517) and *E. coli* K-12 (Sofia et al., 1994, *Nucleic Acids Res* 1994, 22:2576-2586). a, 48 kb element that is excised by the site-specific recombinase SpoIVCA during sporulation, b, indicates a plasmid sequence, arsR, repressor, arsA, arsenite stimulated ATPase, arsB, arsenite efflux pump, arsC, arsenate reductase, arsD, arsenic chaperone, hyp, hypothetical protein. (B) Comparison of arsenic resistance activity in *B. longum* DJO10A with fermentation adapted *B. animalis* subsp. *lactis* strains, *E. coli* and *Lactobacillus plantarum*. c, calculated from data presented in van Kranenburg et al., (van Kranenburg et al., 2005, *Appl Environ Microbiol* 2005, 71:1223-1230).

FIG. 9. Conserved structure of the oriC region. This consists of three clusters, in the two *B. longum* genomes. The DnaA boxes consist of 7 types, designated A to G as follows: Type A (TTATCCACA), Type B (TTGTCCACA), Type C (TTTTCCACA), Type D (TTACCCACA), Type E (TTATCCACC), Type F (TTATTCACA), Type G (TTATGCACA).

FIG. 14. Loss of the lantibiotic gene cluster from *B. longum* DJO10A-JH1. (A) Detection of DJO10A specific gene clusters in *B. longum* DJO10A and its fermentation adapted isolate DJO10A-JH1 by PCR. M, 1 kb DNA ladder (Invitrogen); lane 1, unique region 15; lane 2, unique region 6; lane 3, unique region 9; lane 4, unique region 11; lane 5, unique region 5; lane 6, unique region 7; lane 7, unique region 12; lane 8, 16S rRNA partial gene. The arrow indicates the lantibiotic encoded unique region 12 that is missing from strain DJO10A-JH1. (B) Southern blot analysis using a lanM probe and the EcoRI-digested genomes of *B. longum* strains DJO10A and DJO10A-JH1. The 1.7 kb EcoRI band containing lanM is indicated with an arrow.

FIG. 16. Portion of genomic sequence of *B. longum* DJO10A (Genbank Accession No. CP000605) including the lantibiotic-encoding gene cluster (SEQ ID NO:23). Present within SEQ ID NO:23: nucleotides 1979049-1979753 (SEQ ID NO:1) and the polypeptide encoded thereby (SEQ ID NO:2); nucleotides 1979747-1980907 (SEQ ID NO:3) and the polypeptide encoded thereby (SEQ ID NO:4); nucleotides 1981217-1981417 (SEQ ID NO:5) and the polypeptide encoded thereby (SEQ ID NO:6); nucleotides 1981501-1982160 (SEQ ID NO:7) and the polypeptide encoded thereby (SEQ ID NO:8); nucleotides 1982200-1982937 (SEQ ID NO:9) and the polypeptide encoded thereby (SEQ ID NO:10); nucleotides 1983009-1986110 (SEQ ID NO:11) and the polypeptide encoded thereby (SEQ ID NO:12); nucleotides 1986161-1986979 (SEQ ID NO:13) and the polypeptide encoded thereby (SEQ ID NO:14); nucleotides 1986976-1989213 (SEQ ID NO:15) and the polypeptide encoded thereby (SEQ ID NO:16).

DETAILED DESCRIPTION OF ILLUSTRATIVE EMBODIMENTS

Figure 2:
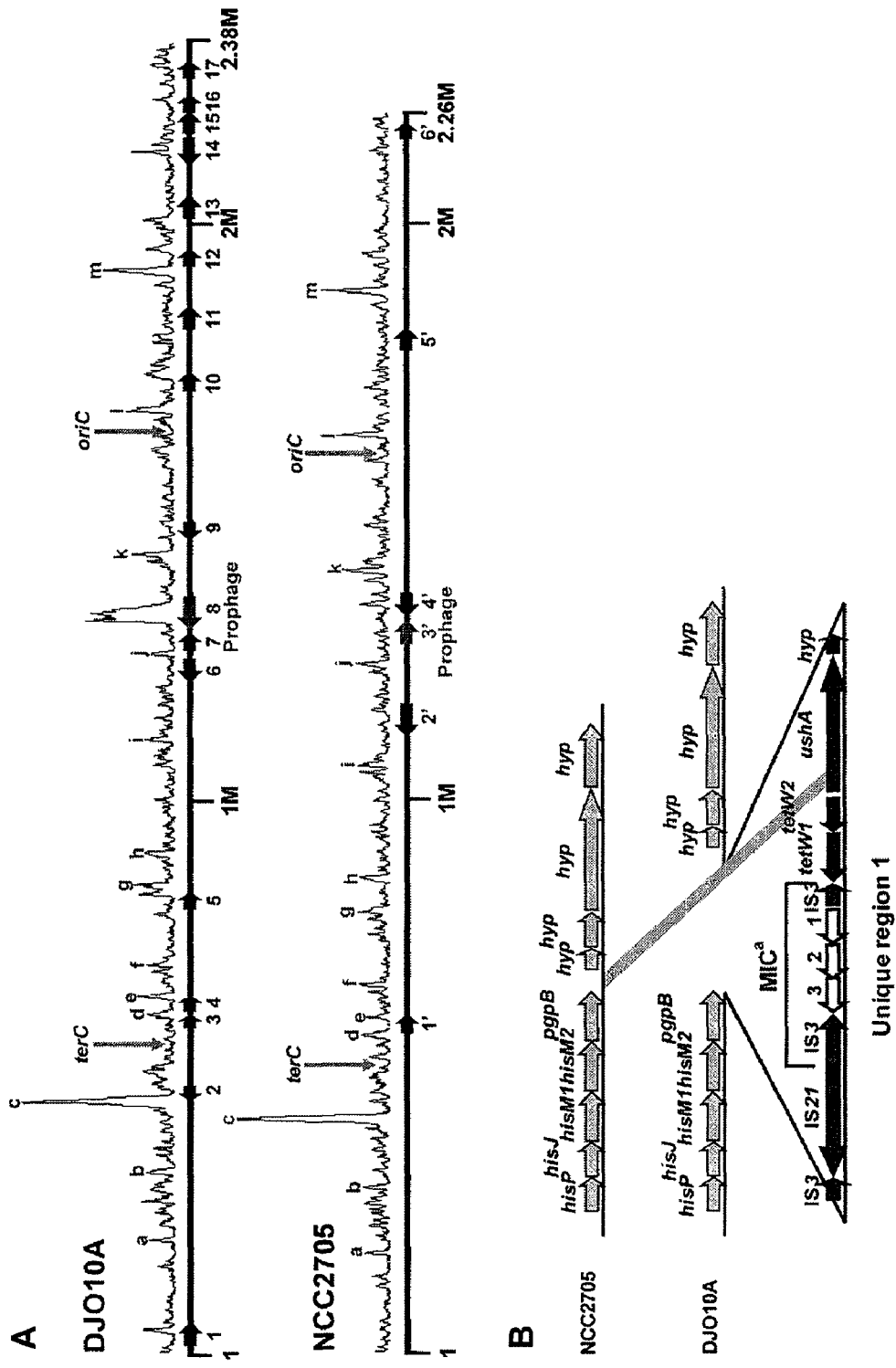
FIG. 2. Genome unique regions. (A) Base deviation index (BDI) analysis of the *B. longum* DJO10A and NCC2705 genomes. Unique regions of each genome as defined in the text are numbered. The locations of oriC and terC are indicated by green arrows. Letters refer to predicted gene phenotypes from regions with definitive BDI peaks that are present in both genomes, a, GTPase, b, cation transport ATPase, c, DNA partitioning protein, d, choloylglycine hydrolase, e, glutamine synthase beta chain, f, alanyl-tRNA synthetase, g, pyruvate kinase, h, cation transport ATPase, I, fibronectin type III, j, aminopeptidase C, k, subtilisin-like serine protease, 1, sortase, m, fatty acid synthase. (B) Organization of the unique region 1 showing the location of a 361 bp DNA remnant, indicated by the green bar, from the ushA gene remaining at the predicted deletion location in NCC2705. Sky blue colored ORFs indicate common genes between both genomes. a, mobile integrase cassette.

The present invention provides compounds that inhibit the growth of certain microbes. A compound of the present invention includes a polypeptide. As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring. A compound of the present invention can be referred to herein as a lantibiotic. Preferably, a compound of the present invention is isolated. As used herein, an "isolated" polypeptide, such as a lantibiotic, or polynucleotide refers to a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities.

Without intending to be limiting, during production of a compound of the present invention by a microbe, such as a *Bifidobacterium*, a prepeptide is produced and subsequently processed in three steps; dehydration of certain amino acids, formation of thioether linkages between certain amino acids, and cleavage by a signal peptidase. The initial prepeptide may have the amino acid sequence SEQ ID NO:6.

The prepeptide is processed by dehydration to result in an intermediate. Serine residues may be dehydrated to form didehydroalanine. Thus, with reference to SEQ ID NO:6, the serine amino acids at position 36, 38, 42, 45, 47, 49, 52, 61 or a combination thereof, may be dehydrated to form didehydroalanine. Preferably, the serine amino acids at positions 47, 49, and 61 are dehydrated to form didehydroalanine. Threonine amino acids may be dehydrated to form didehydrobutyrine. Thus, with reference to SEQ ID NO:6, the threonine amino acids at positions 54, 57 or a combination thereof, may be dehydrated to form didehydrobutyrine. Preferably, the threonines at both positions 54 and 57 are dehydrated to form didehydrobutyrine.

Thus, an intermediate polypeptide resulting from the dehydration amino acids may have the following structure:
Methionine-Serine-Isoleucine-Aspartic acid-Glutamic acid-Lysine-Serine-Isoleucine-Valine-Glycine-Glutamic acid-Serine-Phenylalanine-Glutamic acid-Aspartic acid-Leucine-Serine-Alanine-Alanine-Aspartic acid-Methionine-Alanine-Methionine-Leucine-Threonine-Glycine-Arginine-Asparagine-Aspartic acid-Aspartic acid-Glycine-Valine-Alanine-proline-alanine-Xaa1-leucine-Xaa2-phenylalanine-alanine-valine-Xaa3-valine-leucine-Xaa4-valine-Xaa5-phenylalanine-Xaa6-alanine-cysteine-Xaa7-valine-Xaa8-valine-valine-Xaa9-arginine-leucine-alanine-Xaa10-cysteine-glycine-asparagine-cysteine-lysine (SEQ ID NO:19)
where Xaa1, 2, 3, 4, 5, 6, 7, and 10 are each independently serine or didehydroalanine; and Xaa8 and 9 are each independently threonine or didehydrobutyrine. A preferred example of an intermediate polypeptide resulting from the dehydration of certain amino acids is
Methionine-Serine-Isoleucine-Aspargine-Glutamic acid-Lysine-Serine-Isoleucine-Valline-Glycine-Glutamic acid-Serine-Phenylalanine-Glutamic acid-Aspartic acid-Leucine-Serine-Alanine-Alanine-Aspartic acid-Methionine-Alanine-Methionine-Leucine-Threonine-Glycine-Arginine-Asparagine-Aspartic acid-Aspartic acid-Glycine-Valine-Alanine-proline-alanine-serine-leucine-serine-phenylalanine-alanine-valine-serine-valine-leucine-serine-valine-didehydroalanine-phenylalanine-didehydroalanine-alanine-cysteine-serine-valine-didehydrobutyrine-valine-valine-didehydrobutyrine-arginine-leucine-alanine-didehydroalanine-cysteine-glycine-asparagine-cysteine-lysine (SEQ ID NO:20).

The polypeptide resulting from the dehydration of certain amino acids is further processed to form thioether linkages between certain amino acids. Didehydrobutyrine residues may be processed to form 2-aminobutyric acid (Abu) when used to form a thioether linkage with another amino acid, didehydroalanine residues may be processed to form alanine when used to form a thioether linkage with another amino acid, and cysteine residues may be processed to form alanine when used to form a thioether linkage with another amino acid. As has been observed in lantibiotics, lanthionine and 3-methyllanthionine residues result from the formation of thioether linkages between different amino acids.

The processed polypeptide is further processed by cleavage between two amino acids. The expected cleavage site is between amino acids 33 and 34. Other cleavage sites in SEQ ID NO:6 may be used to result in a processed peptide.

Thus, a compound of the present invention may have the following sequence:

proline-alanine-Xaa1-leucine-Xaa2-phenylalanine-alanine-valine-Xaa3-valine-leucine-Xaa4-valine-Xaa5-phenylalanine-Xaa6-alanine-Xaa7-Xaa8-valine-Xaa9-valine-valine-Xaa10-arginine-leucine-alanine-Xaa11-Xaa12-glycine-asparagine-Xaa13-lysine (SEQ ID NO:21)

where Xaa1, 2, 3, 4, 5, 6, 8, and 11 are each independently serine, didehydroalanine, or alanine; Xaa7, 12, and 13 are each independently cysteine or alanine, and Xaa9 and 10 are each independently threonine, didehydrobutyrine, or 2-aminobutyric acid. A preferred example of a compound of the present invention is proline-alanine-serine-leucine-serine-phenylalanine-alanine-valine-serine-valine-leucine-serine-valine-alanine-phenylalanine-didehydroalanine-alanine-alanine-serine-valine-didehydrobutyrine-valine-valine-2-aminobutyric acid-arginine-leucine-alanine-alanine-alanine-glycine-asparagine-alanine-lysine (SEQ ID NO:22).

A compound may have at least 1, at least 2, at least 3, at least 4, at least 5, at least 6 thioether cross links. Preferably, a compound of the present invention has at least 1, more preferably at least 2, most preferably 3 cross links. The cross links can be between any two residues at positions Xaa 1, 2, 3, 4, 5, 6, 7, 8, 9, 10, 11, 12, and 13 of SEQ ID NO:21, in any combination. Preferably, each cross link includes one cysteine residue, i.e., Xaa 7, 12, or 13 of SEQ ID NO:21. A preferred example of a compound of the present invention is SEQ ID NO:22 with thioether cross links between the amino acids at positions 14 (Xaa 5) and 18 (Xaa 7), positions 24 (Xaa 10) and 29 (Xaa 12), and positions 28 (Xaa 11) and 32 (Xaa 13).

A compound of the present invention may include polypeptides other than those depicted at SEQ ID NOs: 19, 20, 21, or 22, preferably, SEQ ID NO:21. For instance, a compound of the present invention may include those having structural similarity with another amino acid sequence. The similarity is referred to as structural similarity and is generally determined by aligning the residues of the two amino acid sequences (i.e., a candidate amino acid sequence and the amino acid sequence of SEQ ID NOs: 19, 20, 21, or 22) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in an amino acid sequence, such as SEQ ID NO:21. A candidate amino acid sequence may be isolated from a *Bifidobacterium*, or may be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities." Preferably, a compound of the present invention also includes polypeptides with an amino acid sequence having at least 80% amino acid identity, at least 81% amino acid identity, at least 82% amino acid identity, at least 83% amino acid identity, at least 84% amino acid identity, at least 85% amino acid identity, at least 86% amino acid identity, at least 87% amino acid identity, at least 88% amino acid identity, at least 89% amino acid identity, at least 90% amino acid identity, at least 91% amino acid identity, at least 92% amino acid identity, at least 93% amino acid identity, at least 94% amino acid identity, at least 95% amino acid identity, at least 96% amino acid identity, at least 97% amino acid identity, at least 98% amino acid identity, or at least 99% amino acid identity to SEQ ID NOs: 19, 20, 21, or 22, preferably SEQ ID NO:21.

A compound of the present invention having structural similarity to SEQ ID NOs: 19, 20, 21, or 22, preferably SEQ ID NO:21, may include one or more conservative substitutions of the sequence disclosed at SEQ ID NOs: 19, 20, 21, or 22. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) can generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, including amino acids not coded for in the standard genetic code and resulting from, for instance, post-translational modification of an amino acid, but also include artificial amino acids. A conservative substitution may be present at any location, preferably, at position 1, 2, 4, 6, 7, 8, 10, 11, 13, 15, 17, 20, 22, 23, 25, 26, 27, 30, 31, 33, or a combination thereof of SEQ ID NO:21.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Preferably, a compound of the present invention is biologically active. As used herein, a "biologically active" compound or a compound having "biological activity" is one that inhibits growth of an indicator microbe. When the lantibiotic to be tested for biological activity is being produced by a microbe, preferably a *Bifidobacterium*, the microbe may be used to inoculate the center of an agar plate and incubated for a period of time, for instance, 2 days, to allow for replication of the microbe and production of the lantibiotic. Preferably, the agar plate is MRS or BLIM. Next, an indicator strain, previously grown on a different plate or in broth, is suspended in a molten top agar, for instance, 0.5% agar, and poured over the plate that contains the microbe producing the lantibiotic to be tested. The amount of indicator strain used can vary, but is typically added at a concentration that will yield visible growth in 1 to 2 days in the absence of a lantibiotic-producing microbe. The top agar is allowed to cool and harden, and the plate is incubated under conditions to allow growth of the indicator strain. The absence of the indicator strain around the microbe inoculated in the middle of the plate indicates the microbe is producing a lantibiotic with biological activity. The plate may be completely devoid of growth of the indicator strain, or there may be a halo of no indicator strain in the center of the plate.

When the lantibiotic to be tested for biological activity is isolated or purified, a hole may be cut in the center of an agar plate, and a solution containing an isolated or purified lantibiotic may be added to the hole and allowed to diffuse into the agar. Next, an indicator strain, previously grown on a different plate or in broth, is suspended in a molten top agar, for instance, 0.5% agar, and poured over the plate that contains the isolated or purified lantibiotic. The top agar is allowed to cool and harden, and the plate is incubated under conditions to allow growth of the indicator strain. The absence of the indicator strain around the microbe inoculated in the middle of the plate indicates the microbe is producing a lantibiotic with biological activity. The plate may be completely devoid of growth of the indicator strain, or there may be a halo of no indicator strain in the center of the plate.

Some lantibiotics are known to have some biological activity against gram negative microbes, but typically the biological activity exists only if the outer membrane of the gram negative microbe is damaged before exposure to the lantibiotic. The lantibiotic of the present invention has biological activity against gram negative microbes in the absence of damage to the outer membrane. Accordingly, testing whether a lantibiotic has biological activity is preferably done under conditions that do not damage the outer membrane of a gram negative microbe. Such conditions include, for instance, inclusion of a chelator in the medium, subjecting the indicator microbe to conditions of osmotic shock, heat, hydrostatic pressure, exposure to sub-lethal antimicrobials that effect the lipopolysaccarhide of the outer membrane, sub-lethal microwave exposure, and sublethal sonication. Likewise, some lantibiotics are known to have some biological activity against gram negative microbes, but typically the biological activity exists only if the gram negative microbe is exposed to higher concentrations of the lantibiotic than are used to inhibit a gram positive microbe (Hillman, U.S. Patent Application 20020128186. The lantibiotic of the present invention has biological activity against gram negative microbes and gram positive microbes when used at the same concentration.

Preferred indicator strains include, for instance, *Micrococcus letteus, Lactococcus lactis, Staphylococcus aureus, Staphylococcus epidermdis, E. coli, Serratia marcescens*, and *Proteus vulgaris*.

A compound of the present invention also has the characteristics of being resistant to heating to 100° C. for 10 minutes, inactivated by proteolytic digestion with pepsin at pH 2 and pronase E at pH7.5, and not inactivated by proteolytic digestion with α-Chymotrypsin, proteinase K, trypsin, and thermolysin. The compound is predicted to have an isoelectric point of 9.5, and a molecular weight of 3291.8 Daltons.

The present invention also provides other isolated polypeptides. Without intending to be limiting, production of a compound of the present invention, for instance, SEQ ID NO:22, by a microbe such as a *Bifidobacterium*, is facilitated by 7 other polypeptides. The naturally occurring versions of these 7 polypeptides are encoded by a set of coding regions including the coding region encoding the naturally occurring preprotein SEQ ID NO:6, and the expression of each of these 7 polypeptide results in the production of a compound, for instance, SEQ ID NO:22.

These 7 polypeptides are a response regulator of two component system (SEQ ID NO:2), a signal transduction histidine kinase (SEQ ID NO:4), a response regulator (SEQ ID NO:8), a prepeptide modification polypeptide (SEQ ID NO:10), a modifying enzyme (SEQ ID NO:12), an immunity polypeptide (SEQ ID NO:14), and a transporter polypeptide (SEQ ID NO:16). The transporter polypeptide is predicted to include protease capability to cleave the prepeptide. Also included in the invention are polypeptides having structural similarity with the amino acid sequence of SEQ ID NO:2, SEQ ID NO:4, SEQ ID NO:8, SEQ ID NO:10, SEQ ID NO:12, SEQ ID NO:14, or SEQ ID NO:16. The similarity is referred to as structural similarity and is generally determined by aligning the residues of the two amino acid sequences (i.e., a candidate amino acid sequence and the amino acid sequence of SEQ ID NO:2, SEQ ID NO:4, SEQ ID NO:8, SEQ ID NO:10, SEQ ID NO:12, SEQ ID NO:14, or SEQ ID NO:16) as described above. Preferably, a polypeptide of this aspect of the invention also includes polypeptides with an amino acid sequence having at least 80% amino acid identity, at least 81% amino acid identity, at least 82% amino acid identity, at least 83% amino acid identity, at least 84% amino acid identity, at least 85% amino acid identity, at least 86% amino acid identity, at least 87% amino acid identity, at least 88% amino acid identity, at least 89% amino acid identity, at least 90% amino acid identity, at least 91% amino acid identity, at least 92% amino acid identity, at least 93% amino acid identity, at least 94% amino acid identity, at least 95% amino acid identity, at least 96% amino acid identity, at least 97% amino acid identity, at least 98% amino acid identity, or at least 99% amino acid identity to SEQ ID NO:2, SEQ ID NO:4, SEQ ID NO:8, SEQ ID NO:10, SEQ ID NO:12, SEQ ID NO:14, or SEQ ID NO:16. A polypeptide the present invention having structural similarity to SEQ ID NO:2, SEQ ID NO:4, SEQ ID NO:8, SEQ ID NO:10, SEQ ID NO:12, SEQ ID NO:14, or SEQ ID NO:16 may include one or more conservative substitutions of the sequence disclosed at SEQ ID NO:2, SEQ ID NO:4, SEQ ID NO:8, SEQ ID NO:10, SEQ ID NO:12, SEQ ID NO:14, or SEQ ID NO:16.

A polypeptide having structural similarity to SEQ ID NO:2, SEQ ID NO:4, SEQ ID NO:8, SEQ ID NO:10, SEQ ID NO:12, SEQ ID NO:14, or SEQ ID NO:16 preferably has activity of producing a biologically active compound of SEQ ID NO:22. Whether a polypeptide having structural similarity to SEQ ID NO:2, SEQ ID NO:4, SEQ ID NO:8, SEQ ID NO:10, SEQ ID NO:12, SEQ ID NO:14, or SEQ ID NO:16 has activity can be determined by expressing one of the polypeptides with an altered amino acid sequence in a microbe, preferably a *Bifidobacterium*, with the other naturally occurring polypeptides, and determining whether a biologically active compound of the present invention is produced. For instance, if a polypeptide having structural similarity to SEQ ID NO:2 is to be tested for activity, it may be expressed in a cell with SEQ ID NO:4, SEQ ID NO:6, SEQ ID NO:8, SEQ ID NO:10, SEQ ID NO:12, SEQ ID NO:14, and SEQ ID NO:16, and the cell grown under conditions suitable for the production of a compound of the present invention. If the cell produces a compound having biological activity, then the tested polypeptide, i.e., the polypeptide having structural similarity to SEQ ID NO:2, is active.

Polynucleotides

The present invention also provides polynucleotides, preferably isolated polynucleotides. As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

One polynucleotide of the present invention includes SEQ ID NO:17 (nucleotides 1981316-1981417 of SEQ ID NO:23), which encodes the polypeptide depicted at amino acids 34-66 of SEQ ID NO:6. It should be understood that a polynucleotide encoding a polypeptide represented by amino acids 34-66 of SEQ ID NO:6 is not limited to the nucleotide sequence disclosed at SEQ ID NO:17, but also includes the class of polynucleotides encoding such a polypeptide as a result of the degeneracy of the genetic code. For example, the naturally occurring nucleotide sequence SEQ ID NO:17 is but one member of the class of nucleotide sequences encoding a polypeptide having the amino acid sequence depicted at amino acids 34-66 of SEQ ID NO:6.

Other polynucleotides encoding a biologically active polypeptide of the present invention include those having structural similarity with the nucleotide sequence of SEQ ID NO:17. The similarity is referred to as structural similarity and is determined by aligning the residues of the two polynucleotides (i.e., the nucleotide sequence of the candidate sequence and the nucleotide sequence of SEQ ID NO:17) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to SEQ ID NO:17. A candidate nucleotide sequence may be isolated from a *Bifidobacterium*, or may be produced using recombinant techniques, or chemically or enzymatically synthesized. Preferably, two nucleotide sequences are compared using the BESTFIT algorithm in the GCG package (version 10.2, Madison Wis.), or the Blastn program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, structural similarity is referred to as "identities." Preferably, a polynucleotide includes a nucleotide sequence having at least 80% nucleotide identity, at least 81% nucleotide identity, at least 82% nucleotide identity, at least 83% nucleotide identity, at least 84% nucleotide identity, at least 85% nucleotide identity, at least 86% nucleotide identity, at least 87% nucleotide identity, at least 88% nucleotide identity, at least 89% nucleotide identity, at least 90% nucleotide identity, at least 91% nucleotide identity, at least 92% nucleotide identity, at least 93% nucleotide identity, at least 94% nucleotide identity, at least 95% nucleotide identity, at least 96% nucleotide identity, at least 97% nucleotide identity, at least 98% nucleotide identity, or at least 99% nucleotide identity to SEQ ID NO:17. Preferably, a nucleotide sequence having structural similarity to SEQ ID NO:17 encodes a compound of the present invention having biological activity.

Optionally, a polynucleotide identical to, or having structural similarity with SEQ ID NO:17 includes an additional nucleotide sequence located immediately 5' or upstream of SEQ ID NO:17. This optional sequence encodes a polypeptide corresponding to the amino terminal region of the prepeptide that is removed during processing, i.e., amino acids 1-33 of SEQ ID NO:6. These nucleotides are disclosed at nucleotides 1-99 of SEQ ID NO:5. It should be understood that a polynucleotide encoding a polypeptide represented by amino acids 1-33 of SEQ ID NO:6 is not limited to the nucleotide sequence disclosed at nucleotides 1-99 of SEQ ID NO:5, but also includes the class of polynucleotides encoding such a polypeptide as a result of the degeneracy of the genetic code.

Other isolated polynucleotides encoding the amino terminal region of the prepeptide include those having structural similarity with the nucleotide sequence of nucleotides 1-99 of SEQ ID NO:5. The similarity is referred to as structural similarity and is determined by aligning the residues of the two polynucleotides (i.e., the nucleotide sequence of the candidate sequence and nucleotides 1-99 of SEQ ID NO:5) as described above. Preferably, such a polynucleotide includes a nucleotide sequence having at least 80% nucleotide identity, at least 81% nucleotide identity, at least 82% nucleotide identity, at least 83% nucleotide identity, at least 84% nucleotide identity, at least 85% nucleotide identity, at least 86% nucleotide identity, at least 87% nucleotide identity, at least 88% nucleotide identity, at least 89% nucleotide identity, at least 90% nucleotide identity, at least 91% nucleotide identity, at least 92% nucleotide identity, at least 93% nucleotide identity, at least 94% nucleotide identity, at least 95% nucleotide identity, at least 96% nucleotide identity, at least 97% nucleotide identity, at least 98% nucleotide identity, or at least 99% nucleotide identity to nucleotides 1-99 of SEQ ID NO:5.

The present invention also includes isolated polynucleotides encoding the 7 polypeptides that facilitate production of a compound of the present invention. These polynucleotides include SEQ ID NO:1, SEQ ID NO:3, SEQ ID NO:7, SEQ ID NO:9, SEQ ID NO:11, SEQ ID NO:13, and SEQ ID NO:15. These polynucleotides encode SEQ ID NO:2, SEQ ID NO:4, SEQ ID NO:8, SEQ ID NO:10, SEQ ID NO:12, SEQ ID NO:14, and SEQ ID NO:16, respectively. It should be understood that a polynucleotide encoding a polypeptide represented by SEQ ID NO:2, SEQ ID NO:4, SEQ ID NO:8, SEQ ID NO:10, SEQ ID NO:12, SEQ ID NO:14, or SEQ ID NO:16 is not limited to the nucleotide sequence disclosed at SEQ ID NO:1, SEQ ID NO:3, SEQ ID NO:7, SEQ ID NO:9, SEQ ID NO:11, SEQ ID NO:13, or SEQ ID NO:15, but also includes the class of polynucleotides encoding such a polypeptide as a result of the degeneracy of the genetic code.

Other polynucleotides encoding on of the 7 polypeptides that facilitate expression of a compound of the present invention include those having structural similarity with the nucleotide sequence of SEQ ID NO:1, SEQ ID NO:3, SEQ ID NO:7, SEQ ID NO:9, SEQ ID NO:11, SEQ ID NO:13, or SEQ ID NO:15. The similarity is referred to as structural similarity and is determined by aligning the residues of the two polynucleotides (e.g., the nucleotide sequence of the candidate sequence and the nucleotide sequence of SEQ ID NO:1) as described above. Preferably, a polynucleotide includes a nucleotide sequence having at least 80% nucleotide identity, at least 81% nucleotide identity, at least 82% nucleotide identity, at least 83% nucleotide identity, at least 84% nucleotide identity, at least 85% nucleotide identity, at least 86% nucleotide identity, at least 87% nucleotide identity, at least 88% nucleotide identity, at least 89% nucleotide identity, at least 90% nucleotide identity, at least 91% nucleotide identity, at least 92% nucleotide identity, at least 93% nucleotide identity, at least 94% nucleotide identity, at least 95% nucleotide identity, at least 96% nucleotide identity, at least 97% nucleotide identity, at least 98% nucleotide identity, or at least 99% nucleotide identity to SEQ ID NO:1, SEQ ID NO:3, SEQ ID NO:7, SEQ ID NO:9, SEQ ID NO:11, SEQ ID NO:13, or SEQ ID NO:15. Preferably, a nucleotide sequence having structural similarity to SEQ ID NO:1, SEQ ID NO:3, SEQ ID NO:7, SEQ ID NO:9, SEQ ID NO:11, SEQ ID NO:13, or SEQ ID NO:15 having the activity of producing a compound of SEQ ID NO:22. Testing for such activity is described above.

A polynucleotide of the present invention may be present in a vector. A vector is a replicating polynucleotide, such as a plasmid, phage, cosmid, or artificial chromosome, to which another polynucleotide may be attached so as to bring about the replication of the attached polynucleotide. When present in a vector, a polynucleotide of the invention may be referred to as a recombinant polynucleotide. As used herein, a "recombinant polynucleotide" refers to a polynucleotide having sequences that are not naturally joined together. The sequences may be joined by the artificial manipulation of different polynucleotide sequences using recombinant techniques, or may be chemically or enzymatically synthesized. A recombinant polynucleotide may be included in a suitable vector. Construction of vectors containing a polynucleotide of the invention employs standard ligation techniques known in the art. See, e.g., Sambrook et al, Molecular Cloning: A Laboratory Manual, Cold Spring Harbor Laboratory Press (1989).

A vector can provide for further cloning (amplification of the polynucleotide), i.e., a cloning vector, or for expression of the polypeptide encoded by the coding region, i.e., an expression vector. Suitable expression vectors include those that can be used to produce amounts of polypeptide, preferably a compound of the present invention that can be used in a composition of the present invention and, for instance, administered to a subject. Vectors may include a coding region encoding a polypeptide of the present invention or a fragment thereof. As used herein, a "coding region" refers to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end Selection of a vector depends upon a variety of desired characteristics in the resulting construct, such as a selection marker, vector replication rate, and the like. Suitable host cells for cloning or expressing the vectors herein are prokaryote or eukaryotic cells.

An expression vector optionally includes regulatory sequences operably linked to the coding region. A regulatory sequence is a nucleotide sequence that regulates expression of a coding region to which it is operably linked. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence. The invention is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell. As used herein, a "heterologous" regulatory sequence is a regulatory sequence operably linked to a coding region to which it is not normally operably linked.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

A vector may include more than one polynucleotide of the present invention. When more than one polynucleotide of the present invention is present in one vector, the polynucleotides may be organized in an operon, and operably linked to the same promoter located upstream of the first coding region in the operon. Alternatively, more than one promoter may drive expression of the polynucleotides. For instance, The vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence are sequences that confer resistance to kanamycin, ampicillin, chloramphenicol, tetracycline, neomycin, and eruthromycin.

Methods of Making

The present invention is also directed to methods for making compounds of the present invention. A method for producing a compound of the present invention may include growing a *Bifidobacterium* under conditions suitable for producing the compound. Typically, such conditions may include growing the *Bifidobacterium* on a surface. Suitable components that can be used for a solid medium include, but are not limited to, agar, gelatin, and gums such as alginate, xantham, and the like. The medium may be complete or minimal, preferably complete. Examples of suitable media include, but are not limited to, complex media that include a fermentable sugar, such as MRS, BLIM, and Brain Heart Infusion.

Bifidobacteria that may produce a compound of the present invention can be obtained from an individual, or laboratory strains can be used. Examples of bifidobacteria that may be used as a source of a compound of the present invention include *B. adolescentis, B. aerophilum, B. angulatum, B. animalis, B. asteroides, B. bifidum, B. boum, B. breve, B. catenulatum, B. choerinum, B. coryneforme, B. cuniculi, B. denticolens, B. dentium, B. gallicum, B. gallinarum, B. indicum, B. infantis, B. inopinatum, B. longum, B. magnum, B. merycicum, B. minimum, B. pseudocatenulatum, B. pseudolongum, B. psychraerophilum, B. pullorum, B. ruminantium, B. saeculare, B. scardovii, B. subtile, B. thermacidophilum,* and *B. thermophilum.* Preferably, the *Bifidobacerium* is *B. breve, B. infantis,* or *B. longum,* more preferably, *B. longum.*

Since bifidobacteria are believed to lose the ability to produce lantibiotics after prolonged in vitro culture in liquid medium, a *Bifidobacterium* is preferably obtained from an individual. Methods for obtaining a *Bifidobacterium* from an individual are routine and known in the art (see, for instance, Kullen et al., 1997, *FEMS Microbiol. Lett.,* 154:377-383; O'Suillivan, U.S. Pat. No. 6,746,672). For instance, fresh fecal samples may be collected from an individual and immediately homogenized in an appropriate amount of a sterile solution such as sterile peptone water (0.1%). Preferably, an individual has no history of gastrointestinal disorders and has not used antibiotics in the previous year. The homogenate may be transferred to an anaerobic chamber, where it may be serially diluted and plated on, for instance, BIM-25 (Muñoa et al., 1988, *Appl. Environ. Microbiol.,* 54:1715-1718). After anaerobic incubation at 37° C., red colonies can be randomly selected. The authenticity of the colonies appearing on the BIM-25 plates can be verified by routine methods, such as assessing the activity of fructose-6-phosphate phosphoketolase, a diagnostic enzyme for bifidobacteria, or by molecular analysis of the 16s rRNA gene or the recA gene as described by Kullen et al. (1997, *FEMS Microbiol Lett.,* 154:377-383).

Once a microbe such as a *Bifidobacterium* is growing in conditions that permit lantibiotic production it is expected to be able to continue to do so. However, a *Bifidobacterium* that produces a compound of the present invention should not be grown for extended periods under conditions that do not favor lantibiotic production, such as in broth, as they can loose the gene cluster encoding the compound. As the gene cluster also encodes the immunity genes, it cannot be lost if the lantibiotic is in the environment.

A *Bifidobacterium* can be screened to determine if it produces a compound of the present invention. Screening methods include culturing a *Bifidobacterium* under conditions suitable for expression of a lantibiotic and testing for the presence of a lantibiotic. Conditions that are "suitable" for an event to occur, or conditions that "allow" an event to occur, such as production of a lantibiotic by a *Bifidobacterium,* or "suitable" conditions are conditions that do not prevent such events from occurring. Thus, these conditions permit, enhance, facilitate, and/or are conducive to the event. Methods for determining whether a *Bifidobacterium* expresses a compound of the present invention are described above.

Screening methods may include determining if a *Bifidobacterium* has one or more of the polynucleotides involved in the synthesis of a compound of the present invention. For instance, the presence of a polynucleotide of the present invention can be determined by amplification. Preferably, a polynucleotide is amplified by the polymerase chain reaction (PCR). In PCR, a molar excess of a primer pair is added to a sample that includes polynucleotides from the test *Bifidobacterium,* preferably the chromosomal DNA. The primers are extended to form complementary primer extension products which act as templates for synthesizing the desired amplified polynucleotides. The presence of an amplified polynucleotide of the expected size indicates the test *Bifidobacterium* may produce a compound of the present invention.

Suitable polynucleotides that can be amplified include coding regions present in SEQ ID NOs: 1, 3, 5, 7, 9, 11, 13, and 15. Preferably, the polynucleotide amplified is a portion of the nucleotide sequence (SEQ ID NO:5) encoding the polypeptide SEQ ID NO:6. Primers that amplify a portion of a polynucleotide of the present invention can be designed using readily available computer programs, such as OMIGA program, (Oxford Molecular, Ltd., Oxford, UK). Factors that can be considered in designing primers include, but are not limited to, melting temperatures, primer length, size of the amplification product, and specificity. Primer length is generally between 15 and 30 nucleotides, but can be shorter or longer if desired. The conditions for amplifying a polynucleotide by PCR vary depending on the nucleotide sequence of primers used, and methods for determining such conditions are routine in the art. Examples of primer pairs include, for instance, LANR1-F (ATGAAGGCGATTCTGTTTC, SEQ ID NO:38) and LANR1-R (TCACAGCTCGATATTGGTG, SEQ ID NO:39), which result in an amplified product of 676 bp, and LANT1-F (GAGCATCAATGAGAAGTCC, SEQ ID NO:56) and LANT1-R (GCAATCAACACCAAAACC, SEQ ID NO:57), which result in an amplified product of 788 bp.

In another aspect the presence of a polynucleotide of the present invention can be determined with polynucleotide probes designed to hybridize to a polynucleotide present in the test *Bifidobacterium.* As used herein, "hybridizes," "hybridizing," and "hybridization" refers to noncovalent interaction forms between a probe and a target polynucleotide under standard conditions. Standard hybridizing conditions are those conditions that allow a probe to hybridize to a target polynucleotide. Such conditions are readily determined for a probe and the target polynucleotide using techniques well known to the art, for example see Sambrook et al. *Molecular Cloning: A Laboratory Manual,* Cold Spring Harbor Laboratory: New York (1989). Suitable polynucleotides that can be identified by hybridization include coding regions present in SEQ ID NOs: 1, 3, 5, 7, 9, 11, 13, and 15. Preferably, the polynucleotide identified by hybridization is the nucleotide sequence encoding the polypeptide SEQ ID NO:6. A probe may be less than 20 nucleotides, at least 20 nucleotides, at least 50 nucleotides, or at least 100 nucleotides in length.

In another aspect, a method for producing a compound of the present invention may include growing a microbe that includes a recombinant polynucleotide encoding a polypeptide that includes an amino acid sequence having structural similarity to SEQ ID NO:19, SEQ ID NO:20, SEQ ID NO:21, or SEQ ID NO:22, preferably SEQ ID NO:22. A microbe may include a coding region encoding a lanA of the present invention, and optionally may include a coding region encoding a lanR2 of the present invention, a lanK of the present invention, a lanR1 of the present invention, a lanD of the present invention, a lanM of the present invention, a lanI of the present invention, a lanT of the present invention, or a combination thereof. Preferably, microbe may include a coding region encoding SEQ ID NO:2, SEQ ID NO:4, SEQ ID NO:6, SEQ ID NO:8, SEQ ID NO:10, SEQ ID NO:12, SEQ ID NO:14, SEQ ID NO:16, or a combination thereof. A compound of the present invention may also be produced in vivo (Xie et al., 2004, Science, 303:679-681).

A microbe that includes a recombinant polynucleotide encoding a compound of the present invention may be an Archae, Eukarya or a Eubacteria, preferably a Eubacteria, such as a gram negative or a gram positive microbe. Examples of gram negative microbes include, but are not limited to, *E. coli* and *Salmonella* spp. Examples of gram positive microbes include, but are not limited to, *Bacillus* spp. such as *B. subtilis*, *Enterococcus* spp. such as *E. faecium*, *E. faecalis*, lactic acid bacteria such as *Lactococcus lactis*, *L. sakei*, and *Streptomyces*. Other microbes include yeast such as, but not limited to, *Saccharomyces cerevisiae* and *Pichia pastoris*.

A compound of the present invention may be isolated. For instance, a microbe producing a compound of the present invention, preferably a *Bifidobacterium*, can be grown in conditions suitable for the production of a lantibiotic, and the culture, including the medium, exposed to conditions suitable for isolating the compound. In one aspect, a compound of the present invention may be isolated by drying the cells and, optionally, the solid medium on which the cells are grown. Optionally, the culture may be further treated to sterilize it. For example, the culture can be treated by exposure to conditions to kill the bifidobacteria present in the culture. Examples of conditions useful for sterilization include heat or ultraviolet radiation. The culture may be dried until essentially all moisture is removed and a powder containing the compound remains. Methods for drying cultures are known to the art and include, for instance, spray drying, freeze drying, tunnel drying, vacuum drying, and air drying. The result of such methods is a mixture that includes a large number of components, including the compound of the present invention. Such a mixture may be added to food products. The mixture added to food products may be sterile.

In another aspect, a lantibiotic of the present invention may be isolated by methanol extraction. Additional methods may be used for further isolation and/or purification using methods known in the art for isolating and/or purifying lantibiotics. Such methods typically include, but are not limited to, column chromatography, including hydrophobic interaction chromatography, and high performance liquid chromatography (HPLC), such as reverse phase HPLC using, for instance, a C18 column. The optimum conditions to be used can be determined by routine experimentation. A purified compound of the present invention may be made using known synthetic chemistry techniques.

Compositions

The present invention also provides compositions. A composition may include a compound of the present invention. Such compositions may optionally include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration and not deleterious to a recipient thereof. The compound present in the composition may be isolated or purified. An isolated compound may be one that is isolated by drying the cells. Additional active compounds can also be incorporated into the compositions.

Compositions of the present invention may further include at least one component that damages the outer membrane of a gram negative microbe. For instance, a composition may include at least one chelator, preferably a metal chelator. The use of chelators such as ethylenediaminetetraacetic acid (EDTA) with lantibiotics is known to result in expanding the activity of some lantibiotics, such as nisin, from just gram positive microbes to include gram negative microbes (Blackburn et al., U.S. Pat. No. 5,691,301). The use of a chelator with a compound of the present invention is not required for the compound to be active against gram negative microbes. Examples of metal chelators include natural and synthetic compounds. Examples of natural compounds include plant phenolic compounds, such as flavonoids. Examples of flavinoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis(2-pyridylmethyl)-ethylene diamine. Examples of synthetic iron chelators include 2,2'-dipyridyl, 8-hydroxyquinoline, EDTA, ethylenediamine-di-O-hydroxyphenylacetic acid (EDDHA), desferrioxamine methanesulphonate (desferol), transferrin, lactoferrin, ovotransferrin, biological siderophores, such as xcatecholates and hydroxamates, and citric acid. Preferably, the chelator is EDTA.

Compositions of the present invention may further include at least one surfactant, preferably a non-ionic surfactant. Examples of non-ionic surfactants include glycerol monolaurate, sucrose esters such as sucrose palmitate, polysorbate 20, TRITON X-100, Isoceteth-20, ARLASOLVE 200L, Lauramine oxide, Decylpolyglucose, Phospholipid PTC, MEROXAPOL 105, and the like.

Compositions of the present invention may include other agents having bacteriostatic and/or bacteriocidal activity. Examples include, but are not limited to, lysostaphin, bacitracin, neomycin, polymixin, beta-lactams, including penicillin, methicillin, moxalactam and cephalosporins, such as cefaclor, cefadroxil, cefamandole nafate, cefazolin, cefixime, cefinetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone, cefuroxime, cephalexin, cephalosporin C, cepahlosporin C sodium salt, cephalothin, cephalothin sodium salt, cephalothin dihydrate, cephapirin, cephradine, cefuroximeaxetil, loracarbef, and the like, glycopeptides, anti-bacterial enzymes, including anti-staphylococcal enzymes such as mutanolysin, lysozyme or cellozyl muramidase, anti-bacterial antibodies, other anti-bacterial peptides such as defensins, and bacteriocins, including other lantibiotics such as nisin, subtilin, epidermin, cinnamycin, duramycin, ancovenin and Pep 5. In some aspects these agents may be particularly preferred when the composition is to be applied topically.

A composition may contain organic acids acceptable for use in food products or salts of these acids. A composition may contain individual acids or salts, or mixtures thereof. Preferred organic acids or salts for use in compositions include acetic acid, sodium acetate, sodium diacetate, potassium acetate, lactic acid, sodium lactate, potassium lactate, propionic acid, propionates, including, but not limited to, sodium propionate and potassium propionate, citric acid or its salts such as sodium citrate or potassium citrate, or combinations thereof.

A composition for administration to a subject may be prepared by methods known in the art of pharmacy. In general, a composition can be formulated in a dosage form to be compatible with its intended route of administration. Examples of routes of administration include, but are not limited to, perfusion; parenteral, e.g., intravenous, intradermal, intramuscular, subcutaneous; topical, e.g., mucosal (such as nasal, sublingual, vaginal, buccal, or rectal) and transdermal; otic; and oral. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, or phosphate buffered saline (PBS). A composition is typically sterile and, when suitable for injectable use, should be fluid to the extent that easy syringability exists. It should be stable under the conditions of manufacture and storage and optionally preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various optional antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (i.e., a compound of the present invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets or capsules, e.g., gelatin capsules. Oral compositions can also be prepared using a fluid carrier for use as a dentifrice. A dentifrice may be a liquid, paste, or powder, such as a mouthwash or a toothpaste. Pharmaceutically compatible binding agents may be included as part of the composition. The tablets, pills, capsules, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In another aspect, a composition may be a transgenic plant expressing a compound of the present invention.

For administration by inhalation, the active compounds may be delivered in the form of an aerosol spray from a pressured container or dispenser which contains a suitable propellant, e.g., a gas such as a hydrofluoroalkane, or a nebulizer.

For topical administration compositions of the invention may include various mixtures and combinations that can be applied topically and to permit even spreading and absorption into cutaneous and mucosal surfaces. Examples include sprays, mists, aerosols, lotions, creams, aqueous and non-aqueous solutions or liquids, oils, gels, powders, ointments, pastes, unguents, emulsions and suspensions. Topical formulations may be prepared by combining a compound of the present invention with conventional pharmaceutical or cosmeceutical diluents or carriers commonly used in topical dry, liquid, cream and aerosol formulations. Both liquids and powders can be delivered as sprays, mists or aerosols.

Powders may be formed with the aid of any suitable powder base, e.g., talc, lactose, starch, and the like. Solutions can be formulated with an aqueous or non-aqueous base, and can also include one or more dispersing agents, suspending agents, solubilizing agents, and the like. Topical gels may be prepared using polymers having a molecular weight and level of concentration effective to form a viscous solution or colloidal gel of an aqueous or non-aqueous solution or suspension of the active compound. Polymers from which topical gels may be prepared include polyphosphoesters, polyethylene glycols, high molecular weight poly(lactic) acids, hydroxypropyl celluloses, chitosan, polystyrene sulfonates, and the like.

Ointments, creams and lotions may be formulated, for example, with an aqueous or oily base and addition of a suitable thickening agent, gelling agent, stabilizing agent, emulsifying agent, dispersing agent, suspending agent, or consistency regulating agent, and the like. Bases include water, an alcohol or an oil, such as liquid paraffin, mineral oil, or a vegetable oil, such as peanut or castor oil. Thickening agents that can be used according to the nature of the base include soft paraffin, aluminum stearate, cetostearyl alcohol, propylene glycol, polyethylene glycols, polyphosphoesters, poly(lactic acids), hydroxyethyl celluloses, hydroxypropyl celluloses, cellulose gums, acrylate polymers, hydrophilic gelling agents, chitosan, polystyrene sulfonate, petrolatum, woolfat, hydrogenated lanolin, beeswax, and the like.

The ointments, pastes, creams, gels, and lotions can also contain excipients, such as animal and vegetable fats, oils, waxes, paraffins, starch, tragacanth, cellulose derivatives, polyethylene glycols, silicones, bentonites, silicic acid, talc, zinc oxide, and mixtures thereof. Powders and sprays can also contain excipients such as silicic acid, aluminum hydroxide, calcium silicates and polyamide powder, or mixtures of these substances. Solutions, suspensions or dispersions can be converted into aerosols or sprays by any of the known means routinely used for making aerosols for topical application. In general, such methods include pressurizing or providing a means of pressurizing a container of a solution, suspension or dispersion, usually with an inert carrier gas, and passing the pressured gas through a small orifice. Sprays and aerosols can also contain customary propellants, e.g., chlorofluorohydrocarbons or volatile unsubstituted hydrocarbons, such as butane and propane.

Excipients may include compounds that promote skin absorption, such as dimethyl sulfoxide (DMSO), partial glycerides of fatty acids, and the like. Examples of partial fatty acid glycerides include, but are not limited to IMWITOR 742 and IMWITOR 308. The topical formulations may also optionally include inactive ingredients to improve cosmetic acceptability, including but not limited to, humectants, surfactants, fragrances, coloring agents, emollients, fillers, and the like.

A composition may be administered directly by the dusting of a powder, spraying of an aerosol or by spreading a film of an ointment, cream, lotion, solution or gel to the desired area of the skin using the fingertips of the patient or a healthcare provider or other conventional application such as a swab or wipe. The product may be first applied to the skin and spread with the fingertips or an applicator or applied to the fingertips and spread over the skin. The compositions may also optionally first be coated on the surface of a topical applicator, such as a bandage, swab, moist woven or non-woven wipe and the like, which is then applied to the portion of the skin to receive the composition.

The active compounds can also be prepared in the form of suppositories (e.g., with conventional suppository bases such as cocoa butter and other glycerides) or retention enemas for rectal delivery.

The active compounds may be prepared with carriers that will protect the active compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. The materials can also be obtained commercially. Liposomal suspensions can also be used as pharmaceutically acceptable carriers. These can be prepared according to methods known to those skilled in the art.

Since the lantibiotic described in the examples is expressed by bifidobacteria while present in animals, it is expected the compounds of the present invention are safe and suitable for use in animals, including use in foods eaten by an animal. However, toxicity and therapeutic efficacy of such active compounds may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. Methods for evaluating the toxicity of lantibiotics are known in the art and are routine.

The data obtained from cell culture assays and animal studies can be used in formulating a range of dosage for use in animals, including humans. The dosage of such compounds lies preferably within a range of circulating concentrations that include the $ED_{50}$ with little or no toxicity. The dosage may vary within this range depending upon the dosage form employed and the route of administration utilized. For a compound used in the methods of the invention, the therapeutically effective dose can be estimated initially from cell culture assays. A dose may be formulated in animal models to achieve a concentration range that includes the $IC_{50}$ (i.e., the concentration of the test compound which achieves a half-maximal inhibition of signs) as determined in cell culture. Such information can be used to more accurately determine useful doses.

In those aspects where a composition is being administered to an animal for a pharmaceutical application or a personal care application, the composition can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a compound of the present invention can include a single treatment or, preferably, can include a series of treatments.

The present invention includes both patient-specific dosages forms, as well as non-patient-specific multi-dosage forms that can be used to decontaminate populations exposed to pathogens as a consequence of a bioterrorism attack.

A composition of the present invention may include a microbe, such as a *Bifidobacterium*, that expresses a compound of the present invention. A composition including a microbe that expresses a compound of the present invention may be encapsulated in, for example, a sugar matrix, a fat matrix, a polysaccharide matrix, or a protein matrix. It may also be coated and/or incorporated into tablet form. For instance, encapsulation, coating, and incorporation into tablet form may allow better survival of the microbe in the composition, or may allow better delivery of the microbe to the large intestine.

Such compositions that include a microbe that expresses a compound of the present invention are often orally administered to an animal. It is known in the art that bifidobacteria can be incorporated into different types of food products. In particular, the bifidobacteria of the present invention can be incorporated into solid and semi-solid dairy products, including fermented dairy products, for instance yogurt. Other examples of dairy products include cottage cheese, cheese, and powdered milk. Bifidobacteria can also be incorporated into baby foods. Beverages to which bifidobacteria can be added include milk, vegetable juice, fruit juice, soy milk, soybean milk, fermented soybean milk, and fruit flavored dairy beverages.

Methods of Use

The present invention is also directed to methods of using the compositions described herein. The methods include, for instance, pharmaceutical applications, food applications, personal care applications, and probiotic applications. The methods may include preventing microbial growth. The prevention of growth may be due to a bacteriostatic activity or a bacteriocidal activity of a compound of the present invention. The microbe may be gram positive or gram negative. Examples of gram positive microbes that may be sensitive to a lantibiotic of the present invention and inhibited include, but are not limited to, *Streptococcus* spp., such as *S. agalactiae*; *Enterococcus* spp., such as *E. faecalis* and *E. faecium*; *Bacillus* spp., such as *B. anthracis, B. cereus, B. coagulans*, and *B. licheniformis*; *Listeria* spp., such as *L. monocytogenes*; *Staphylococcus* spp., such as *S. aureus*; *Streptococcus* spp., such as *S. agalactiae, S. mutans, S. viridans, S. thermophilus, S. constellatus*, and *S. zooepidemicus*; *Clostridium* spp., such as *C. botulinum, C. difficile, C. perfringens, C. sordellii, C. tetani, C. sordellii, C. sporogenes, C. tyrobutyricum*, and *C. putrefasciens*; *Actinomyces* spp., such as *A. israelii* and *A. naeslundii*; *Leuconostoc* spp.; *Lactobacillus* spp.; *Micrococcus* spp., *Mycobacterium* spp., *Corynebacterium* spp., *Propionibacterium* spp., *Pediococcus* spp., *Peptostreptococcus* spp., *Sporolactobacillus* spp., *Brevibacterium* spp., and *Sporolactobacillus* spp.

Examples of gram negative microbes that may be sensitive to a lantibiotic of the present invention and inhibited include, but are not limited to, members of the family Enterobacteriaceae, such as *Citrobacter* spp., *Edwardsiella* spp., *Enterobacter* spp., *Erwinia* spp., *Escherichia*, such as *E. coli* (e.g., H7:O157), *Ewingella* spp., *Klebsiella*, such as *K. pneumoniae* spp., *Plesiomonas*, such as *P. shigelloides* spp., *Proteus*, such as *P. vulgaris* spp., *Providencia* spp., *Salmonella* spp., *Serratia*, such as *S. marcescens* spp., *Shigella* spp., and *Yers-*

*inia*, such as *Y. enterocolitica* and *Y. pestis*; members of the family Vibrionaceae, such as *Vibrio alginolyticus, V. cholerae, V. parahaemolyticus,* and *V. vulnificus*; and members of the family Pseudomonadaceae, such as *Pseudomonas aeruginosa, P. anguilliseptica, P. oryzihabitans, P. plecoglossicida, P. fluorescens* and *P. syringae*. Other examples of gram negative microbes that may be inhibited include, but are not limited to, *Helicobacter pylori; Camplyobacter* spp., such as *C. jejuni, C. coli,* and *C. upsaliensis; Bacteroides* spp., such as *B. frgilis; Fusobacaterium* spp., such as *F. necrophorum, F. ulcercans, F. russi,* and *F. varium; Leptospira* spp.; *Pectobacterium* spp., such as *P. carotovorum; Pasteurella* spp., such as *P. multocida, Borrelia* spp., *Legionella* spp., *Neissaria* spp., *Fusobacterium* spp., and *Agrobacterium* spp.

Pharmaceutical and personal care applications include, for instance, methods of treating an animal to inhibit, preferably prevent microbial growth. As used herein, "treatment" and "treating" refer to the use of a composition of the present invention to prevent, cure, retard, or reduce the severity of signs in a subject resulting from the presence of a microbe, and/or result in no worsening of signs over a specified period of time in an subject which has already been exposed to a microbe that can cause the signs. Treatment may be prophylactic or, alternatively, may be initiated after the exposure of an animal to a microbe. Prophylactic treatment refers to the use of a composition of the present invention to inhibit, preferably prevent microbial growth, thereby preventing or reducing signs of a condition if the subject is later exposed to a microbe. Treatment that is prophylactic, for instance, initiated before a subject manifests signs of a condition, is referred to herein as treatment of a subject that is "at risk" of developing a condition. Treatment initiated after the exposure of a subject to a microbe causing a condition may result in decreasing the severity of the signs, or completely removing the signs.

As used herein, the term "signs" refers to objective evidence in a subject of a condition caused by the presence of a microbe. Signs can vary depending upon the microbe. Signs of conditions caused by the presence of a microbe and the evaluation of such signs are routine and known in the art. Accordingly, the present invention is also directed to methods for treating a microbial infection in an animal, and methods for treating a condition caused by a microbe. As used herein, a "microbial infection" refers to a detrimental colonization of an animal by a microbe.

The methods include administering an effective amount of the composition of the present invention to an animal having an infection and/or signs of a condition caused by a microbe, and determining whether the infection and/or signs of the condition have decreased. Conditions include, but are not limited to, wound infections, halitosis, caries, systemic infections, and skin infections.

The methods may include administering a composition of the present invention to an animal. The animal may be any animal susceptible to a condition caused by a microbe including, but not limited to, a vertebrate, more preferably a mammal, or an avian. Examples of mammals include, but are not limited to, a human; a member of the subfamily Bovinae, such as cattle and bison; a member of the subfamily Caprinae, such as sheep and goats; a member of the genus *Sus*, such as pigs and hogs; companion animals, such as cats and dogs; and a member of the genus *Equus*, such as horses and donkeys. Examples of birds include, but are not limited to, domesticated birds such as turkeys, chickens, ducks, and geese. Another example of a vertebrate is a fish. A composition of the present invention may be delivered to an animal by methods described herein and known in the art, thereby providing an effective amount to the animal. In this aspect of the invention, an "effective amount" is an amount effective to inhibit growth of a microbe, prevent the manifestation of signs of the condition, decrease the severity of the signs of the condition, and/or complete remove the signs. It is not required that any composition of the present invention completely inhibit growth of all microbes, or completely cure or eliminate all signs of a condition being treated.

Food applications include, for instance, food preservation by inhibiting microbes that spoil food. The term "food" or "food product" encompasses all edible nutritive substances and compositions, including those intended for human consumption as well as consumption by, for instance, livestock. "Food" and "food product" includes unprocessed, as well as processed, e.g., cooked, nutritive substances and compositions, such as beverages. The expression "present in food" refers to portions of a food that may be resident to harmful bacteria, such as external surfaces, interior surfaces, or the combination thereof.

A composition of the present invention may be used in connection with a food product that is susceptible to bacterial growth or degradation. These include, but are not limited to, dairy foods, fruits and vegetables, fruit and vegetable derived products, grains and grain derived products, meats, poultry, and seafood. Examples of dairy foods include, but are not limited to, cheese, milk, cream, and fermented dairy foods such as yogurt. Examples of meats include, for instance, ham, beef, salami, chicken, and turkey, including whole parts or processed meat products made therefrom. Other food products include processed food products including ready to eat meals, entrees, and meats, deli salads, mayonnaise, dressings (including salad dressings), sauces and condiments, pastas, soups, edible oils, fish and fish products, egg products, beverages, aseptically packaged foods, as well as mixtures of the foregoing.

A composition of the present invention may be used by mixing with and/or applying on a blendable food product, but may be applied to a surface of solid food products by a dip, rinse, or spray, or by application to the interior of such products, e.g. by injection. The composition may be applied as a marinade, breading, seasoning rub, glaze, colorant mixture, and the like, or as an ingredient to be mixed with and incorporated into the food product, In still other aspects, the composition may be indirectly placed into contact with the food surface by applying the composition to food packaging materials, such as a casing or a film, and thereafter applying the packaging to the food surface such that the composition comes into contact with the external food surface. The optimum amount to be used will depend upon the particular food product to be treated and the method used to apply the composition to the food and/or the food surface, but can be determined by routine experimentation.

Probiotic applications of compositions of the present invention include, for instance, use of a microbe, preferably a *Bifidobacterium*, expressing a compound of the present invention, as a dietary supplement or as a food ingredient. The uses of bifidobacteria as dietary supplements is known in the art and routine. Typically, a *Bifidobacterium* expressing a compound of the present invention is administered to an animal in need thereof. The *Bifidobacterium* can be administered as a biologically pure culture, or as a mixed culture. As used herein, a "mixed" culture is one containing a *Bifidobacterium* and at least one other microbe, preferably a prokaryotic microbe, more preferably a second *Bifidobacterium*.

One method of the present invention provides inhibiting the replication of microbes in the gastrointestinal tract, preferably the large intestine, of an animal by administering to an animal a *Bifidobacterium* that expresses a compound of the present invention. The method may include measuring the presence in the gastrointestinal tract of the microbe to be inhibited, where a decrease in the presence of the microbe in the animal after administration of the *Bifidobacterium* indicates inhibition of the replication of the microbe in the gastrointestinal tract of the animal.

The types of microbes whose replication can be inhibited include those present in the gastrointestinal tract of an animal when the *Bifidobacterium* is administered, and microbes that are introduced to the gastrointestinal tract after the *Bifidobacterium* is administered. Thus, a *Bifidobacterium* expressing a compound of the present invention can also be used in a method for inhibiting the establishment of a microbe in the gastrointestinal tract of an animal.

Another probiotic application includes methods for establishing a *Bifidobacterium* flora in an animal. Such a flora is expected to competitively inhibit the ability of other microbes to establish themselves as a flora in the gastrointestinal tract. The method includes administering to an animal a *Bifidobacterium* that expresses a compound of the present invention. The method also includes measuring the presence in the gastrointestinal tract of the *Bifidobacterium* over a period of time following the administration. A *Bifidobacterium* flora is considered to be established in an animal when there is at least about $10^6$ of the *Bifidobacterium* present per gram of feces. Preferably, the animal is an adolescent or adult human or an infant, including an immature, premature, or mature infant. The present method can be used to establish a *Bifidobacterium* flora in a healthy human, and in humans that have had their normal intestinal flora modified by, for instance, diarrhea or by drug treatment including antibiotic therapy or chemotherapy.

The present invention is illustrated by the following examples. It is to be understood that the particular examples, materials, amounts, and procedures are to be interpreted broadly in accordance with the scope and spirit of the invention as set forth herein.

EXAMPLES

Example 1

Bifidobacteria are frequently proposed to be associated with good intestinal health primarily because of their overriding dominance in the feces of breast fed infants. However, clinical feeding studies with exogenous bifidobacteria show they don't remain in the intestine, suggesting they may lose competitive fitness when grown outside the gut.

To further the understanding of genetic attenuation that may be occurring in bifidobacteria cultures, we obtained the complete genome sequence of an intestinal isolate, *Bifidobacterium longum* DJO10A that was minimally cultured in the laboratory (less than 20 generations), and compared it to that of a culture collection strain, *B. longum* NCC2705. This comparison revealed colinear genomes that exhibited high sequence identity, except for the presence of 17 unique DNA regions in strain DJO10A and six in strain NCC2705. While the majority of these unique regions encoded proteins of diverse function, eight from the DJO10A genome and one from NCC2705, encoded gene clusters predicted to be involved in diverse traits pertinent to the human intestinal environment, specifically oligosaccharide and polyol utilization, arsenic resistance and lantibiotic production. Seven of these unique regions were suggested by a base deviation index analysis to have been precisely deleted from strain NCC2705 and this is substantiated by a DNA remnant from within one of the regions still remaining in the genome of NCC2705 at the same locus. This targeted loss of genomic regions was experimentally validated when growth of the intestinal *B. longum* in the laboratory for 1,000 generations resulted in two large deletions, one in a lantibiotic encoding region, analogous to a predicted deletion event for NCC2705. A simulated fecal growth study showed a significant reduced competitive ability of this deletion strain against *Clostridium difficile* and *E. coli*. The deleted region was between two IS30 elements which were experimentally demonstrated to be hyperactive within the genome. The other deleted region bordered a novel class of mobile elements, termed mobile integrase cassettes (MIC) substantiating the likely role of these elements in genome deletion events.

Deletion of genomic regions, often facilitated by mobile elements, allows bifidobacteria to adapt to fermentation environments in a very rapid manner (2 genome deletions per 1,000 generations) and the concomitant loss of possible competitive abilities in the gut.

Results and Discussion

Genomic sequencing of a minimally cultured *B. longum* strain. The power of comparative genomics can provide insights into features that are important for a species to survive and compete in its habitat. The genome sequence of the culture collection strain, *B. longum* NCC2705 (Schell et al., 2002, *Proc Natl Acad Sci USA*, 99:14422-14427, is available and the ability to compare this genome with one from a strain that was deliberately minimally cultured in vitro may provide new insights to features that may be important for this prominent species from the human large gut. Newly isolated and minimally cultured *B. longum* strains were characterized and strain DJO10A was selected based on its prominent ability to bacteriostatically inhibit other bacteria through the production of siderophores (O'Sullivan, U.S. Pat. No. 6,746,672), a characteristic that appeared attenuated in all culture collection and commercial bifidobacteria analyzed. It was therefore selected for genomic sequencing as an isolate that likely had minimal attenuation from its origin in the intestine. The complete genome sequence of this strain was deciphered and consisted of one circular chromosome and two cryptic plasmids, pDOJH10L and pDOJH10S that were described previously (Lee and O'Sullivan, 2006, *Appl Environ Microbiol* 2006, 72:527-535).

General characteristics of the *B. longum* DJO10A genome. The chromosome of *B. longum* DJO10A contained 2,375,792 bp, with 60.15% G+C content and 1,990 encoded genes containing four rRNA operons, 58 tRNAs, 6 insertion sequence (IS) families as well as one prophage (Table 1). Its genomic characteristics were analogous to strain NCC2705, except it contained an extra tRNA_Ser: GCT encoded on its prophage (Ventura et al, 2005, *Appl Environ Microbiol* 2005, 71:8692-8705). Codon usage analysis showed that this tRNA is the most frequently used tRNA_Ser in the prophage, while it is not the most used tRNA_Ser for the *B. longum* DJO10A genome (Table 2), pointing to an evolutionary selective pressure for its presence on the prophage. While both genomes contained tRNA's for every amino acid, the corresponding genes for aminoacyl-tRNA synthetases for both asparagine and glutamine are missing, suggesting a reliance on alternative pathways for translation with these amino acids, similar to many other bacteria (Skouloubris et al. 2003, *Proc Natl Acad Sci USA* 2003, 100:11297-11302, Min et al., 2002, *Proc Natl Acad Sci USA* 2002, 99:2678-2683). Both these alternative pathways involve gatABC, which is present in both genomes as well as gltX and aspS involved in the glutamine and asparagine alternative translation pathways respectively, substantiating this proposed translation route. Interestingly, the *B. longum* genome contains novel mobile integrase cassettes (MIC) consisting of three different contiguous integrases flanked by an inverted repeat and a palindrome structure sandwiched by two IS3-type IS elements (FIG. 1). Analysis of the genome of *B. longum* NCC2705 revealed three analogous MIC elements, located in a non-linear fashion relative to strain DJO10A indicating these elements are indeed mobile (FIG. 9). Interestingly, analysis of the genome sequences of another *Bifidobacterium* species, *B. adolescentis* (GeneBank AP009256), as well as other intestinal bacteria, *Bacteroides* (AE015928), *Lactobacillus* (CP000033), and *E. coli* (U00096), did not reveal MIC elements, suggesting these structures may be unique to a subset of closely related bifidobacteria.

TABLE 1

Overall characteristics of the genomes of
*B. longum* strains DJO10A and NCC2705.

| | DJO10A | NCC2705 |
|---|---|---|
| Size of chromosome (bp) | 2,375,792 | 2,256,640 |
| Overall G + C % | 60.15 | 60.12 |
| Number of plasmids | 2 (10 and 3.6 kb) | 1 (3.6 kb) |
| Genes | | |
| Total genes | 1990 | 1727 |
| Average gene length (bp) | 1031 | 1115 |
| Gene density (genes/kb) | 0.838 | 0.765 |
| Gene coding percentage (%) | 86.4 | 85.3 |
| Gene G + C % | 61.13 | 60.86 |
| Unique Sequences | | |
| Strain-specific unique genes | 269 | 117 |
| Number of unique regions[a] | 17 | 6 |
| Number of genes in unique regions | 218 | 84 |
| Prophage | 1 | 1 |
| Number of genes in prophage region | 57 | 19 |
| RNAs and Repeat Sequences | | |
| rRNA operons | 4 | 4 |
| tRNAs | 58 | 57 |
| Tandem repeats | 22 | 23 |
| Mobile Elements[b] | | |
| Mobile integrase cassette (MIC) | 4 | 3 |
| IS3 family | 13 | 14 |
| IS21 family | 10 | 7 |
| IS30 family | 9 | 5 |
| IS256 family | 4 | 7 |
| ISL3 family | 7 | 12 |
| IS200/605 family | 1 | 1 |

[a] refers to unique regions that encode functional or hypothetical genes in DNA regions >3 kb;
[b] includes fragmented elements

TABLE 2

Comparison of serine codon usage between chromosomal
and prophage genes in strain DJO10A.

| Amino acid | Codon | Non-prophage genes | | Prophage genes | |
|---|---|---|---|---|---|
| | | Number | Frequency | Number | Frequency |
| Serine | UCU | 2416 | 0.35 | 20 | 0.18 |
| | UCC[a] | 16802 | 2.45 | 169 | 1.53 |
| | UCA | 2277 | 0.33 | 33 | 0.30 |
| | UCG | 9031 | 1.32 | 97 | 0.88 |
| | AGU | 1837 | 0.27 | 19 | 0.17 |
| | AGC[b] | 8769 | 1.28 | 324 | 2.94 |

[a] bold indicates the most frequent codon;
[b] AGC is compatible to the extra tRNA_Ser in the prophage genome.

Organization of the origin and terminus of replication. An oriC and terC were found in identical locations in the genome of strain DJO10A and the updated genome sequence of strain NCC2705 (FIG. 9). These regions are extremely highly conserved in both genomes (>99.9% identity) and consist of three oriC clusters and a terC, which is consistent with the predicted replication regions from other bacterial genomes (Mackiewicz et al., 2004, *Nucleic Acids Res* 2004, 32:3781-3791). However, the location of the observed oriC region in both genomes is slightly different from the predicted location based on genome asymmetry, a feature that has previously been seen in the *Helicobacter pylori* 26695 genome (Mackiewicz et al., 2004, *Nucleic Acids Res* 2004, 32:3781-3791, Zawilak et al., 2001, *Nucleic Acids Res* 2001, 29:2251-2259). As well as the multiple oriC clusters, there are 7 different types of DnaA boxes, consistent with the majority of sequenced genomes and are proposed to be involved in controlling initiation of chromosome replication (Mackiewicz et al., 2004, *Nucleic Acids Res* 2004, 32:3781-3791).

Figure 10:
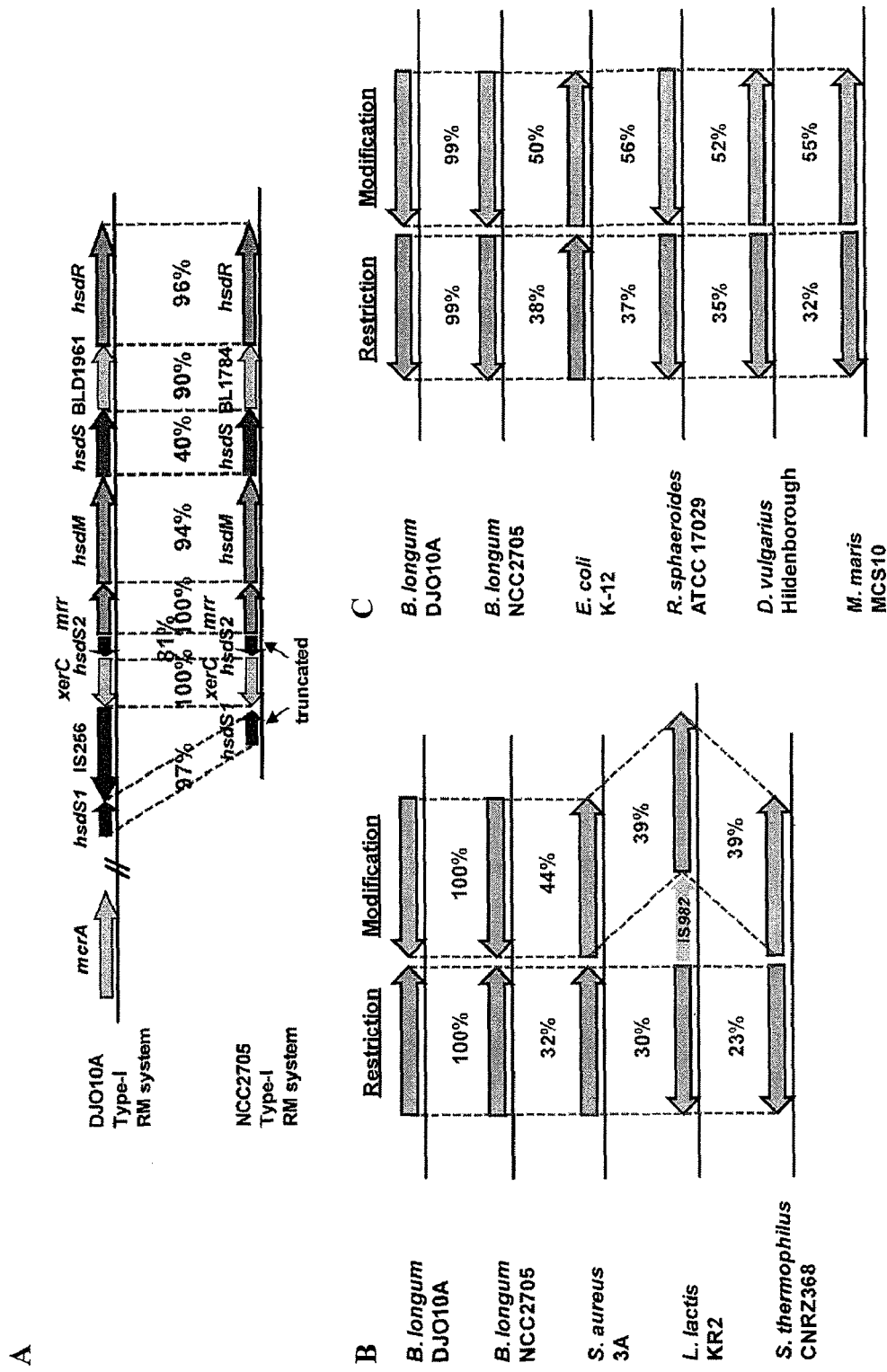
FIG. 10. Type I and II restriction modification (R-M) systems encoded by the *B. longum* genomes. (A) Alignment of the genomic locations encoding a type I R-M system between *B. longum* DJO10 and NCC2705. (B) Comparison of a Sau3AI-type II R-M system (recognition site, 5'-GATC-3') with analogous R-M systems in other bacteria and (C) comparison of a EcoRII-type II R-M system (recognition site, 5'-CCWGG-3') with analogous R-M systems in other bacteria. Percentage protein sequence identities compared to *B. longum* DJO10A are indicated.

Restriction and modification (R-M) systems. The protective role that R-M systems impart on bacteria has been compared to the immune system of higher organisms (Price and Bickle, 1986, *Microbiol Sci* 1986, 3:296-299). The presence of these systems in numerous bacteria demonstrates their important role for bacterial survival in nature. Both of the *B. longum* genomes encode type I and two type II R-M systems that are highly conserved (FIG. 10). They also contain an Mrr system that is predicted to restrict methylated DNA (usually HhaII or PstI methylated DNA) that is 100% conserved between both strains (FIG. 10A). The clustering of Mrr with the type I R-M system is similar to *E. coli* K12 (GenBank U00096). The low identity (40%) between the HsdS proteins in the two strains likely reflects the independent evolution of this type I R-M system in these strains following their evolutionary divergence, as these systems evolve by changing their specificity components (HsdS) to enable it to recognize different sequences. This is substantiated by the existence of an hsdS gene that was inactivated by an IS256 insertion event and both parts of this disrupted gene exhibit much higher conservation, suggesting the insertion event occurred before their evolutionary divergence (FIG. 10A). Upstream from this locus in strain DJO10A there is another restriction gene, McrA (restricts DNA methylated by HpaII or SssI), that is not present in NCC2705. The conserved type II R-M systems in both strains are isoschizomers of Sau3AI and EcoRII which restrict DNA at very frequently occurring sites (FIGS. 10B and 10C). This, together with the range of restriction systems present, may be a factor in limiting the incursion of foreign DNA into these bacteria thus explaining the very low electroporation frequencies reported for bifidobacteria to date.

Unique genome regions in the *B. longum* strains. Alignment of the genome sequence of *B. longum* DJO10A with that of strain NCC2705 illustrates that they are highly conserved and collinear, except for the mobile IS and MIC elements (FIG. 9). There is also an apparent genome reduction in strain NCC2705, consistent with previous observations for microbes growing in a stable environment without horizontal gene transfer opportunities and redundant genes accumulating mutations before subsequent deletion (Nilsson et al., 2005, *Proc Natl Acad Sci USA* 2005, 102:12112-12116). There are 248 unique sequences of >10 bp between the two genomes, with the majority of them being short and encoding few if any genes. This high number of unique sequences between the two strains was surprising given that the genomes of a clinical isolate of *Mycobacterium tuberculosis* and one that was extensively passaged for decades in the laboratory display only 86 of such regions in genomes twice the size (Fleischmann et al., 2002, *J Bacteriol* 2002, 184: 5479-5490). There are 23 larger unique regions that encode functional or hypothetical genes and range in size from 3.0 to 48.6 kb, with 17 of these unique regions present in strain DJO10A encoding 219 predicted genes, and 6 unique regions in NCC2705 encoding 84 genes (FIG. 2A). These unique regions are not clustered around the oriC and terC which have previously been associated with regions of intraspecies variation (Berger et al, 2007, *J Bacteriol* 2007, 189:1311-1321, Molenaar et al., 2005, *J Bacteriol* 2005, 187:6119-6127).

One unique region in each genome corresponds to a prophage. The prophage in strain NCC2705, which is truncated, appears to be a longtime resident of the genome as it does not correspond with a Base Deviation Index (BDI) peak (FIG. 2A), as this analysis predicts recent horizontal gene transfer (HGT) events. This appears to have been replaced in the genome of strain DJO10A with a different prophage, that is complete and inducible (Lee and O'Sullivan, 2006, *Appl Environ Microbiol* 2006, 72:527-535) and corresponds with a significant BDI peak substantiating this recent HGT event. The other five unique regions in strain NCC2705 contain largely hypothetical genes or genes of diverse functions without any significant gene clusters. However one of these regions (unique region 4') does encode putative xylan degradation genes, which is a function predicted to be important for competition in the large intestine. As this region corresponds to a BDI peak, it suggests it may be a recent acquisition by this strain and its evolution in the large intestine would provide the selective pressure for acquiring this unique region. Of the other 16 unique regions in the strain DJO10A, eight encode significant gene clusters involved in functions predicted to be important for competition in the large intestine, specifically oligosaccharide and polyol utilization, arsenic resistance and lantibiotic production.

Figure 3:
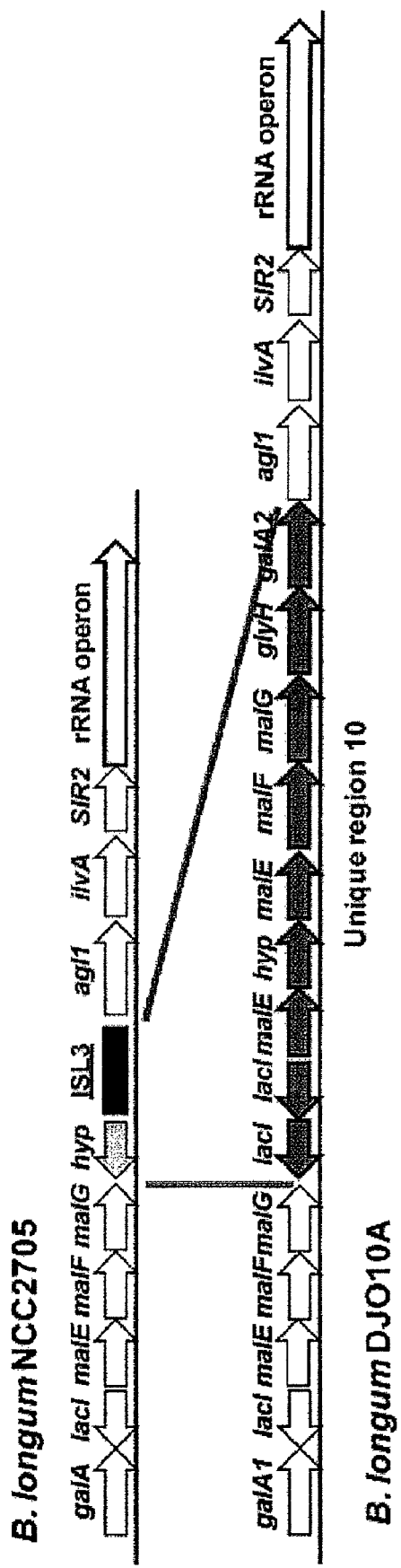
FIG. 3. Comparison of oligosaccharide utilization gene cluster 7 between two *B. longum* genomes. DJO10A-unique genes in unique region 10 are colored dark grey, ISL3-type IS element is colored black and other matched genes are colored white. galA, α-galactosidase; lacI, LacI-type repressor; malEFG, ABC-type transport system; ISL3, ISL3-type IS element; agl1, glycosidase; ilvA, threonine dehydratase; SIR2, NAD-dependent protein deacetylase; glyH, glycosyl hydrolase; hyp, hypothetical protein.
Figure 11:
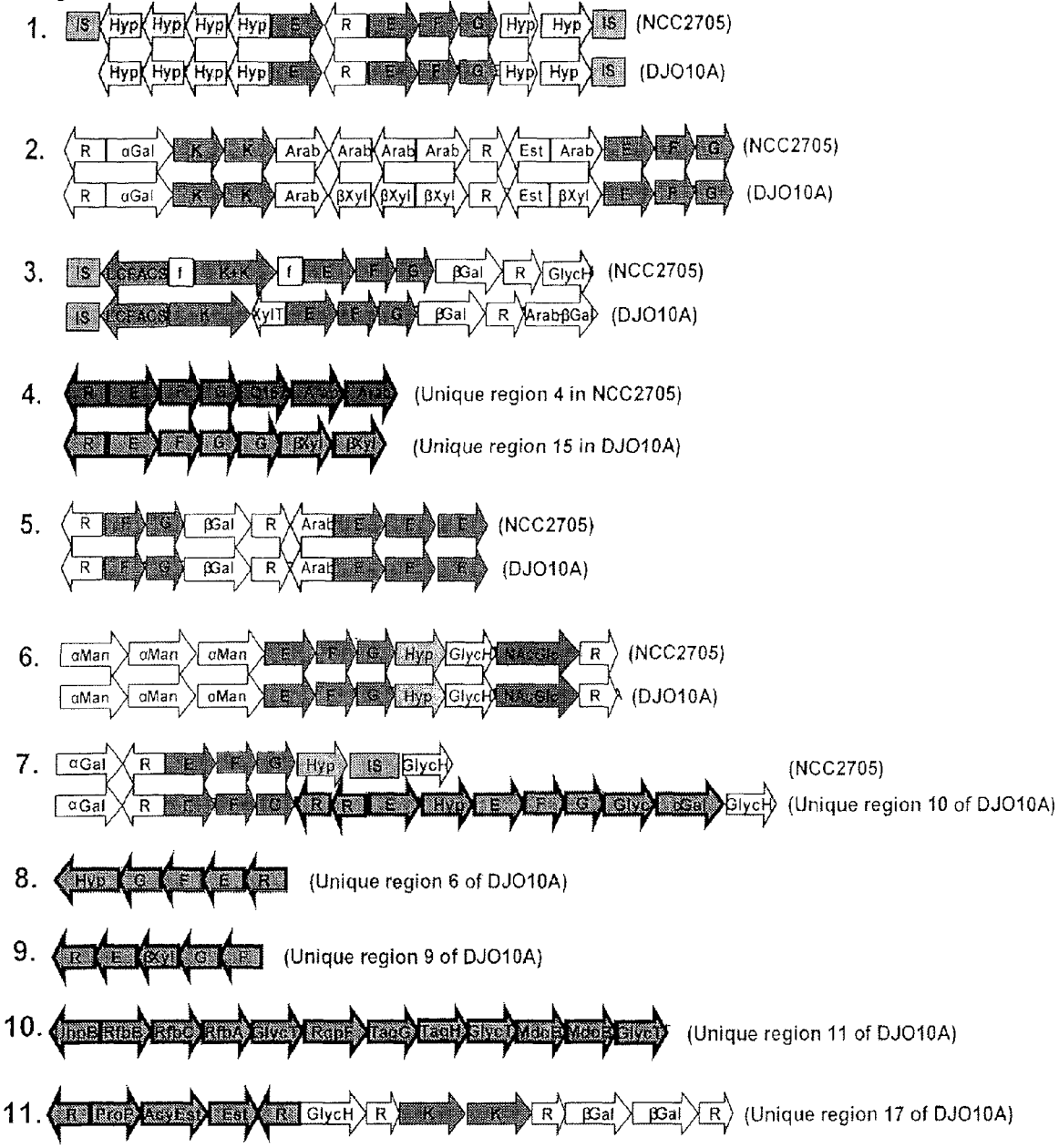
FIG. 11. Organization of the 11 different types of oligosaccharide utilization gene clusters (11 in DJO10A and 7 in NCC2705). Unique genes of strain DJO10A are indicated. IS, insertion sequence; Hyp, hypothetical protein; Arab, arabinosidase; E, malE; F, malF; G, malG; R, lacI-type repressor; K, ATPase of ABC transporter; αGal, α-galactosidase; βXy1, β-xylosidase; Est, esterase; LCFACS, long-chain fatty acid acetyl CoA synthetase; f, fragmented gene; Xy1T, D-xylose proton symporter; βGal, β-galactosidase; Arab-βGal, arabinogalactan endo-1,4-β-galactosidase; O157, ORF with homolog only in *E. coli* O157; αMan, α-mannosidase; GlycH, glycosyl hydrolase; NAc-Glc, N-acetyl glucosaminidase; UhpB, histidine kinase; RfbA, dTDP-glucose pyrophosphorylase; RfbB, dTDP-D-glucose 4,6-dehydratase; RfbC, dTDP-4-dehydrorhamnose 3,5-epimerase; RgpF, lipopolysaccharide biosynthesis protein; TagG, ABC-type polysaccharide/polyol phosphate export systems, permease component; TagH, ABC-type polysaccharide/polyol phosphate transport system, ATPase component; MdoB, phosphoglycerol transferase; ProP, permease; Acyl-Est, acyl esterase. It should be noted that the glycosyl hydrolase gene in cluster 7 was annotated as isomaltase in the NCC2705 genome annotation.

Oligosaccharide and polyol utilization. According to a COG functional classification (Tatusov et al., 2000, *Nucleic Acids Res* 2000, 28:33-36), the highest number of unique genes in strain DJO10A with a predicted function belongs to the carbohydrate metabolism [G] category (Table 3). Interestingly, most of the unique genes in the carbohydrate metabolism category are involved in oligosaccharide utilization, which is the major carbohydrate source available to microbes in the large intestine. In all there are 11 oligosaccharide utilization gene clusters in strain DJO10A, of which 5 are fully present and 2 are partially present in strain NCC2705 (FIG. 11). It is noteworthy that one of these clusters (Cluster 7 in FIG. 11) contains an ISL3 element in the NCC2705 genome at the precise location of the extra oligosaccharide utilization genes in strain DJO10A (FIG. 3). A BDI analysis suggested that the extra oligosaccharide gene clusters in strain DJO10A were not acquired following evolutionary divergence from strain NCC2705, as neither corresponds with a BDI peak (FIG. 2A). The majority of BDI peaks suggesting recent HGT events were the same in both genomes substantiating this analysis. This would suggest the six unique regions 6, 9, 10, 11, 15 and 17 encoding oligosaccharide utilization genes were likely lost from strain NCC2705 during its adaptation to a fermentation environment. Further evidence for the loss of these unique regions from strain NCC2705 comes from a DNA remnant of 361 bp (98% identity) from the ushA gene within the unique region 1 that was left remaining at this locus in NCC2705 (FIG. 2B).

TABLE 3

COG categories for all genes in both *B. longum* genomes.

| Function class | Individual function categories | *B. longum* DJO10A | *B. longum* NCC2705 |
|---|---|---|---|
| Information | J: Translation, ribosomal structure and biogenesis | 133 (2)[a] | 130 |
|  | K: Transcription | 129 (18) | 115 (9) |
|  | L: DNA replication, recombination, and repair | 150 (20) | 96 (1) |
| Cellular processes | D: Cell division and chromosome partitioning | 22 (2) | 23 (1) |
|  | V: Defense mechanisms | 48 (5) | 48 (3) |
|  | O: Posttranslational modification, protein turnover | 51 (2) | 50 (2) |
|  | M: Cell envelope biogenesis, outer membrane | 68 (8) | 67 (10) |
|  | P: Inorganic ion transport and metabolism | 56 (2) | 54 |
|  | U: Intracellular trafficking, secretion | 16 (1) | 14 |
|  | N: Cell motility | 3 | 4 |
|  | T: Signal transduction mechanisms | 53 (6) | 41 (1) |
| Metabolism | F: Nucleotide transport and metabolism | 70 (2) | 65 (1) |
|  | G: Carbohydrate transport and metabolism | 188 (32) | 167 (7) |
|  | E: Amino acid transport and metabolism | 171 (6) | 153 |
|  | H: Coenzyme metabolism | 44 | 44 (1) |
|  | I: Lipid metabolism | 41 (1) | 36 (1) |
|  | C: Energy production and conversion | 50 (1) | 50 (2) |
|  | Q: Secondary metabolites transport and metabolism | 6 | 4 |
| Poorly characterized | R: General function prediction only | 167 (20) | 161 (15) |
|  | S: Function unknown | 525 (142) | 405 (63) |
| Total |  | 1991 (270) | 1727 (117) |

Figure 4:
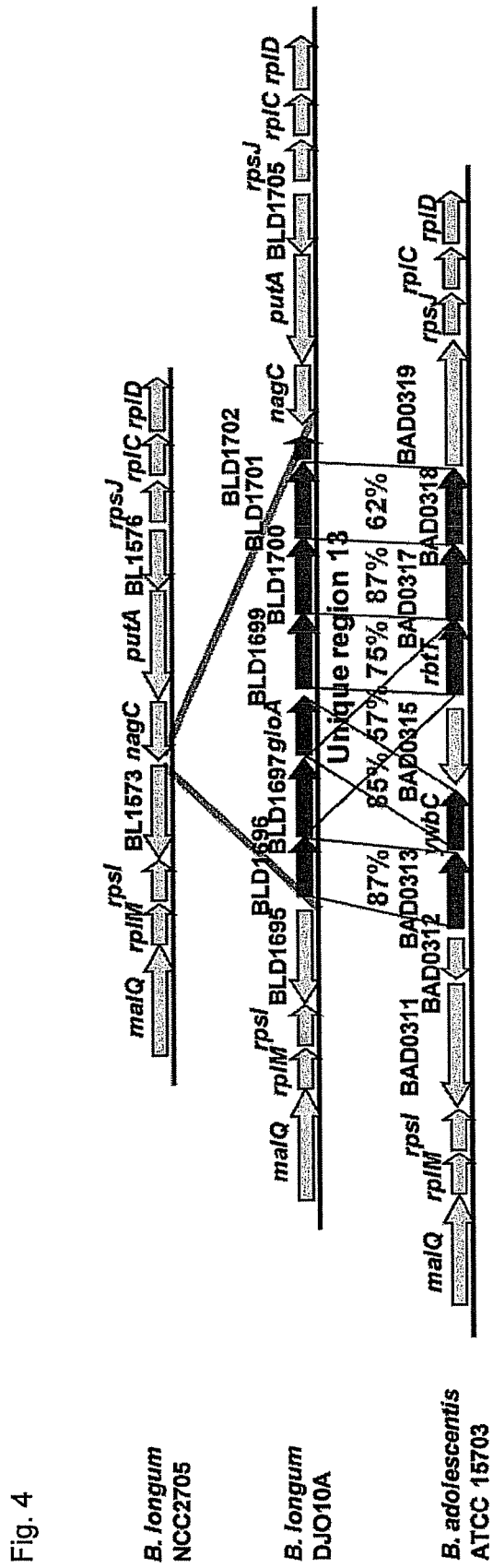
FIG. 4. Organization of genes involved in polyol metabolism in the unique region 13 in strain DJO10A and comparison with an analogous region in *B. adolescentis* ATCC 15703. Amino acid identities are indicated between homologous genes. ORFs shaded black are from unique region 13 and corresponding homologs in *B. adolescentis* ATCC 15703.

[a]refers to the number of genes in the unique regions of each genome as defined in the text Polyols are not digestible by humans and their metabolism is believed to be important for bacterial competition in the human large intestine and their ingestion has been implicated in increased bifidobacteria numbers (Gostner et al., 2006, *Br J Nutr,* 95:40-50.). While strain NCC2705 does not contain genes involved in polyol metabolism, unique region 13 of strain DJO10A is dedicated to this (FIG. 4), containing genes involved in polyol recognition, transport and dehydration, and there are also some polyol metabolism genes in unique region 11. Given that unique region 13 does coincide with a BDI peak (FIG. 2A), it may represent gene acquisition by strain DJO10A. Interestingly, a similar polyol locus was found in *B. adolescentis* ATCC 15703 at a similar genome location (FIG. 4).

Arsenic resistance. Other unique regions in strain DJO10A encode gene clusters predicted to be involved in characteristics that would be important for survival and competition in the human intestine. Two operons encoding ATP-dependent arsenic resistance genes are in unique regions 5 and 7 and may be important for intestinal survival as the human intestine contains low concentrations of arsenic from the diet (Ratnaike 2003, *Postgrad Med J* 2003, 79:391-396). Many intestinal bacteria such as *E. coli*, *Lactobacillus* and *Bacteroides* contain arsenic resistance genes (FIG. 5A), substantiating the competitive advantage for having this ability in the intestine. As the unique regions, 5 and 7, containing these arsenic resistance genes do not correspond to BDI peaks (FIG. 2A), it suggests they may not be recently acquired by strain DJO10A, but rather lost from strain NCC2705. This theory, that adaptation to a pure-culture fermentation environment can result in loss of arsenic resistance, was further substantiated by the exceptional arsenate resistance of strain DJO10A which was 2,000% greater than a fermentation adapted *Bifidobacterium* isolate (*B. animalis* subsp. *lactis* BB12) and 100% greater than *E. coli* K12 (FIG. 5B). This would suggest that this phenotype is a competitive advantage to intestinal isolates, but not of significance for pure-culture fermentation environments.

Lantibiotic production. The production of antimicrobial peptides, or bacteriocins, is an important characteristic for bacterial competition in natural environments. One exceptionally broad spectrum class of bacteriocins is the lantibiotics, which are post-translationally modified to form lanthionine residues and to date none have been isolated from any bifidobacteria. A 10.2 kb gene cluster encoding all the genes indicative of a lantibiotic was detected in the unique region 12 of strain DJO10A (FIG. 6A). It was also noted that this unique region did not correspond to a BDI peak, suggesting a likely loss of this region from strain NCC2705. As lantibiotic production would be very advantageous for microbial competition in the intestine, but of no value to a microbe in pure culture, it provides the selective pressure for the loss of this unique region 12 from strain NCC2705.

Figure 12:
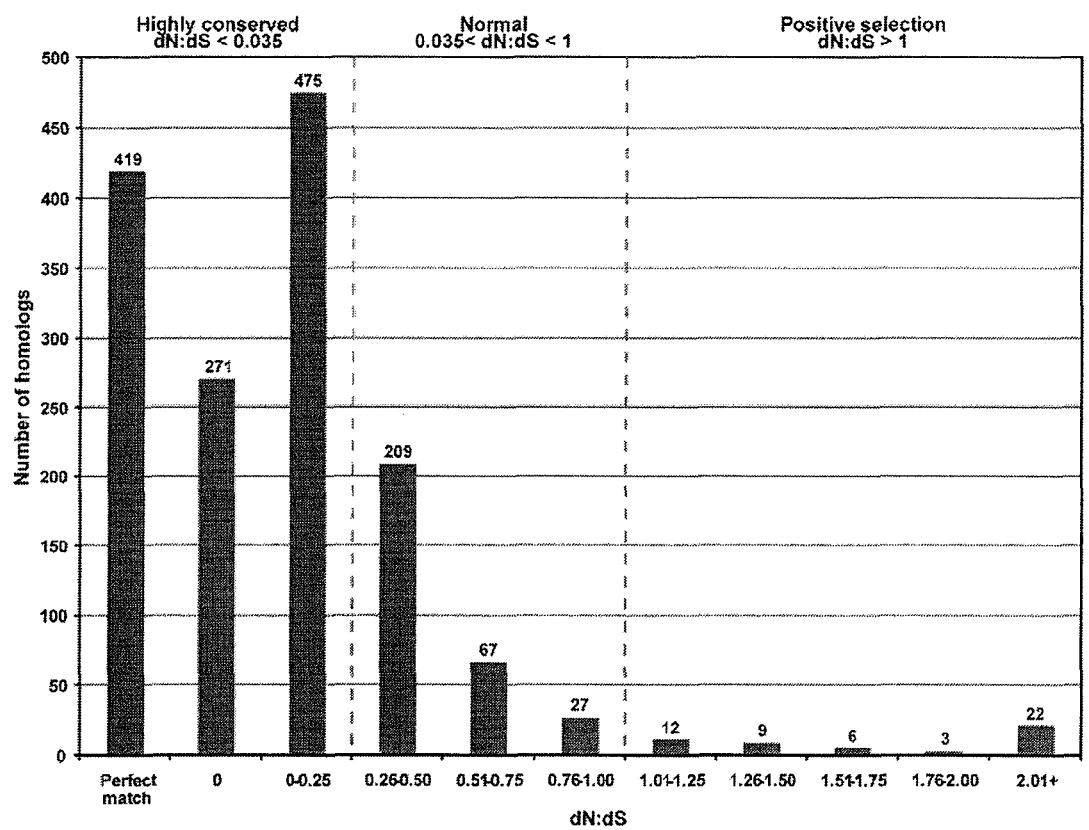
FIG. 12. Nucleotide substitution analysis of all gene homologs between *B. longum* DJO10A and NCC2705, according to the dN:dS ratio.
Figure 13:
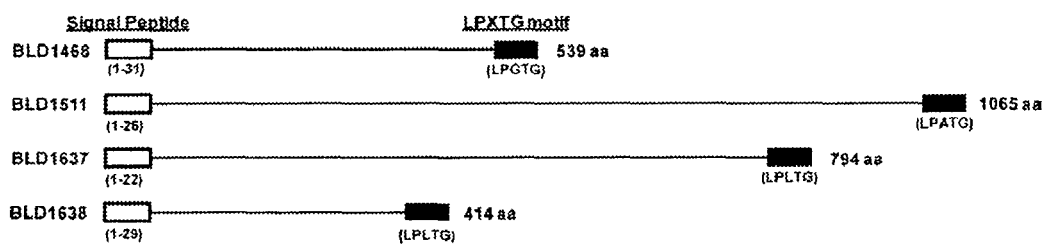
FIG. 13. Organization of four predicted LPXTG-type, cell surface anchor proteins in *B. longum* DJO10A. The numbers below the signal peptide boxes indicate the location of signal peptides. The size of the respective proteins is indicated in amino acids.

Genome attenuation of *B. longum* in fermentation environments. Given the large number of unique DNA regions in the genome of strain DJO10A, that are predicted to have been lost from strain NCC2705, it suggests that deletion of DNA regions that are not useful may reflect the rapid adaptation of *B. longum* to a new and very different environment than exists in the human large gut. This would suggest an elevated mutation frequency. A comparative nucleotide substitution analysis between strains DJO10A and NCC2705 shows the majority of genes are highly conserved (FIG. 12), which is to be expected with two closely related strains. However, analysis of the 52 least conserved genes (listed as 'positive selection' in FIG. 12) indicates that of the mutations that can be attributed to one strain or the other (frameshifts, deletions, insertions and stop mutations), 11 are from strain NCC2705 and three from strain DJO10A (Table 4). Further substantiation of an increased mutation frequency in strain NCC2705 comes from comparing genes encoding surface protein homologs between the two strains. A search of the DJO10A genome for LPXTG motifs, which is a signature of one class of cell surface anchoring proteins found four potential proteins and SignalP analysis of these proteins (BLD1468, BLD1511, BLD1637 and BLD1638) confirmed the presence of a signal sequence in each case (FIG. 13 Additional file 10). In addition, BLASTP analysis of these four proteins showed that they are very similar to other known surface proteins containing the LPXTG motif. The NCC2705 showed three of these gene homologs (BLD1468, BLD1637 and BLD1638), and had a predicted protein exhibiting 99% amino acid identity to BLD1511, but was missing the LPXTG motif due to an ISL3 insertion in the 3' end of the gene. This further highlights the rapid evolutionary status of bifidobacteria when they are removed from the human gut into pure-culture fermentation environments.

TABLE 4

Substitution ratios of the 52 genes in the positive selection category.

| DJO10A | NCC2705 | dN:dS | Annotation | Mutation |
|---|---|---|---|---|
| BLD1991 | BL1813 | 20.0673 | Hypothetical protein | Frameshift (NCC2705) |
| BLD1477 | BL1511 | 14.3257 | Hypothetical protein | Frameshift and insertion (NCC2705) |
| PyrH | pyrH | 12.9880 | Uridylate kinase | Frameshift (NCC2705) |
| BLD0511 | BL0781 | 12.7529 | Hypothetical protein | Frameshift (NCC2705) |
| BLD0760 | BL1007 | 10.5700 | Predicted glycosyltransferase | Frameshift (NCC2705) |
| ruvB | ruvB | 9.3214 | Holliday junction resolvasome, helicase subunit | |
| citB | BL1402 | 7.5024 | Response regulator | Deletion (DJO10A) |
| ppa | ppa | 6.2668 | Inorganic pyrophosphatase | Deletion (NCC2705) |
| BLD0382 | BL1490 | 6.1532 | Hypothetical protein | Frameshift (NCC2705) |
| BLD1282 | BL0491 | 4.2133 | Hypothetical protein | |
| BLD0801 | BL1050 | 4.0425 | Hypothetical protein | |
| soj | BL1492 | 3.8930 | ATPase involved in chromosome partitioning | |
| BLD1365 | BL0571 | 3.7661 | Predicted esterase | Deletion (NCC2705) |
| ardA | BL1465 | 3.6056 | Antirestriction protein | |
| cbiO | BL0049 | 3.4507 | ABC-type cobalt transport system, ATPase component | |
| BLD0038 | BL0026 | 3.3177 | Hypothetical protein | |
| BLD0376 | BL1489 | 3.2395 | Hypothetical protein | Deletion (DJO10A) |
| dppD | oppD | 3.1112 | ABC-type dipeptide/oligopeptide transport system | |
| BLD0144 | BL0126 | 3.0474 | Hypothetical protein | |
| BLD1389 | BL0595 | 2.4181 | Hypothetical protein | |
| BLD0109 | BL0091 | 2.3769 | Predicted aminoglycoside phosphotransferase | |
| srtA | BL0676 | 2.3202 | Sortase (surface protein transpeptidase) | Deletion (NCC2705) |
| BLD0716 | BL0962 | 1.9561 | Predicted acyltransferase | |
| metK | metK | 1.9085 | S-adenosylmethionine synthetase | Frameshift (NCC2705) |
| BLD1580 | BL1246 | 1.7926 | Hypothetical protein | |
| BLD1774 | BL1650 | 1.7408 | Hypothetical protein | |
| lytE | BL1311 | 1.7363 | LysM repeat | |
| azlC | BL1669 | 1.6564 | Predicted branched-chain amino acid permease | |
| glgP | glgP | 1.5354 | Glucan phosphorylase | |
| BLD1672 | BL1553 | 1.5276 | Flagellar basal body P-ring biosynthesis protein | |
| BLD1399 | BL0605 | 1.5179 | Hypothetical protein | |

TABLE 4-continued

Substitution ratios of the 52 genes in the positive selection category.

| DJO10A | NCC2705 | dN:dS | Annotation | Mutation |
|---|---|---|---|---|
| ftsW | ftsW | 1.4969 | Uridylate kinase | |
| BLD1753 | BL1627 | 1.4775 | Predicted transcriptional regulator | |
| nagA | nagA | 1.3702 | N-acetylglucosamine-6-phosphate deacetylase | |
| BLD0620 | BL0885 | 1.3620 | Predicted acyltransferase | Stop mutation (DJO10A) |
| DAP2 | BL1649 | 1.3497 | Dipeptidyl aminopeptidase/acylaminoacyl-peptidase | |
| BLD1741 | BL1614 | 1.3341 | Hypothetical protein | |
| topB | topB | 1.3066 | Topoisomerase III | Annotation difference[a] (NCC2705) |
| topA | topA | 1.2608 | Topoisomerase I | |
| BLD0571 | BL0837 | 1.2585 | Hypothetical protein | |
| BLD0397 | BL1498 | 1.2350 | Hypothetical protein | |
| wecD | BL1151 | 1.2166 | Histone acetyltransferase HPA2 | |
| pepC | pepC2 | 1.1349 | Aminopeptidase C | |
| sdrC | BL0094 | 1.1037 | Predicted secreted protein containing a PDZ domain | |
| BLD1612 | BL1278 | 1.0894 | ABC-type transport system | |
| BLD1568 | rmlB1 | 1.0865 | dTDP-D-glucose 4,6-dehydratase | |
| BLD0548 | BL0810 | 1.0694 | Hypothetical protein | |
| BLD1455 | BL0660 | 1.0642 | Serine/Threonine protein kinase | |
| BLD0375 | BL1488 | 1.0557 | Hypothetical protein | Deletion (NCC2705) |
| BLD1772 | BL1648 | 1.0402 | Hypothetical protein | |
| BLD1401 | BL0607 | 1.0338 | Hypothetical protein | |
| BLD1983 | BL1815 | 1.0056 | Hypothetical protein | |

[a]An N-terminal extension in the annotation of TopB in strain NCC2705 does not map to any other TopB sequence.

Figure 7:
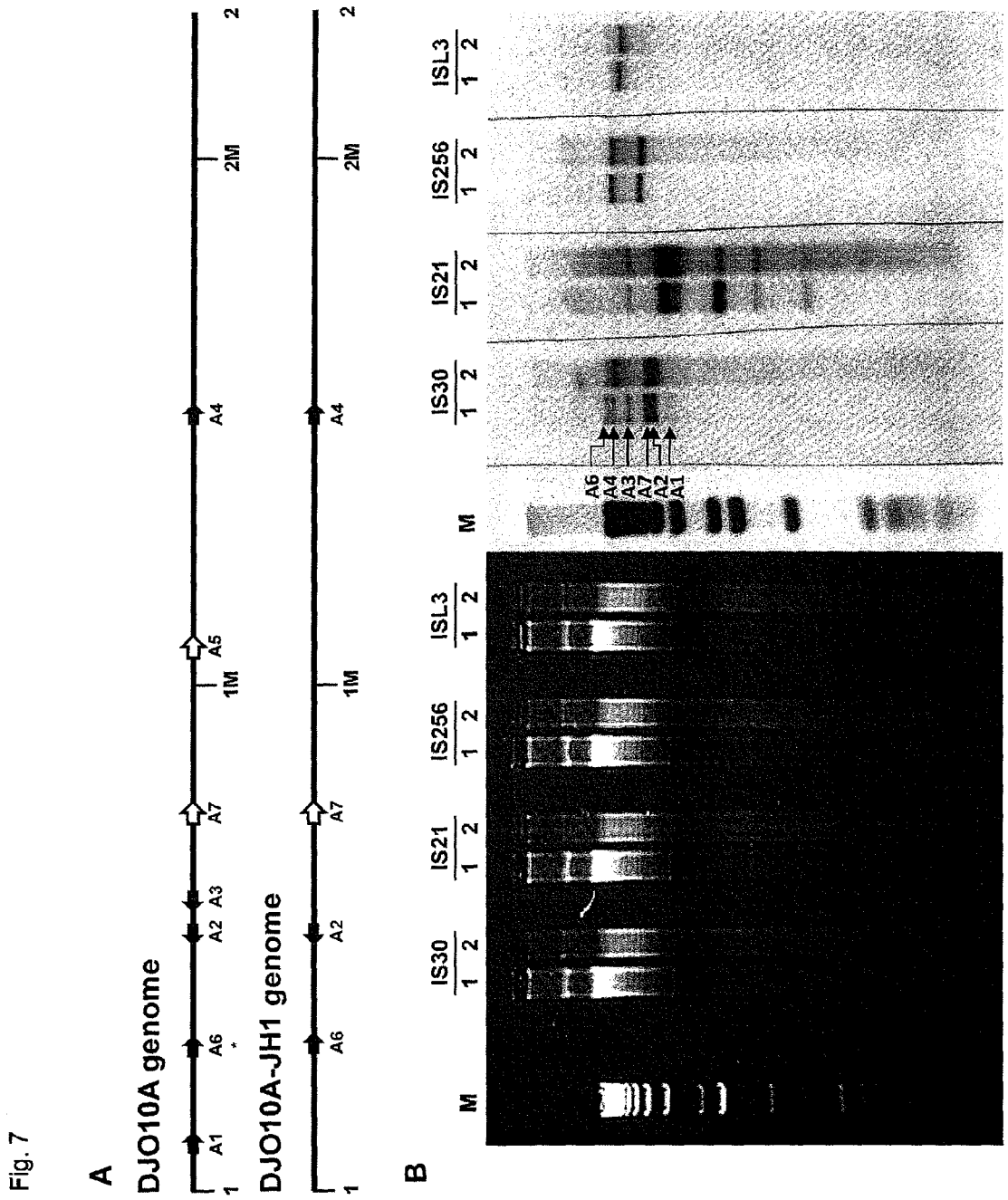
FIG. 7. IS30 'jumping' in the genome of *B. longum* DJO10A. (A) Genome positioning of the IS30 elements in the genome of *B. longum* DJO10A and the laboratory adapted strain DJO10A-JH1. The gray arrows indicate the five elements identified by direct sequencing of DJO10A genomic DNA. The white arrows indicate the location of elements that were detected in some sequencing clones prepared from DJO10A genomic DNA. The asterisk under A6 indicates this element was missing from some sequencing clones of DJO10A DNA. (B) NruI digested genomic DNA from DJO10A shown in the left gel and its Southern hybridization (right gel) using probes specific for four different IS element families. (1) refers to DJO10A and (2) refers to DJO10A-JH1. Arrows indicate bands in DJO10A corresponding to specific IS30 elements as illustrated in (A).

IS30 'jumping' in the *B. longum* genome. The dynamic environment within the *B. longum* cell in a fermentation environment is further substantiated by the intriguing observation during genome sequencing from different batches of DNA that everything was identical except for the location of some IS30 elements (FIG. 7A). This very rapid movement of an IS element within a cell has not been observed previously. The movement of IS30 within the genome occurred only at specific sites, consistent with its insertion target specificity (Olasz et al., 1998, *Mol Microbiol* 1998, 28:691-704).

Adaptation of *B. longum* DJO10A to a pure-culture environment. To test the hypothesis that the switch from a variable and complex environment like the gut to a relatively stable and simplified, pure-culture one, results in hyper IS30 activity and rapid DNA loss of regions that are no longer beneficial to the new environment, strain DJO10A was grown in a typical laboratory medium without pH control for ~1,000 generations. Isolated colonies were then screened for seven unique regions encoding functions predicted to be useful for survival in the human gut. One of these regions (no. 12) involved in the lantibiotic production was found to be missing from 40% of the isolates (FIG. 14) substantiating this hypothesis. Analysis of this adapted strain, DJO10A-JH1, shows the deletion extended over the full lantibiotic region very similar to strain NCC2705 (FIG. 6A). It is further noted using Pulsed Field Gel Electrophoresis (PFGE) that the 39.9 kb XbaI band containing this region is missing from strain DJO10A-JH1 (FIG. 6B). The loss of the complete lantibiotic gene cluster from 40% of the culture was intriguing as the cluster also encodes the immunity gene to protect cells from the lantibiotic activity. However, analysis of lantibiotic production by strain DJO10A showed that none occurred during growth in broth media, and a solid surface such as agar, was needed for production (FIG. 6C) similar to streptin production from *Streptococcus pyogenes* (Wescombe and Tagg, 2003, *Appl Environ Microbiol* 2003, 69:2737-2747). The loss of the complete lantibiotic gene cluster renders strain DJO10A-JH1 sensitive to this pronase-E sensitive lantibiotic, which is also active against a wide spectrum of bacteria (FIG. 6C). Interestingly, the lantibiotic genome region that was deleted during the adaptation of strain DJO10A to the pure-culture environment was located between two IS30 elements, suggesting its role in genome deletion events.

It was also noted that the pure-culture adapted strain, DJO10A-JH1, was also missing a 140.7 kb XbaI band (FIG. 6B). It is intriguing that this band contains one of the four MIC elements, suggesting it may have been involved. PCR analysis of the loci immediately bordering this MIC element revealed the deletion extended between 10 and 50 kb directly downstream from this element substantiating its likely role in this deletion event. This further substantiated the rapid loss of DNA, and the prominent role of mobile elements, during evolutionary adaptation by these bacteria.

Southern hybridization of strains DJO10A and DJO10A-JH1 substantiate the IS30 'jumping' during growth in a pure-culture environment, while the positions of the other IS elements (IS21, IS256 and ISL3) remained stable (FIG. 7B). This IS30 hyperactivity in *B. longum* genomes may play an important role in deletion events and genome reduction during adaptation to new environments.

Figure 15:
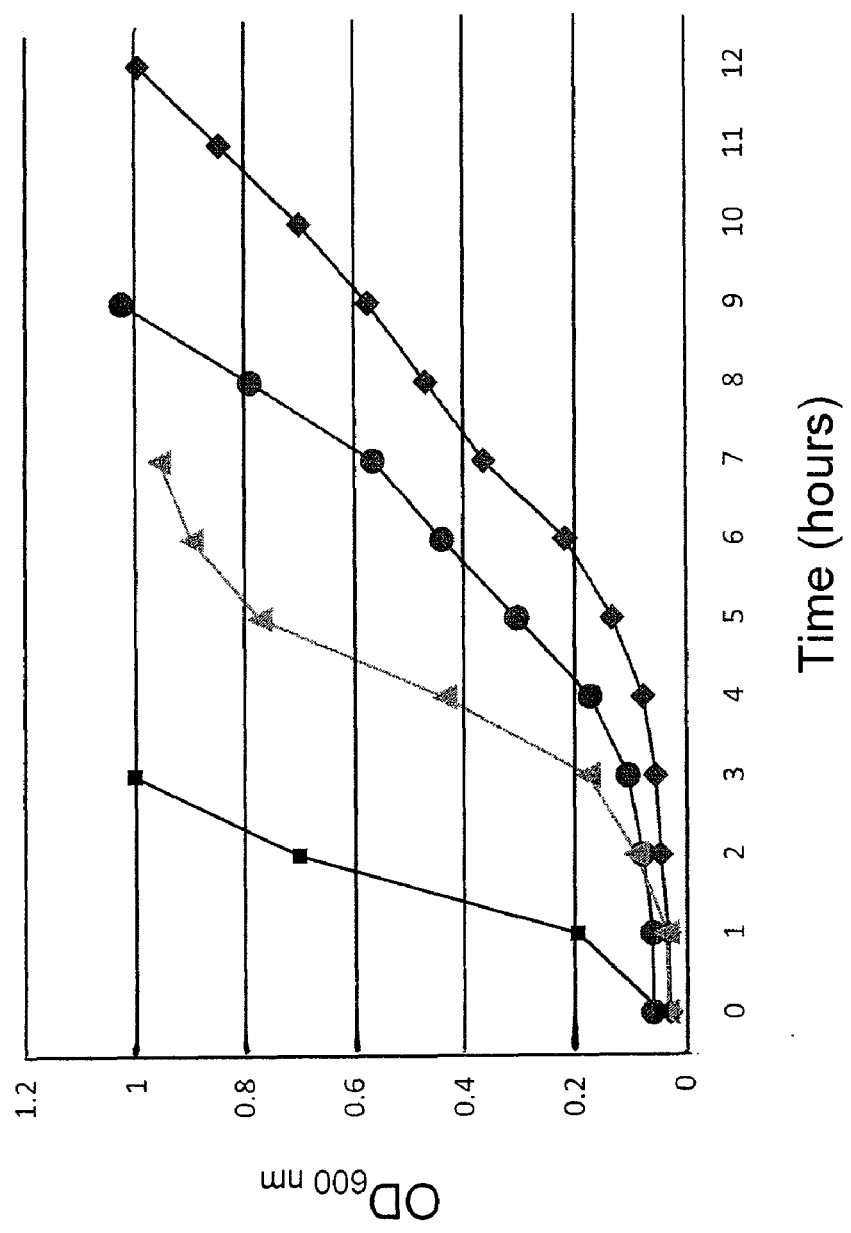
FIG. 15. Growth curves in RCM medium of the four bacteria used in the fecal competitive growth experiments. All bacteria were inoculated at 1% from freshly grown cultures. Squares, *E. coli* DJOec1; triangles, *Clostridium difficile* DJOcd1; circles, *B. longum* DJO10A-JH1; and diamonds, *B. longum* DJO10A.

Competitive 'fitness' of the adapted *B. longum* strain DJO1A-JH1. The rapid genome reduction experienced by *B. longum* DJO10A during pure-culture growth in fermentation conditions suggested that the genomic regions lost may have been important for competition in the intestine. To test if this in vitro adaptation affected the 'fitness' of the strain, a simulated fecal competitive approach was developed. Bifidobacteria are frequently proposed to successfully compete against members of the clostridia and the enterobacteriae in the intestinal environment. A member of both of these bacterial groups was selected to test the relative competitive abilities of *B. longum* DJO10A and its in vitro adapted derivative, strain DJO10A-JH1. To ensure that the selected competitor strains were not attenuated in any way, new isolates were obtained from fresh feces by plating on selective media and speciated using a sequence analysis of the 16S rRNA gene. This resulted in the isolation of *Clostridium difficile* DJOcd1 and *E. coli* DJOec1, which were minimally cultured prior to undergoing fecal competitive experiments with the *B. longum* strains. An in vitro growth rate analysis established that *E. coli* DJOec1 had the fastest growth rate, followed by *C. difficile* DJOcd1, *B. longum* DJO10A-JH1 and *B. longum* DJO10A (FIG. 15). The noticeable increased growth rate of

*B. longum* DJO10A-JH1 compared to strain DJO10A substantiated that the genome reduction of strain DJO10A-JH1 favored the in vitro growth environment.

Figure 8:
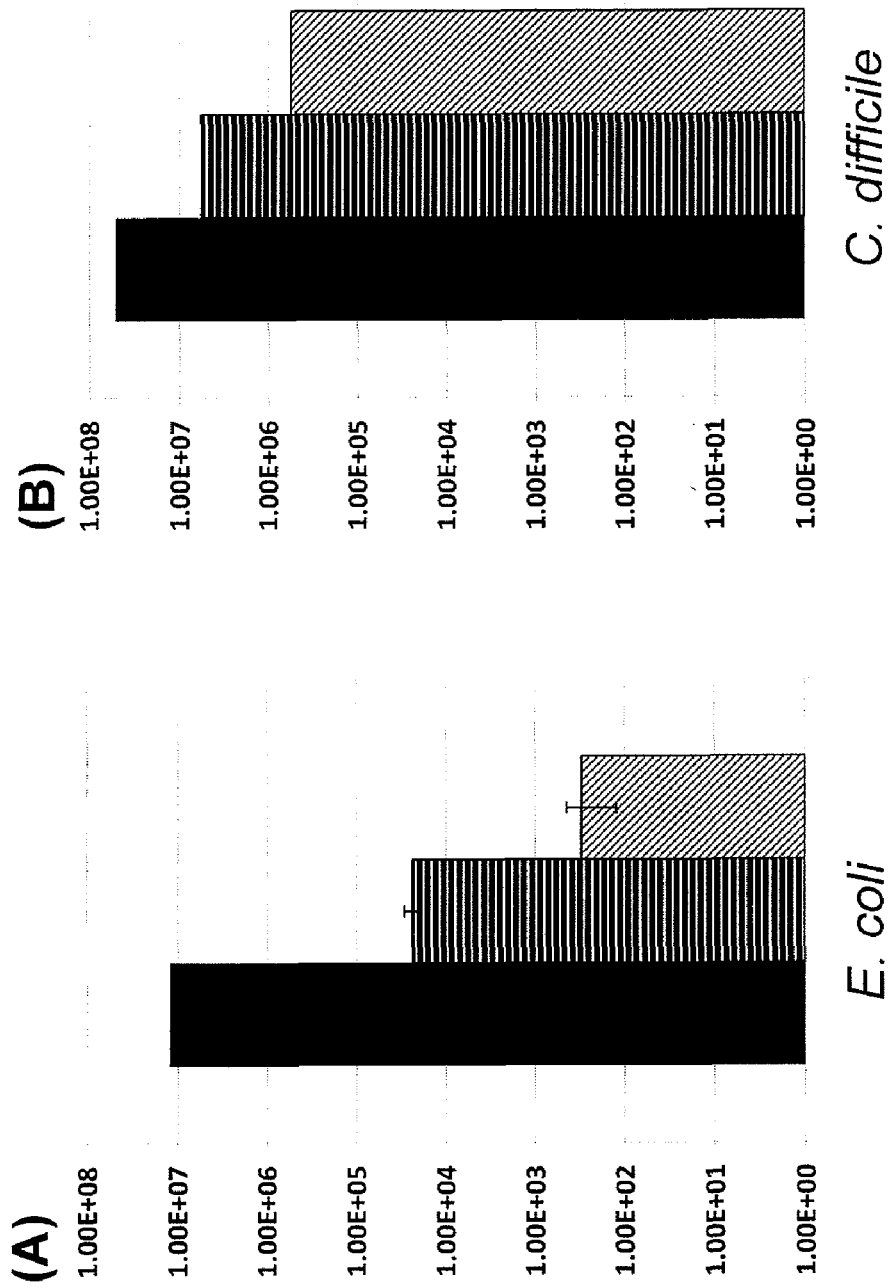
FIG. 8. Simulated fecal competitive analysis of *B. longum* DJO10A and its in vitro adapted derivative, strain DJO10A-JH1, against *Clostridium difficile* and *E. coli*. (A) Viable cell counts of *E. coli* DJOec1 at the beginning of the competitive study (black), following competition with *B. longum* DJO10A-JH1 (horizontal lines) and *B. longum* DJO10A (hatched). (B) Viable cell counts of *C. difficile* DJOcd1 at the beginning of the competitive study (black), following competition with *B. longum* DJO10A-JH1 (horizontal lines) and *B. longum* DJO10A (hatched). N=3.

Competitive growth experiments with both *E. coli* DJOec1 and *C. difficile* DJOcd1 in a simulated anaerobic fecal environment revealed that *B. longum* DJO10A had a significantly greater ability to compete against both *E. coli* and *C. difficile* (FIG. 8). The significantly greater reduction in both these groups of bacteria by *B. longum* DJO10A supports the genome analysis hypothesis that the genome reduction exhibited in pure-culture growth may compromise a bacterium's ability to compete in its original environment.

While the simulated fecal competition studies suggested that the lantibiotic encoding genome region was important for competition in the human intestine, in vivo studies in an intestinal model would be necessary to verify this hypothesis.

Methods

Bacterial strains and growth conditions. *Bifidobacterium longum* strain DJO10A was isolated from a healthy young adult's feces (Islam, 2006, *MS thesis*. University of Minnesota, Department of Food Science and Nutrition) and *B. animalis* subsp. *lactis* BB12 was obtained from Chr. Hansen (Denmark). *B. animalis* subsp. *lactis* strains S1, S2, and S14 are genetically distinct isolates from fermented foods. *Clostridium difficile* DJOcd1 was isolated from fresh feces by plating on *Clostridium difficile* Selective Agar (BD Diagnostics) and speciated using a sequence analysis of its 16S rRNA gene. *E. coli* DJOec1 was obtained from fresh feces by plating on MacConkey agar (Difco) and speciated using a sequence analysis of its 16S rRNA gene. *E. coli* K12 was obtained from the American Type Culture Collection (ATCC). Bifidobacteria were cultivated at 37° C. in MRS (Difco) supplemented with 0.05% L-cysteine HCl (Sigma), Bifidobacteria Low-Iron Medium (BLIM) (Islam, 2006, *MS thesis*. University of Minnesota, Department of Food Science and Nutrition) or Bifidobacteria Fermentation Medium (BFM) (2% proteose peptone, 0.15% K2HPO4, 0.15% MgSO4.7H2O, 0.5% D-glucose) under anaerobic conditions using either the BBL Anaerobic system (BBL) or the Bactron II Anaerobic/Environmental Chamber (Sheldon Manufacturing).

Genome sequencing and assembly. Whole-genome shotgun sequencing was carried out at the US Department of Energy Joint Genome Institute (JGI). Sequences were assembled into 227 contigs using the Phred/Phrep/Consed software and the sequence coverage was 9.2-fold. Gap closure and genome sequence finishing was carried out at Fidelity Systems using ThermoFidelase-Fimer direct genome sequencing technology (Slesarev et al., 2002, *Proc Natl Acad Sci USA*, 99:4644-4649). Shotgun reads with and without IS30 elements covering A5, A6 and A7 loci were identified and assembled separately. The presence and location of long repeated sequences in genomic DNA samples were verified by direct genomic sequencing of the unique/repeat junctions. The resolution of the most complex high GC-rich repeats was achieved by sequencing of PCR products amplified with a hybrid TopoTaq DNA polymerase with increased strand displacement capacity.

Bioinformatic analysis. Annotation of all open reading frames (ORFs) was carried out using Glimmer, GeneMark, JGI annotation tools and GAMOLA (Altermann et al., 2003, *OMICS* 2003, 7:161-169), before manual checking of all predicted genes. A comparative analysis of the two *B. longum* genomes was conducted using MUMmer3, ACT4 and ClustalX. The origin of replication and terminus were predicted using OriLoc (Frank and Lobry, 2000, *Bioinformatics* 2000, 16:560-561). Codon usage was analyzed using the General Codon Usage Analysis (GCUA) program (McInerney 1998, *Bioinformatics* 1998, 14:372-373). The base-deviation index (BDI) was performed by scaled $\chi^2$ analysis of Artemis8. To predict gene functions, the two conserved protein domain databases of GAMOLA and InterProScan were used. COG functional categories were used for functional classification of all genes in both *B. longum* genome sequences.

Molecular techniques. General sequencing was conducted using a Big-Dye terminator and ABI Prism 3730x1 Auto sequencer (Applied Biosystems). All PCR primers are listed in Table 5. For Southern blot analysis of unique region 12, a 646 bp probe from the lanM gene was obtained using PCR with LANT-F and LANT-R primers. Probes for IS elements were also PCR amplified. Probes were DIG-labeled and hybridized with digested genomic DNA according to the manufacturer's instructions (Roche). Pulsed field gel electrophoresis of XbaI-digested *B. longum* genomes was performed using a CHEF-DR III Variable Angle Pulsed Field Electrophoresis System according to manufacturer's instructions (Bio-Rad).

TABLE 5

Primers used.

| Target region Unique region no.[a] | Primer | Sequence[b] | Size | Reference |
|---|---|---|---|---|
| Oligo cluster | | | | |
| 15 | OLIGO15-F | 5'-GAAATCCCGAAANACNACC-3' | 1,793 bp | This study |
|  | OLIGO15-R | 5'-GTTGCCGATGTTYTGNCC-3' | | |
| 6 | OLIGO6-F | 5'-GTATGTGATGAGCGGNAGY-3' | 1,840 bp | This study |
|  | OLIGO6-R | 5'-ACCAACGGATTTYTGNGG-3' | | |
| 9 | OLIGO9-F | 5'-AAGTTCACCGATGARACN-3' | 2,001 bp | This study |
|  | OLIGO9-R | 5'-GTAACGCAACGARTAYTCC-3' | | |
| 11 | OLIGO11-F | 5'-TCCCCAACTACATTATHGTNG-3' | 1,419 bp | This study |
|  | OLIGO11-R | 5'-TCAACACCATCNGCNACC-3' | | |
| Arsenic cluster | | | | |
| 5 | ARS5-F | 5'-ATTGGCTTATTGCTNACN-3' | 736 bp | This study |
|  | ARS5-R | 5'-GACTGCTTCAACTGNAGDATCC-3' | | |

TABLE 5-continued

Primers used.

| Target region Unique region no.[a] | Primer | Sequence[b] | Size | Reference |
|---|---|---|---|---|
| 7 | ARS7-F | 5'-ACAGTCCCAATACAGTAARACN-3' | 1,125 bp | This study |
|  | ARS7-R | 5'-CTCAAAGAAATTAGANGCNCC-3' | | |
| Lantibiotic | | | | |
| 12 | LANT-F | 5'-CGCTATTACACCAGATACG-3' | 646 bp | This study |
|  | LANT-R | 5'-GGTAGACATACAGGTTCTCC-3' | | |
| Positive control (16S rRNA gene) | | | | |
|  | 16S-F | 5'-CAGCWGCCGCGGTAATWC-3' | 890 bp | (Lane et al., 1985) |
|  | 16S-R | 5'-ACGGGCGGTGTGTRC-3' | | |
| Deletion of lantibiotic operon | | | | |
| Forward | F3 | 5'-ATCCAACGAGCAAGAACC-3' | | This study |
| Reverse | R3 | 5'-GTGAAATCACCACTACCACC-3' | | |
| Deletion of MIC III region | | | | |
| Upstream | MIC-F1 | 5'-CACATCTTGGAACTGCTTGG-3' | | This study |
|  | MIC-R1 | 5'-CGTACACCGATGAATGACC-3' | | |
| Downstream | MIC-F2 | 5'-GTTCTTCGTCACCTCCACC-3' | | |
|  | MIC-R2 | 5'-AGTAATGTCCCGAATCCTCC-3' | | |
| IS elements | | | | |
| IS30 | IS30-F | 5'-GACAAACCCAAGACCCTCC-3' | 352 bp | This study |
|  | IS30-R | 5'-CGTGCATATCCCCATTATCC-3' | | |
| IS21 | IS21-F | 5'-GCCCCAAGTACAGTCTATCC-3' | 681 bp | This study |
|  | IS21-R | 5'-CAGAACGAACAATCGAACC-3' | | |
| IS256 | IS256-F | 5'-TGTCACAGCAGATTCTACAGG-3' | 719 bp | This study |
|  | IS256-R | 5'-CAGCAATTCGTTCACAGC-3' | | |
| ISL3 | ISL3-F | 5'-CGAGATCGTCGAGCTTTCC-3' | 169 bp | This study |
|  | ISL3-R | 5'-ATCAGGGCGATGAGGTTGG-3' | | |

[a] as defined in the text;
[b] Y (C/T), R (A/G), H (A/C/T), D (A/G/T), N (A/T/G/C), W (A/T) SEQ ID NOs: 26-55
Lane et al., 1985. Proc. Natl. Acad. Sci. USA 82: 6955-6959.

Identification of gene homologs between the two *B. longum* genomes. Comparative nucleotide substitution analysis by Nei and Gojobori's algorithm (Nei and Gojobori, 1986, *Mol Biol Evol* 1986, 3:418-426) was used to identify gene homologs. The predicted genes of both genome sequences were compared using the local BlastN program in the NCBI toolkit and 1,590 aligned genes were used for the nucleotide substitution analysis by Nei's unweighted method I (Nei and Gojobori, 1986, *Mol Biol Evol* 1986, 3:418-426). According to the ratio of dN:dS, all matched genes were categorized into three groups, highly conserved (<0.035), normal, and positive selection (>1).

Minimal inhibitory concentration of arsenic. To determine the minimal inhibitory concentration of arsenic, BLIM was supplemented with different concentrations of sodium arsenite (AsO2-, 1 to 100 mM) and sodium arsenate (AsO3-, 1 to 500 mM). Freshly grown cultures were sub-inoculated into the arsenite/arsenate media and incubated anaerobically at 37° C. for 48 hours.

Adaptation of *B. longum* DJO10A to in vitro fermentation conditions. *B. longum* DJO10A was grown in BFM continuously up to ~1,000 generations. The culture was then serially diluted and plated on BFM agar. Ten colonies were randomly selected for analysis.

Figure 6:
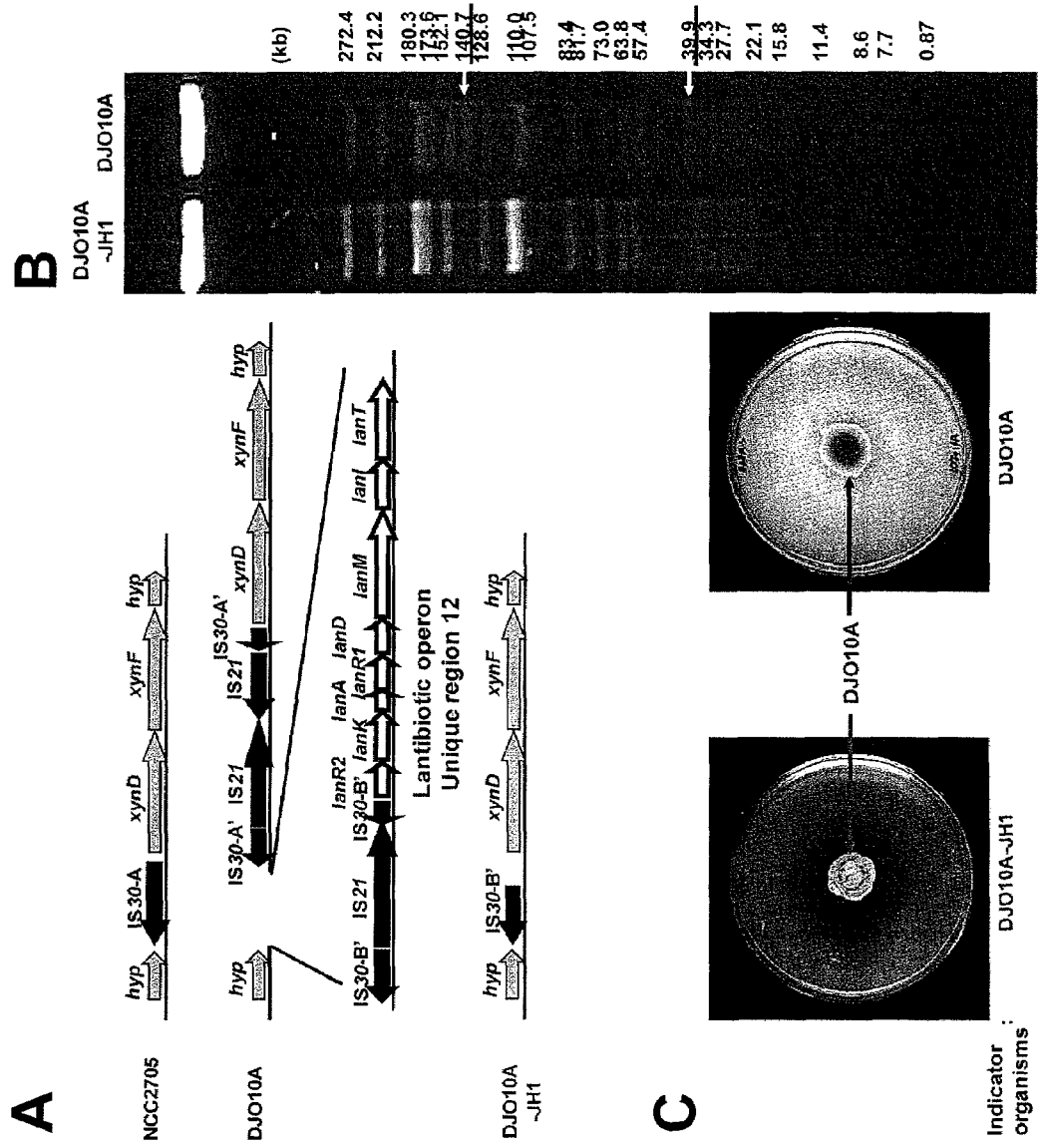
FIG. 6. Lantibiotic production by *B. longum* DJO10A. (A) Organization of the lantibiotic encoding unique region 12 of *B. longum* DJO10A and the corresponding genome locations in strains NCC2705 and DJO10A-JH1. The A or B designator following IS30 refer to unique classes of IS30 elements that are only found at this location in the genome. The 'designator indicates a fragmented IS30 element. (B) Pulsed Field Gel Electrophoresis (PFGE) analysis of XbaI-digested total DNA from *B. longum* DJO10A and its fermentation adapted isolate, DJO10A-JH1. White arrows indicate bands missing from strain DJO10A-JH1. (C) Bioassay for lantibiotic production by *B. longum* DJO10A with strains DJO10A and DJO10A-JH1 as indicator bacteria.

Mapping the deletions in strain DJO10A-JH1. To find the precise location of the deletion of the lantibiotic operon in the *B. longum* DJO10A-JH1 genome, PCR was used to test for several genes within the lantibiotic operon. The two primers F3 (position 1,974,570-1,974,587 bp) and R3 (position 1,996,024-1,996,005 bp) were used to amplify a ~1.8 kb region spanning the deletion and sequencing located the precise borders (FIG. 6). To map the position of the deletion in the 140.7 kb XbaI fragment, primers MIC-F1 (position, 1,539,767-1,539,768) and MIC-R1 (position, 1,542,535-1,542,553) were used to amplify the upstream region of MIC III and primers MIC-F2 (position, 1,543,406-1,543,424) and MIC-R2 (position, 1,545,713-1,545,732) were used to amplify the downstream region.

Bioassay for lantibiotic activity. *B. longum* DJO10A was inoculated into the center of an MRS agar plate and incubated anaerobically at 37° C. for 2 days. After incubation, molten 0.5% top agar of the same medium containing 1% of an indicator strain was overlaid on the plates prior to incubation.

Simulated fecal competitive analysis of bifidobacteria. To access the competitive 'fitness' of the wild-type *B. longum* DJO10A compared to its in vitro adapted derivative strain DJO10A-JH1, a simulated in vitro fecal system was developed. Triplicate experiments for each strain were used. Each experiment was conducted in 10 g sterilized feces in an anaerobic chamber, to which 0.38 g Reinforced Clostridial Medium (RCM) and 0.02 g mucin (Porcine gastric type III) was added. The two competitor bacteria were added to all tubes at calculated concentrations of $1.2 \times 10^7$ cfu/g for *E. coli* DJOec1 and $5.1 \times 10^7$ for *Clostridium difficile* DJOcd1. *B. longum* DJO10A was added to three tubes at a calculated concentration of $4.0 \times 10^7$ cfu/g and strain DJO10A-JH1 to the other three tubes at 4.4 cfu/g. Standard viable plate counts were used to calculate all bacterial concentrations. After thorough mixing in an anaerobic environment, the tubes were left at 37° C. for 3 days, whereby the entire fecal samples were homogenized in 90 ml peptone water to conduct an accurate serial plate count analysis.

Example 2

Preparation of Extracted *Bifidobacterium* Lantibiotic

*B. longum* strain DJO10A was grown in MRS broth supplemented with 0.05% L-cysteine.HCl (Sigma) or Bifidobacteria Low-Iron Medium (BLIM). The broth was then used to cover the surface of an MRS agar plate supplemented with 100 mM PIPES or a BLIM agar plate supplemented with 100 mM PIPES. The plates were incubated under anaerobic conditions using either the BBL Anaerobic system (BBL) or the Bactron II Anaerobic/Environmental Chamber (Sheldon Manufacturing) at 37° C. for 2 days. Twenty plates were used.

The cells and agar medium were crushed and the mixture was extracted with 95% methanol using routine methods. The extraction was allowed to proceed overnight. The final volume was placed in a SpeedVac to remove the methanol and concentrate the lantibiotic.

The remaining agar was removed by size fractionation using Millipore CentriPrep filtration for partial purification. The extract was fractionated with a Centriprep-30 (30 kDa cut-off) by centrifugation twice at 1,500×g for 15 minutes and 10 minutes, respectively, and the filtrate (<30 kDa) transferred to a Centriprep-10 (10 kDa cut-off). This was subjected to centrifugation twice at 3,000×g for 40 minutes and 10 minutes, respectively. The filtrate was transferred to a Centriprep-3 (3 kDa cut-off). This was subjected to centrifugation twice at 3,000×g for 95 minutes and 35 minutes, respectively. The fractionated solution (3-10 kDa) was collected and concentrated by SpeedVac machine.

The concentrated lantibiotic was resuspended, and immediately tested using a diffusion method. Agar plates were made with MRS or BLIM and supplemented with PIPES, and a well of 5 millimeters cut into the middle of each plate. One hundred microliters of the suspended lantibiotic were placed in the well and allowed to diffuse until the liquid in the well was gone. The plates were then overlayed with the indicator strain.

The lantibiotic inhibited the growth of the indicator strains *M. leuteus, L. lactis, S. aureus, S. epidermdis, E. coli, S. marcescens*, and *P. vulgaris*. The lantibiotic did not inhibit *P. aeuruginosa* in this assay; however, it is not possible to conclude from these data that the lantibiotic will not inhibit *P. aeuruginosa*.

Example 3

Heat Resistance of Extracted *Bifidobacterium* Lantibiotic

The lantibiotic from example 2 was placed in a boiling water bath for 10 minutes and then tested for activity using the diffusion method and *M. leuteus* as the indicator strain. The lantibiotic was active after boiling for 10 minutes.

Example 4

Proteolytic Analysis of the Extracted *Bifidobacterium* Lantibiotic

Stock solutions of the proteolytic enzymes were prepared as follows.

Pepsin (Sigma No. P6887) was dissolved in 2 mM Tris.HCl or water at pH 2, 37° C., at a concentration of 34600 U/ml (10 mg/ml).

Pronase E (Sigma No. P5147) was dissolved in 20 mM Tris.HCl or 50 mM phosphate buffer at pH 7.5, 37° C., at a concentration of 5500 U/ml (500 mg/ml).

α-Chymotrypsin (Sigma No. C4129) was dissolved in 80 mM Tris.HCl at pH 7.8, 25° C., at a concentration of 5100 U/ml (100 mg/ml).

Proteinase K (Sigma P2308) was dissolved in 10 mM Tris.HCl at pH 7.5, 37° C., at a concentration of 6000 U/ml (200 mg/ml).

Trypsin (MP biochemical (ICN) No. 15021310), pH 7.6, 25° C., was used at the concentration 4750 U/ml (50 mg/ml).

Thermolysin (Fluka No. 88303), pH 7.2, 37° C., was used at the concentration 6000 U/ml (150 mg/ml).

One hundred microliters of the lantibiotic from example 2 was used in each assay. The proeolytic enzymes were added to separate 100 mls of the lantibiotic as follows: pepsin, 5 μl (173 U); pronase E, 20 μl (110 U); α-Chymotrypsin, 20 μl (102 U); proteinase K, 20 μl (120 U); trypsin, 20 μl (95 U); and thermolysin, 20 μl (120 U). Samples containing pepsin, Pronase E, Proteinase K, or Thermolysin were incubated at 37° C., and samples containing α-Chymotrypsin or Trypsin were incubated at 25° C. The incubation was for 24 hours. After digestion, the sample was neutralized to pH7.5, and all samples were incubated in boiling water for 10 minutes to remove the proteolytic enzyme activity.

Each sample was tested for activity using the diffusion method, 50 μl of the sample containing the inactivated proteolytic enzyme, and *M. leuteus* as the indicator strain. The extracted lantibiotic was sensitive to pepsin (at pH 2) and to pronase E (at pH7.5), and insensitive to the other 4 proteolytic enzymes.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated biologically active compound comprising an amino acid sequence, wherein the amino acid sequence of the compound and the amino acid sequence of SEQ ID NO:21 have at least 80% identity, wherein the compound is not inactivated by digestion with trypsin at 25° C. for 24 hours, and wherein SEQ ID NO:21 is proline-alanine-Xaa1-leucine - Xaa2-phenylalanine-alanine-valine- Xaa3-valine-leucine- Xaa4-valine- Xaa5-phenylalanine - Xaa6-alanine- Xaa7- Xaa8-valine- Xaa9-valine-valine- Xaa10-arginine-leucine-alanine - Xaa11- Xaa12-glycine-asparagine- Xaa13-lysine, where Xaa1, 2, 3, 4, 5, 6, 8, and 11 are each independently serine, didehydroalanine, or alanine, Xaa7, 12, and 13 are each independently cysteine or alanine, and Xaa9 and 10 are each independently threonine, didehydrobutyrine, or 2-aminobutyric acid.

2. The isolated biologically active compound of claim 1 wherein the amino acid sequence of the compound comprises at least one conservative substitution of the amino acid sequence of SEQ ID NO:21.

3. The isolated biologically active compound of claim 1 wherein the compound comprises the characteristic of inhibiting growth of a Gram negative microbe in conditions that do not damage the outer membrane of the Gram negative microbe.

4. The isolated biologically active compound of claim 3 wherein the compound inhibits growth of an *E. coli*, a *Serratia proteus*, or a *Salmonella* spp.

5. The isolated biologically active compound of claim 1 wherein the compound inhibits growth of a Gram positive microbe *Lactobacillus* spp., a *Lactococcus* spp., a *Streptococcus* spp., a *Staphylococcus* spp., or a *Bacillus* spp.

6. The isolated biologically active compound of claim 1 wherein the compound is produced by a *Bifidobacterium*.

7. The isolated biologically active compound of claim 1 wherein the amino acid sequence of the compound and the amino acid sequence of SEQ ID NO:21 have at least 95% identity.

8. An isolated lantibiotic, wherein the lantibiotic inhibits growth of a Gram negative microbe in conditions that do not damage the outer membrane of the Gram negative microbe, wherein the lantibiotic is not inactivated by digestion with trypsin at 25° C. for 24 hours.

9. The lantibiotic of claim 8 wherein the lantibiotic comprises an amino acid sequence, wherein the amino acid sequence of the lantibiotic and the amino acid sequence of SEQ ID NO:21 have at least 80% identity, and wherein SEQ ID NO:21 is proline- alanine -Xaa1-leucine- Xaa2-phenylalanine-alanine-valine- Xaa3-valine-leucine- Xaa4-valine- Xaa5-phenylalanine- Xaa6-alanine- Xaa7- Xaa8-valine- Xaa9-valine-valine-Xaa10-arginine-leucine-alanine-Xaa11-Xaa12-glycine-asparagine-Xaa13-lysine, where Xaa1, 2, 3, 4, 5, 6, 8, and 11 are each independently serine, didehydroalanine, or alanine, Xaa7, 12, and 13 are each independently cysteine or alanine, and Xaa9 and 10 are each independently threonine, didehydrobutyrine, or 2-aminobutyric acid.

10. The isolated lantibiotic of claim 9 wherein the Gram negative microbe is an *E. coli*, a *Serratia proteus*, or a *Salmonella* spp.

11. The isolated lantibiotic of claim 9 wherein the amino acid sequence of the compound and the amino acid sequence of SEQ ID NO:21 have at least 95% identity.

12. A composition comprising the isolated biologically active compound of claim 1 and a food product.

13. A composition comprising the isolated biologically active compound of claim 1 and a pharmaceutically acceptable carrier.

* * * * *

SEQUENCE LISTING

```
<160> NUMBER OF SEQ ID NOS: 57

<210> SEQ ID NO 1
<211> LENGTH: 705
<212> TYPE: DNA
<213> ORGANISM: Bifidobacterium longum

<400> SEQUENCE: 1
atgttcgtac gaaaaacgtc tatcatgtgc gctatgggga atccaaatga aatcagactg      60
gcgatagtcg ataacgacga cttcgtgctg atgggtttgg cagcgttctt gtcgcgtcat     120
ctgccgaatg ttcggttagc ttggaaggcg aataccggaa ccgatgctct ggaatatgcg     180
acggatcccg caaatgaagc ggacattctg ctggttgaca tgagtctgga ggacatgccc     240
ggagacatgg tgtgccggga aatcagaagt cgtaacagga tgttgccgtt gctggcggtg     300
acatcgttca gtttaattcg ctatgcgcga cgtgctgctg agggtggtgc tcaaggcatt     360
gtgtcaaaag ctgattttcc agcactgtgt aaagcggtca agctcgtcag cgatggtcat     420
actctctgtg ttcgagtagg aggggagact attggattcg aggatgtaga tgctgcatat     480
catcgtctgg ttcgacttcc cgtgaataga atcgaaagat tgtcggaacg ggaaaaatat     540
gccatggaac tatattcaca gtcgtataag cccactcaga ttgcccggat gatggatgtt     600
tcggcaggga cggtgaaaac ctatcttgac cgtgttcaga acaaactcca tcttacttcc     660
agagccgaac tgattgccta ttggtggagg cgggaacgat ggtga                     705

<210> SEQ ID NO 2
<211> LENGTH: 234
<212> TYPE: PRT
<213> ORGANISM: Bifidobacterium longum

<400> SEQUENCE: 2

Met Phe Val Arg Lys Thr Ser Ile Met Cys Ala Met Gly Asn Pro Asn
1               5                   10                  15

Glu Ile Arg Leu Ala Ile Val Asp Asn Asp Asp Phe Val Leu Met Gly
                20                  25                  30

Leu Ala Ala Phe Leu Ser Arg His Leu Pro Asn Val Arg Leu Ala Trp
            35                  40                  45

Lys Ala Asn Thr Gly Thr Asp Ala Leu Glu Tyr Ala Thr Asp Pro Ala
        50                  55                  60

Asn Glu Ala Asp Ile Leu Leu Val Asp Met Ser Leu Glu Asp Met Pro
65                  70                  75                  80

Gly Asp Met Val Cys Arg Glu Ile Arg Ser Arg Asn Arg Met Leu Pro
                85                  90                  95

Leu Leu Ala Val Thr Ser Phe Ser Leu Ile Arg Tyr Ala Arg Arg Ala
```

```
                    100             105             110
Ala Glu Gly Gly Ala Gln Gly Ile Val Ser Lys Ala Asp Phe Pro Ala
            115                 120                 125
Leu Cys Lys Ala Val Lys Leu Val Ser Asp Gly His Thr Leu Cys Val
        130                 135                 140
Arg Val Gly Gly Glu Thr Ile Gly Phe Glu Asp Val Asp Ala Ala Tyr
145                 150                 155                 160
His Arg Leu Val Arg Leu Pro Val Asn Arg Ile Glu Arg Leu Ser Glu
                165                 170                 175
Arg Glu Lys Tyr Ala Met Glu Leu Tyr Ser Gln Ser Tyr Lys Pro Thr
            180                 185                 190
Gln Ile Ala Arg Met Met Asp Val Ser Ala Gly Thr Val Lys Thr Tyr
        195                 200                 205
Leu Asp Arg Val Gln Asn Lys Leu His Leu Thr Ser Arg Ala Glu Leu
210                 215                 220
Ile Ala Tyr Trp Trp Arg Arg Glu Arg Trp
225                 230
```

```
<210> SEQ ID NO 3
<211> LENGTH: 1161
<212> TYPE: DNA
<213> ORGANISM: Bifidobacterium longum

<400> SEQUENCE: 3
atggtgagac gattggcaat ggaaacgata cttgtggttc gcaagaaatg cttgggagta      60
tcgaaaaaaa atcttgttct atcgatagtg gccatgacat gtcttgccgc atgtatcgcc     120
gaatggattc ttgattctcc tgagagtttg aatgatgggt ttattcgcat cgtgtacatg     180
cttgctgtga gtatgttgcc gttatatccg gtaccggcaa catgggggat tatcgtcatc     240
gcatttctga tgaattgat gccttgctta tcgcaatgcg atgagtcatg gggtgttctg      300
gtgtctcttg cgattcaagg ctatgctgct gtttggtgga atggtgtgac ggcaacggtg     360
ctgttgtcta ttagcgcttt gctgaattat gcgatatatc gggagaatag tgaatttggt     420
tcgttcgatg gttccattaa tttggtgtgt ttgctttggt ttgtgtttct tttaggggtt     480
tggctacggc aaaggaacag acttgaaaag aaaaaagagt tagaaaagaa agctgaaatt     540
gttcgatata acttacagct tgctgagggg atgcatgatg ccatgtctgg tgagttgaca     600
cgaatgttgg tcatagtgca ggaaggtatc gatgcatcga aggaagaaga gcttaagcga     660
tggagaaaat tgcagaacgg tatcaataag gtattccaag atctgcattc ggttatgaat     720
tatctatcgg atgatgacca taaacaagat gaggtatttc atgtaagtct tgccgaacat     780
attcaagcta cattgagtga aagtgaccgt cggttgcatg acaaagggtt ttgcggtcat     840
tcatctcttc gcggtgtatc cagcgcaatg ttgaactcgt ggaatcaaat aatcgttaac     900
ctgttgcgtg aaatttacac gaatattgaa cgctatgctg acaaaagtga atattccgtc     960
attgtcacat tttcaaataa tgctgttgat attgttcagg tgaataaatg tcgacaaaag    1020
agtcggcgat gtgtgacttt gggagcaaga aaagggctaa gtatatattc ccgtttgata    1080
tctggacaag gaggattcat cagatatgaa aaagacggcg aagaatggtc tttctattgc    1140
atgttaccgc tactgaccta a                                              1161
```

```
<210> SEQ ID NO 4
<211> LENGTH: 386
<212> TYPE: PRT
<213> ORGANISM: Bifidobacterium longum
```

<400> SEQUENCE: 4

```
Met Val Arg Arg Leu Ala Met Glu Thr Ile Leu Val Val Arg Lys Lys
1               5                   10                  15

Cys Leu Gly Val Ser Lys Lys Asn Leu Val Leu Ser Ile Val Ala Met
            20                  25                  30

Thr Cys Leu Ala Ala Cys Ile Ala Glu Trp Ile Leu Asp Ser Pro Glu
        35                  40                  45

Ser Leu Asn Asp Gly Phe Ile Arg Ile Val Tyr Met Leu Ala Val Ser
    50                  55                  60

Met Leu Pro Leu Tyr Pro Val Pro Ala Thr Trp Gly Ile Ile Val Ile
65                  70                  75                  80

Ala Phe Leu Asn Glu Leu Met Pro Cys Leu Ser Gln Cys Asp Glu Ser
                85                  90                  95

Trp Gly Val Leu Val Ser Leu Ala Ile Gln Gly Tyr Ala Ala Val Trp
            100                 105                 110

Trp Asn Gly Val Thr Ala Thr Val Leu Leu Ser Ile Ser Ala Leu Leu
        115                 120                 125

Asn Tyr Ala Ile Tyr Arg Glu Asn Ser Glu Phe Gly Ser Phe Asp Gly
    130                 135                 140

Ser Ile Asn Leu Val Val Leu Leu Trp Phe Val Phe Leu Leu Gly Val
145                 150                 155                 160

Trp Leu Arg Gln Arg Asn Arg Leu Glu Lys Lys Glu Leu Glu Lys
                165                 170                 175

Lys Ala Glu Ile Val Arg Tyr Asn Leu Gln Leu Ala Glu Gly Met His
            180                 185                 190

Asp Ala Met Ser Gly Glu Leu Thr Arg Met Leu Val Ile Val Gln Glu
        195                 200                 205

Gly Ile Asp Ala Ser Lys Glu Glu Glu Leu Lys Arg Trp Arg Lys Leu
    210                 215                 220

Gln Asn Gly Ile Asn Lys Val Phe Gln Asp Leu His Ser Val Met Asn
225                 230                 235                 240

Tyr Leu Ser Asp Asp His Lys Gln Asp Glu Val Phe His Val Ser
                245                 250                 255

Leu Ala Glu His Ile Gln Ala Thr Leu Ser Glu Ser Asp Arg Arg Leu
            260                 265                 270

His Asp Lys Gly Phe Cys Gly His Ser Ser Leu Arg Gly Val Ser Ser
        275                 280                 285

Ala Met Leu Asn Ser Trp Asn Gln Ile Ile Val Asn Leu Leu Arg Glu
    290                 295                 300

Ile Tyr Thr Asn Ile Glu Arg Tyr Ala Asp Lys Ser Glu Tyr Ser Val
305                 310                 315                 320

Ile Val Thr Phe Ser Asn Asn Ala Val Asp Ile Val Gln Val Asn Lys
                325                 330                 335

Cys Arg Gln Lys Ser Arg Arg Cys Val Thr Leu Gly Ala Arg Lys Gly
            340                 345                 350

Leu Ser Ile Tyr Ser Arg Leu Ile Ser Gly Gln Gly Phe Ile Arg
        355                 360                 365

Tyr Glu Lys Asp Gly Glu Glu Trp Ser Phe Tyr Cys Met Leu Pro Leu
    370                 375                 380

Leu Thr
385
```

<210> SEQ ID NO 5
<211> LENGTH: 201

```
<212> TYPE: DNA
<213> ORGANISM: Bifidobacterium longum

<400> SEQUENCE: 5
atgagcatca atgagaagtc cattgtcggt gaatccttcg aggatctgtc ggcggccgat      60
atggcgatgc tgaccggtcg caacgatgat ggcgtcgcgc cggcgtcgct gtcgttcgcg     120
gtttccgttc tgagcgtgtc tttctcggca tgttcggtaa cggtcgtcac ccgacttgca     180
tcctgtggga actgcaagtg a                                                201

<210> SEQ ID NO 6
<211> LENGTH: 66
<212> TYPE: PRT
<213> ORGANISM: Bifidobacterium longum

<400> SEQUENCE: 6

Met Ser Ile Asn Glu Lys Ser Ile Val Gly Glu Ser Phe Glu Asp Leu
1               5                   10                  15

Ser Ala Ala Asp Met Ala Met Leu Thr Gly Arg Asn Asp Asp Gly Val
            20                  25                  30

Ala Pro Ala Ser Leu Ser Phe Ala Val Ser Val Leu Ser Val Ser Phe
        35                  40                  45

Ser Ala Cys Ser Val Thr Val Val Thr Arg Leu Ala Ser Cys Gly Asn
    50                  55                  60

Cys Lys
65

<210> SEQ ID NO 7
<211> LENGTH: 660
<212> TYPE: DNA
<213> ORGANISM: Bifidobacterium longum

<400> SEQUENCE: 7
atgaaggcga ttctgtttcg tgactgcaag gcatgtttcc agtcattcaa gaactggggt      60
atggttctta tcattatggt cacggcaata ttcgtggaga tggttgccag tggcgcaggc     120
attctagacc catttacttg ggctgtcttt tttggaccgt ttttcatcta ttcgtcatgc     180
tcggtgatgg tctccatcct gtatcaggat ttccgagatg gactgtttga gctctatata     240
cagtctggtc gttcctattg gagctactgc tggtgtaagt gcctgtttcc tgttatcctg     300
acagtgattt ccgtgctttt gaatctggct tttatgcgtg ttttgtcatc aggctttcag     360
ataaccgctg gagcagatga tgcaattggt gctcttatcg tatcagtctt aggaacaatc     420
gtctgttctt gggcgcaat gccgatggtt tatgtctccc ggaacagcga tccgacaatg     480
gcacaactgg ttttggtgtt gattgcgatc ctgctccaat ggcatatac gcttgtggtc     540 gtcaacgtga tgccgctgtg cctgttctcg gtcggttatg tcgtattggt agtggtcgcc     600
atcggtattt caaccggagt attctctcga tatttatca acaccaatat cgagctgtga     660

<210> SEQ ID NO 8
<211> LENGTH: 219
<212> TYPE: PRT
<213> ORGANISM: Bifidobacterium longum

<400> SEQUENCE: 8

Met Lys Ala Ile Leu Phe Arg Asp Cys Lys Ala Cys Phe Gln Ser Phe
1               5                   10                  15

Lys Asn Trp Gly Met Val Leu Ile Ile Met Val Thr Ala Ile Phe Val
            20                  25                  30
```

```
Glu Met Val Ala Ser Gly Ala Gly Ile Leu Asp Pro Phe Thr Trp Ala
         35                  40                  45

Val Phe Phe Gly Pro Phe Phe Ile Tyr Ser Ser Cys Ser Val Met Val
     50                  55                  60

Ser Ile Leu Tyr Gln Asp Phe Arg Asp Gly Leu Phe Glu Leu Tyr Ile
 65                  70                  75                  80

Gln Ser Gly Arg Ser Tyr Trp Ser Tyr Cys Trp Cys Lys Cys Leu Phe
                 85                  90                  95

Pro Val Ile Leu Thr Val Ile Ser Val Leu Leu Asn Leu Ala Phe Met
             100                 105                 110

Arg Val Leu Ser Ser Gly Phe Gln Ile Thr Ala Gly Ala Asp Asp Ala
         115                 120                 125

Ile Gly Ala Leu Ile Val Ser Val Leu Gly Thr Ile Val Cys Ser Leu
     130                 135                 140

Gly Ala Met Pro Met Val Tyr Val Ser Arg Asn Ser Asp Pro Thr Met
145                 150                 155                 160

Ala Gln Leu Val Leu Val Leu Ile Ala Ile Leu Leu Gln Leu Ala Tyr
                 165                 170                 175

Thr Leu Val Val Val Asn Val Met Pro Leu Cys Leu Phe Ser Val Gly
             180                 185                 190

Tyr Val Val Leu Val Val Val Ala Ile Gly Ile Ser Thr Gly Val Phe
         195                 200                 205

Ser Arg Tyr Phe Ile Asn Thr Asn Ile Glu Leu
     210                 215

<210> SEQ ID NO 9
<211> LENGTH: 738
<212> TYPE: DNA
<213> ORGANISM: Bifidobacterium longum

<400> SEQUENCE: 9
atgaccagca tggtggccta tgtcgcttcg cgtaatccgc agtcgcagac gttgcggtcg        60
gttcgtctga tacaggatgc ggtcagtggg aacattgacg cggaatggac gattctgacg       120
ccgaatgaca cgacgatctt gccgtcggat ggtactgcga gcgagttttc caccggtgtc       180
gatcatatcg agctgaacgg actggacgat ccgcccgggg tcaaaaaagc aatcgaacga       240
tgcgattatc tgattctcgg ttcgccgacc tatggccata cgtttccgg cgacatgaag        300 attctgatgg atcgactcac ctattggggg catttgttcc atctggcggg caaaccgggc       360
atggcaatgg tcagcgccac aaccaacggg ttccttgaag tcggcgaact gatgaacgg        420 ttcatggaat cactgggcat catcattgat gaaaccgcat accacaccac ttttacgcca       480
ttcgatgagg caatggccga tcagaccgcc gcggccatcg tgcgggcgct gaacacactg       540
cgggatggcg tcgtgcctga aaccagcgaa aggcaggagc tggcattcca atcctacaag       600
cgtgactacg cccgacgaga cggtagcgat gcagaatcgc ggtattggcg ggaacgcggc       660
atgttcgact gtgcgacgtt ccatgaatac gtcgaaacgc ggcggaagct gccggaatcc       720
gtccacgccg aacggtag                                                     738

<210> SEQ ID NO 10
<211> LENGTH: 245
<212> TYPE: PRT
<213> ORGANISM: Bifidobacterium longum

<400> SEQUENCE: 10

Met Thr Ser Met Val Ala Tyr Val Ala Ser Arg Asn Pro Gln Ser Gln
 1               5                  10                  15
```

```
Thr Leu Arg Ser Val Arg Leu Ile Gln Asp Ala Val Ser Gly Asn Ile
             20                  25                  30

Asp Ala Glu Trp Thr Ile Leu Thr Pro Asn Asp Thr Thr Ile Leu Pro
         35                  40                  45

Ser Asp Gly Thr Ala Ser Glu Phe Ser Thr Gly Val Asp His Ile Glu
     50                  55                  60

Leu Asn Gly Leu Asp Asp Ser Ala Arg Val Lys Lys Ala Ile Glu Arg
 65                  70                  75                  80

Cys Asp Tyr Leu Ile Leu Gly Ser Pro Thr Gly His Asn Val Ser
                 85                  90                  95

Gly Asp Met Lys Ile Leu Met Asp Arg Leu Thr Tyr Trp Gly His Leu
                100                 105                 110

Phe His Leu Ala Gly Lys Pro Gly Met Ala Met Val Ser Ala Thr Thr
            115                 120                 125

Asn Gly Phe Leu Glu Val Gly Glu Leu Met Glu Arg Phe Met Glu Ser
        130                 135                 140

Leu Gly Ile Ile Ile Asp Glu Thr Ala Tyr His Thr Thr Phe Thr Pro
145                 150                 155                 160

Phe Asp Glu Ala Met Ala Asp Gln Thr Ala Ala Ile Val Arg Ala
                165                 170                 175

Leu Asn Thr Leu Arg Asp Gly Val Val Pro Glu Thr Ser Glu Arg Gln
            180                 185                 190

Glu Leu Ala Phe Gln Ser Tyr Lys Arg Asp Tyr Ala Arg Arg Asp Gly
        195                 200                 205

Ser Asp Ala Glu Ser Arg Tyr Trp Arg Glu Arg Gly Met Phe Asp Cys
    210                 215                 220

Ala Thr Phe His Glu Tyr Val Glu Thr Arg Arg Lys Leu Pro Glu Ser
225                 230                 235                 240

Val His Ala Glu Arg
                245

<210> SEQ ID NO 11
<211> LENGTH: 3102
<212> TYPE: DNA
<213> ORGANISM: Bifidobacterium longum

<400> SEQUENCE: 11
atggcggcaa ccgctatgcc ggatgctttg cgacagtatc gggcatcgca tgcggaagac     60
atgctttcgg caacggtgga atggaaaaac cgacggaacc cactgcggga cgaggactat    120
caaggcatcg ccgacgcgct cggcgatgac gcatccgtgg tcgaaaccgt catcgcggat    180
cgggaacgga aactgagcgg ccatgtcgag ccggcatggt ccgttgaact gcagacgatt    240
ctgaaccgtt acgacagcga ggaagagcga gtcgaacgca cggggtatgc caccgccttc    300
gcaccgttcg tcgcgtacgt gaaagcggaa ctgcaagcgc atatgtcggc tgttcattg     360 ccgatgaatg acgagcgcct tatcgaacag tgcctgagcg catacgtcga gcgtctgttg    420
agcatcggat tgaaaaccgt cgtatgggaa ttgcatgtcg cgcgtcaggc cggttcgttg    480
ggcgacggcg atgcgaagcg acaattgcgg cgatatttcg aactgctggc caccgacgaa    540
taccgtggcc atatgtatgc gaaatatccg gtactgcttc gttttgtcac gcagacgaca    600
gtccattaca tcgatttcgt caaggaaatg ctcgaccgcg tatccatgga tcgcgacgag    660
ctcgcctcct tcgcaggcgt cggcgatgat ttcaggttgg aagatatgtc catcgaccgt    720
ggcgacgcgc acgacggtgg aagagccgtg gccatgctca ccatcggcgg acggaaaatc    780
```

```
gtatacaagc cgcgtgacct gcatatccat gagcttttcg ccggattggt gaggcgatgc    840
gaacggacga agggtttcct tccgatgcga gtgtcgacg tgctgacgaa atccggctac     900
gcctatgagg aattcgtgga acacggcacc tgcgaggatg cacgtcaggt ggagcgctat    960
tacaccagat acggtcagct gctcggattg gtatggctcc tgcacggcga cgacatgcac   1020
cacgagaaca tcatcgccag cggggaatat ccgatggtcg tcgatttcga gacgatcgcc   1080
acgaaccatg tgaccatgga catgcccgac ggcaccgatg ccgacatccg cgtatccacg   1140
atattgcggg attcactggc atcctcctgt ctgttgccgg cgaaaacggc gatgtcggcc   1200
gacggtacat ccgtcgacat cagcgccttc gaaaccggtg agcagacgat gcccggcatc   1260
gtcgcgtccc cggtgggatt ggactccgcc gatgcccatt acgagaggaa cgccgtgacg   1320
ttcagcaagg acggctgcgc ggtgacattg atgacgcgcc ttgtggatcc gtatcattac   1380
aagcgacaga ttctccaagg attccgcaat acggtcgccg cggcgatgac catcgacgcg   1440
gatgaatggg atgcgatgct gtccggcgag gatacgaccg tgcgtgtgct ggtgcgcaac   1500
accagcgcct acgcccgatt tgcggatttc atccatcatc cgtcggcgtt gaaggacatg   1560
ctggacgtcg aagccatact ggagaacctg tatgtctacc cattccgtga caagcgcatc   1620
ttcgcaagcg aataccggca gatgctcgcc ggggacatcc ccatgttcac cgcacagctg   1680
acgggacatg atctgcacgc tcccgatgga acgaccattg acggcgtctg cgaacgttcg   1740
gtacgcgaac gggtgcttga caccatcggg catcttgacg aacaggccgc attgcaatcg   1800
cgcattatcc gcaacgcctt gcgcatgaa cccggcatgg aggacgcgca tccgacggct   1860
tcggtgtcgt cggacacgga tgcggagcat tacccaatcg aactcggcac gaggatagcc   1920
gacacggcca tcctccagga aaccgatggc accgtatcat ggcttacagc gaaccgatcc   1980
gacaccatgg ccgcggacaa gaccgtggat gaacggtacg aaccggggc gccgacttcg    2040
ggactctacg acggcatggc cgggacgggc atgttcgccg ccgaactgta tcggcggaca   2100
cacgatgagc gctggcgtga cctgtgcacg cgtatgatgc ggagtctgat gcgccgcaag   2160
gacagaggca ttacgtattc cggcttcact tccggcctgt cgcgaagcta ttgcgcgtta   2220
cgcatggcca atgccggcat cacgtcgccc gaagctcgcc gttgcatgac gcagacggtt   2280
cgtatgctgc cggcatacat cgacgatatg ctgccgaagc tcctgcagcg cgacaatcct   2340
caaccgtcat tccatctgga ttacctgacc ggggcgggca gttcgatcat gctgtatctg   2400
cggctgtacg acgtattcca tgacatgcgc atagtggaac aaaccagccg gctggggaga   2460
accgtcatcc gtgcgtttcc cgaaacccag cggaacgccg acgaatccga tgacatgccg   2520
tatccaaccg gtgccgcgca cggactggaa ggcatggccg tggcgttctg gaagctctac   2580
gcggcgacgg gaatcgcga attcgccgaa ttcgcccgaa tgctttggcg gaaatcggac   2640
gctcgaagaa gcggtgcgaa acaggaggac gccggcaaat ggtgccgtgg aaggtcggc    2700
gtgctctggg cacgcaatga gctggcgcc actgccggcg cggacggcga acgtttcttc    2760
gaggatgaaa acggacgggc gttcccagac aaggcagata tcacggcgtt gcttgggaac   2820
gcggattggg acgacgacgg cgtgtgccat ggacgatgcg gcatgatcga caccctgata   2880
tccatcggca atgccaacgg tgacgaatgg tatcgcatgc aggcacagcg tctgatggac   2940
gacatgatcg cgcaggcccg ttcgtcggga cgtttccggc tgaggcaatc ccgtgaattc   3000
gtggatctgt cgtacttcca agggccggtc ggcgtcgcct acacgatgct tcgtctgaac   3060
gacccgtcca cgccctccat actcgcactg gaaacgcgat ga                     3102
```

<210> SEQ ID NO 12

<211> LENGTH: 1033
<212> TYPE: PRT
<213> ORGANISM: Bifidobacterium longum

<400> SEQUENCE: 12

```
Met Ala Ala Thr Ala Met Pro Asp Ala Leu Arg Gln Tyr Arg Ala Ser
1               5                   10                  15

His Ala Glu Asp Met Leu Ser Ala Thr Val Glu Trp Lys Asn Arg Arg
            20                  25                  30

Asn Pro Leu Arg Asp Glu Asp Tyr Gln Gly Ile Ala Asp Ala Leu Gly
        35                  40                  45

Asp Asp Ala Ser Val Val Glu Thr Val Ile Ala Asp Arg Glu Arg Lys
50                  55                  60

Leu Ser Gly His Val Glu Pro Ala Trp Ser Val Glu Leu Gln Thr Ile
65                  70                  75                  80

Leu Asn Arg Tyr Asp Ser Glu Glu Arg Val Glu Arg Thr Gly Tyr
                85                  90                  95

Ala Thr Ala Phe Ala Pro Phe Val Ala Tyr Val Lys Ala Glu Leu Gln
                100                 105                 110

Ala His Met Ser Ala Cys Ser Leu Pro Met Asn Asp Glu Arg Leu Ile
            115                 120                 125

Glu Gln Cys Leu Ser Ala Tyr Val Glu Arg Leu Leu Ser Ile Gly Leu
        130                 135                 140

Lys Thr Val Val Trp Glu Leu His Val Ala Arg Gln Ala Gly Ser Leu
145                 150                 155                 160

Gly Asp Gly Asp Ala Lys Arg Gln Leu Arg Arg Tyr Phe Glu Leu Leu
                165                 170                 175

Ala Thr Asp Glu Tyr Arg Gly His Met Tyr Ala Lys Tyr Pro Val Leu
            180                 185                 190

Leu Arg Phe Val Thr Gln Thr Thr Val His Tyr Ile Asp Phe Val Lys
        195                 200                 205

Glu Met Leu Asp Arg Val Ser Met Asp Arg Asp Glu Leu Ala Ser Phe
210                 215                 220

Ala Gly Val Gly Asp Asp Phe Arg Leu Glu Asp Met Ser Ile Asp Arg
225                 230                 235                 240

Gly Asp Ala His Asp Gly Gly Arg Ala Val Ala Met Leu Thr Ile Gly
                245                 250                 255

Gly Arg Lys Ile Val Tyr Lys Pro Arg Asp Leu His Ile His Glu Leu
            260                 265                 270

Phe Ala Gly Leu Val Arg Arg Cys Glu Arg Thr Lys Gly Phe Leu Pro
        275                 280                 285

Met Arg Val Ser Asp Val Leu Thr Lys Ser Gly Tyr Ala Tyr Glu Glu
290                 295                 300

Phe Val Glu His Gly Thr Cys Glu Asp Ala Arg Gln Val Glu Arg Tyr
305                 310                 315                 320

Tyr Thr Arg Tyr Gly Gln Leu Leu Gly Leu Val Trp Leu Leu His Gly
                325                 330                 335

Asp Asp Met His His Glu Asn Ile Ile Ala Ser Gly Glu Tyr Pro Met
            340                 345                 350

Val Val Asp Phe Glu Thr Ile Ala Thr Asn His Val Thr Met Asp Met
        355                 360                 365

Pro Asp Gly Thr Asp Ala Asp Ile Arg Val Ser Thr Ile Leu Arg Asp
370                 375                 380

Ser Leu Ala Ser Ser Cys Leu Leu Pro Ala Lys Thr Ala Met Ser Ala
385                 390                 395                 400
```

```
Asp Gly Thr Ser Val Asp Ile Ser Ala Phe Glu Thr Gly Glu Gln Thr
                405                 410                 415
Met Pro Gly Ile Val Ala Ser Pro Val Gly Leu Asp Ser Ala Asp Ala
                420                 425                 430
His Tyr Glu Arg Asn Ala Val Thr Phe Ser Lys Asp Gly Cys Ala Val
                435                 440                 445
Thr Leu Asp Asp Ala Val Val Asp Pro Tyr His Tyr Lys Arg Gln Ile
    450                 455                 460
Leu Gln Gly Phe Arg Asn Thr Val Ala Ala Met Thr Ile Asp Ala
465                 470                 475                 480
Asp Glu Trp Asp Ala Met Leu Ser Gly Glu Asp Thr Thr Val Arg Val
                485                 490                 495
Leu Val Arg Asn Thr Ser Ala Tyr Ala Arg Phe Ala Asp Phe Ile His
                500                 505                 510
His Pro Ser Ala Leu Lys Asp Met Leu Asp Val Glu Ala Ile Leu Glu
            515                 520                 525
Asn Leu Tyr Val Tyr Pro Phe Arg Asp Lys Arg Ile Phe Ala Ser Glu
        530                 535                 540
Tyr Arg Gln Met Leu Ala Gly Asp Ile Pro Met Phe Thr Ala Gln Leu
545                 550                 555                 560
Thr Gly His Asp Leu His Ala Pro Asp Gly Thr Thr Ile Asp Gly Val
                565                 570                 575
Cys Glu Arg Ser Val Arg Glu Arg Val Leu Asp Thr Ile Gly His Leu
                580                 585                 590
Asp Glu Gln Ala Ala Leu Gln Ser Arg Ile Ile Arg Asn Ala Leu Arg
            595                 600                 605
Met Glu Pro Gly Met Glu Asp Ala His Pro Thr Ala Ser Val Ser Ser
        610                 615                 620
Asp Thr Asp Ala Glu His Tyr Pro Ile Glu Leu Gly Thr Arg Ile Ala
625                 630                 635                 640
Asp Thr Ala Ile Leu Gln Glu Thr Asp Gly Thr Val Ser Trp Leu Thr
                645                 650                 655
Ala Asn Arg Ser Asp Thr Met Ala Ala Asp Lys Thr Val Asp Glu Arg
                660                 665                 670
Tyr Glu Pro Gly Ala Pro Thr Ser Gly Leu Tyr Asp Gly Met Ala Gly
            675                 680                 685
Thr Gly Met Phe Ala Ala Glu Leu Tyr Arg Arg Thr His Asp Glu Arg
        690                 695                 700
Trp Arg Asp Leu Cys Thr Arg Met Met Arg Ser Leu Met Arg Arg Lys
705                 710                 715                 720
Asp Arg Gly Ile Thr Tyr Ser Gly Phe Thr Ser Gly Leu Ser Arg Ser
                725                 730                 735
Tyr Cys Ala Leu Arg Met Ala Asn Ala Gly Ile Thr Ser Pro Glu Ala
                740                 745                 750
Arg Arg Cys Met Thr Gln Thr Val Arg Met Leu Pro Ala Tyr Ile Asp
            755                 760                 765
Asp Met Leu Pro Lys Leu Leu Gln Arg Asp Asn Pro Gln Pro Ser Phe
        770                 775                 780
His Leu Asp Tyr Leu Thr Gly Ala Gly Ser Ser Ile Met Leu Tyr Leu
785                 790                 795                 800
Arg Leu Tyr Asp Val Phe His Asp Met Arg Ile Val Glu Gln Thr Ser
                805                 810                 815
Arg Leu Gly Arg Thr Val Ile Arg Ala Phe Pro Glu Thr Gln Arg Asn
```

-continued

```
                   820                 825                 830
Ala Asp Glu Ser Asp Asp Met Pro Tyr Pro Thr Gly Ala Ala His Gly
                835                 840                 845

Leu Glu Gly Met Ala Val Ala Phe Trp Lys Leu Tyr Ala Ala Thr Gly
            850                 855                 860

Asn Arg Glu Phe Ala Glu Phe Ala Arg Met Leu Trp Arg Lys Ser Asp
865                 870                 875                 880

Ala Arg Arg Ser Gly Ala Lys Gln Glu Asp Ala Gly Lys Trp Cys Arg
                885                 890                 895

Gly Lys Val Gly Val Leu Trp Ala Arg Asn Glu Leu Ala Ala Thr Ala
            900                 905                 910

Gly Ala Asp Gly Glu Arg Phe Phe Glu Asp Glu Asn Gly Arg Ala Phe
        915                 920                 925

Pro Asp Lys Ala Asp Ile Thr Ala Leu Leu Gly Asn Ala Asp Trp Asp
    930                 935                 940

Asp Asp Gly Val Cys His Gly Arg Cys Gly Met Ile Asp Thr Leu Ile
945                 950                 955                 960

Ser Ile Gly Asn Ala Asn Gly Asp Glu Trp Tyr Arg Met Gln Ala Gln
                965                 970                 975

Arg Leu Met Asp Asp Met Ile Ala Gln Ala Arg Ser Ser Gly Arg Phe
            980                 985                 990

Arg Leu Arg Gln Ser Arg Glu Phe  Val Asp Leu Ser Tyr  Phe Gln Gly
        995                 1000                 1005

Pro Val  Gly Val Ala Tyr Thr  Met Leu Arg Leu Asn  Asp Pro Ser
    1010                 1015                 1020

Thr Pro  Ser Ile Leu Ala Leu  Glu Thr Arg
    1025                 1030

<210> SEQ ID NO 13
<211> LENGTH: 819
<212> TYPE: DNA
<213> ORGANISM: Bifidobacterium longum

<400> SEQUENCE: 13
atgaccgccg accacatcaa ccacgccgac cgcaccgaca acggcgaaca tgccatcatc      60
gccgtcgaac acgtcacctt cggctacaag aagaaacaga ccgtgttgga ggacatcgac     120
ttcaccgtgc cgcaaggcca gtcgctggcg atcctcggat acaacggcgt cggcaagacc     180
acgctgttca gactcatcgt cggactgctg cgccccgtg aagggcgatg cgtgatcgat      240
aggcgtcggg tgccgtcgat gcgcgacgtg ttccagatga ccgagaacgg caatctcgtc     300
ggcacgatga ccgtgcgtga caacatccac ttccggcaac tgctgttccg gtccggcaag     360
ggaatcgcgg acggcggcca taccgtcgac tcgaaacggc tggaggatga ccgctcgtc     420 cgtgccttcg aattggaggg gcatctcgac aagaaggtgg cggaactctc gaccggtctg     480
cgcaaacggg tcggcatcgt cgccggcatg ctgttcgacc gcatgtcat catgctcgac     540 gagccaagca acgccattga tccgatcacc cgctcgctgc tcgtcgatta cgtcaaccag     600
cttcgcgccg acgagcgcac tttgctcacc gtcacccatg acctcgaata ctgttggaat     660
gtggccgacc ggatcatcat ccttgacgac aaacacctcg tcaaggatat gatgctcgcc     720
gaattcgacg actatgaggc gttcaccaag gcgtccacgc tcgggcgtga ccgcacgcac     780
gtcgacttcg gccttcccgc gcgcggacgg caagcatga                            819

<210> SEQ ID NO 14
<211> LENGTH: 272
```

<212> TYPE: PRT
<213> ORGANISM: Bifidobacterium longum

<400> SEQUENCE: 14

```
Met Thr Ala Asp His Ile Asn His Ala Asp Arg Thr Asp Asn Gly Glu
1               5                   10                  15

His Ala Ile Ile Ala Val Glu His Val Thr Phe Gly Tyr Lys Lys
            20                  25                  30

Gln Thr Val Leu Glu Asp Ile Asp Phe Thr Val Pro Gln Gly Gln Ser
        35                  40                  45

Leu Ala Ile Leu Gly Tyr Asn Gly Val Gly Lys Thr Thr Leu Phe Arg
    50                  55                  60

Leu Ile Val Gly Leu Leu Arg Pro Arg Glu Gly Arg Cys Val Ile Asp
65              70                  75                  80

Arg Arg Arg Val Pro Ser Met Arg Asp Val Phe Gln Met Thr Glu Asn
                85                  90                  95

Gly Asn Leu Val Gly Thr Met Thr Val Arg Asp Asn Ile His Phe Arg
            100                 105                 110

Gln Leu Leu Phe Arg Ser Gly Lys Gly Ile Ala Asp Gly His Thr
        115                 120                 125

Val Asp Ser Lys Arg Leu Glu Asp Glu Pro Leu Val Arg Ala Phe Glu
130                 135                 140

Leu Glu Gly His Leu Asp Lys Lys Val Ala Glu Leu Ser Thr Gly Leu
145                 150                 155                 160

Arg Lys Arg Val Gly Ile Val Ala Gly Met Leu Phe Asp Pro His Val
                165                 170                 175

Ile Met Leu Asp Glu Pro Ser Asn Ala Ile Asp Pro Ile Thr Arg Ser
            180                 185                 190

Leu Leu Val Asp Tyr Val Asn Gln Leu Arg Ala Asp Glu Arg Thr Leu
        195                 200                 205

Leu Thr Val Thr His Asp Leu Glu Tyr Cys Trp Asn Val Ala Asp Arg
    210                 215                 220

Ile Ile Ile Leu Asp Asp Lys His Leu Val Lys Asp Met Met Leu Ala
225                 230                 235                 240

Glu Phe Asp Asp Tyr Glu Ala Phe Thr Lys Ala Ser Thr Leu Gly Arg
                245                 250                 255

Asp Arg Thr His Val Asp Phe Gly Leu Pro Ala Arg Gly Arg Gln Ala
            260                 265                 270
```

<210> SEQ ID NO 15
<211> LENGTH: 2238
<212> TYPE: DNA
<213> ORGANISM: Bifidobacterium longum

<400> SEQUENCE: 15

```
atgagatcat ggcgtcgtca ccgtgtcccg tttatcgaac aaggcgagca cagcgaatgc    60
gggctggccg ccgcagcgat gatcctcgcc gcattcgggc atcccgtgac catggacgag   120
ctgcgccgcc ggtacggcgc tccacgcggc ggactgagcc tcgcgaacat cgtaacggtg   180
ctgtccgact ccggcatccg cgtacgcgcg gtcacgaccc ccagcgccga agcgttgaaa   240
accgtcatga cgccatgcat cctgcattgg gacgacaacc atttcgtcgt gctcgaccat   300
tacgcatacg gccgattccg catcgctgac ccggcgaacg ggcgccatgc ctatacgccc   360
ggcgaactcg cggcccactg ttctggcgcg gtgctgattc gcaaccgac  aaacgacggc   420 tgcgcaacca ttcccatacg gcctcgcagc ggaaccgtct ccatcctgac cgggttcctc   480
```

```
cgccggaaca tgcccgccat cggtctgagc ctgctgttct cgctcgtcgt ccagggactg    540
acattgatcg tgcccgcagg caccggctat atggtcgacc atgggtcgct cgccgcccaa    600
agcggtttcc cgccgttggt cgcgacgatg ctgcttgcct cgctgctggt ctactatgcg    660
gtcggcgcgt tgaacaccgt gatgctcacc cgcgtgcagg tgcgattcgg acgatacctg    720
tcccgccgat acatgaccgg cgtgctcgat cgggagttcc cgttcttcgt gaaccgttcc    780
ggtggtgacc tgatctaccg cgcgaacctg gtcatggtcg tcgaacagat cgtgaccggc    840
agtctgccgt cgacggtcgt gtcgatggtg ttcctcgtgg tctacctgat catgatgatc    900
gcctattcag tgccattgac gatgctgacc ctgacggtgt gcgcggcggt gctcgtcgta    960
tccgtcattt attccctgcg caacaggacg ctggtcgagc gtgcgaccgt cgcgcaggct   1020
gacgtgcaac gcgccttcat cgaaaccttc tccggcatcg aaactgtcaa aagcctcaat   1080
ttggaaagcc actgctacga ccgctggtca gcgcgtctgg agcgcagct cgactaccag    1140
actcggcaag gcggcttc ggcattgctg tcaagcctgt cctcggcgct ggtgttcgtg     1200
ttgccgctat gcgtggtcgc cttcggcatg accttcgtgg acgcggcac gctcgcactg    1260
ggtgccgtcg tcggattcat gtcattggcg tccgcattcg tcacgccatt ctccggcatc    1320
gtcggcgtca tcagccagat catggcgttc gccacctata tgcgcaagat tgcgagatg    1380
attcccgccg tgaaggcgg cggtgcgtcg cttgaatgcg acgaaccggg tggcgaaccg    1440
ggtgacgtcg gactgggtga cggcggacgg tccgcatgtg gtgggccgag tggtgacgaa   1500
tcgggtgatg gcatactcga acggttcat gccaccggcg tgggatactc gtacacggcg    1560
ttcgacgctc ccgttctctc cgatgtcgat tgcgacatcc gcaaaggcga caagatcgcc   1620
atcgtcggcc ccactggctc gggcaaaagc acgctgctga aactgctcgc cggactcatc   1680
gaacccgtct gtggcacggt gaccatcaac ggcggcggat gccggattta cgacgcggac   1740
agccgatgga aggccggcag gctggcgtat gtgcatcagg aatccacggt gttcaacgaa   1800
accttgcgcg acaatatcac gctgcaccgt ccgtggctga cggatgacga catcgtcagg   1860
gcgtgcgagg ttgccggcat caacgagggg atgatggatc cggtcgtcgg cttggacgcc   1920
atggtcagtg aacgcggcat gaacctgtcc ggcggccaac ggcagaaggt cgccatcgcg   1980
cgtgcggtcg tcggaagacc ggacttccta cttatggacg aacccaccag tgctctggac   2040
aacgataccg agcgacatgt catgacggcg ttgctcgact ccgacaatgc gtgcatcgtc   2100
gtggcgcaca gactcgcatc gattcgggat ttcgaccgca tccatgtcat ggatcatggg   2160
cagatcgtcg aatccggtac gcatgacgaa ctgctgcagg ccggcggatt gtattcgcgg   2220
ctgtaccggc aggagtga                                                 2238
```

<210> SEQ ID NO 16
<211> LENGTH: 745
<212> TYPE: PRT
<213> ORGANISM: Bifidobacterium longum

<400> SEQUENCE: 16

Met Arg Ser Trp Arg Arg His Arg Val Pro Phe Ile Glu Gln Gly Glu
1               5                   10                  15

His Ser Glu Cys Gly Leu Ala Ala Ala Ala Met Ile Leu Ala Ala Phe
            20                  25                  30

Gly His Pro Val Thr Met Asp Glu Leu Arg Arg Arg Tyr Gly Ala Pro
        35                  40                  45

Arg Gly Gly Leu Ser Leu Ala Asn Ile Val Thr Val Leu Ser Asp Ser
    50                  55                  60

-continued

```
Gly Ile Arg Val Arg Ala Val Thr Thr Pro Ser Ala Glu Ala Leu Lys
 65                  70                  75                  80

Thr Val Met Thr Pro Cys Ile Leu His Trp Asp Asp Asn His Phe Val
                 85                  90                  95

Val Leu Asp His Tyr Ala Tyr Gly Arg Phe Arg Ile Ala Asp Pro Ala
            100                 105                 110

Asn Gly Arg His Ala Tyr Thr Pro Gly Glu Leu Ala Ala His Cys Ser
        115                 120                 125

Gly Ala Val Leu Ile Pro Gln Pro Thr Asn Asp Gly Cys Ala Thr Ile
130                 135                 140

Pro Ile Arg Pro Arg Ser Gly Thr Val Ser Ile Leu Thr Gly Phe Leu
145                 150                 155                 160

Arg Arg Asn Met Pro Ala Ile Gly Leu Ser Leu Leu Phe Ser Leu Val
                165                 170                 175

Val Gln Gly Leu Thr Leu Ile Val Pro Ala Gly Thr Gly Tyr Met Val
            180                 185                 190

Asp His Gly Ser Leu Ala Ala Gln Ser Gly Phe Pro Pro Leu Val Ala
        195                 200                 205

Thr Met Leu Leu Ala Ser Leu Leu Val Tyr Tyr Ala Val Gly Ala Leu
210                 215                 220

Asn Thr Val Met Leu Thr Arg Val Gln Val Arg Phe Gly Arg Tyr Leu
225                 230                 235                 240

Ser Arg Arg Tyr Met Thr Gly Val Leu Asp Arg Glu Phe Pro Phe Phe
                245                 250                 255

Val Asn Arg Ser Gly Gly Asp Leu Ile Tyr Arg Ala Asn Leu Val Met
            260                 265                 270

Val Val Glu Gln Ile Val Thr Gly Ser Leu Pro Ser Thr Val Val Ser
        275                 280                 285

Met Val Phe Leu Val Val Tyr Leu Ile Met Met Ile Ala Tyr Ser Val
290                 295                 300

Pro Leu Thr Met Leu Thr Leu Thr Val Cys Ala Ala Val Leu Val Val
305                 310                 315                 320

Ser Val Ile Tyr Ser Leu Arg Asn Arg Thr Leu Val Glu Arg Ala Thr
                325                 330                 335

Val Ala Gln Ala Asp Val Gln Arg Ala Phe Ile Glu Thr Phe Ser Gly
            340                 345                 350

Ile Glu Thr Val Lys Ser Leu Asn Leu Glu Ser His Cys Tyr Asp Arg
        355                 360                 365

Trp Ser Ala Arg Leu Gly Ala Gln Leu Asp Tyr Gln Thr Arg Gln Gly
370                 375                 380

Arg Leu Ser Ala Leu Leu Ser Ser Leu Ser Ser Ala Leu Val Phe Val
385                 390                 395                 400

Leu Pro Leu Cys Val Val Ala Phe Gly Met Thr Phe Val Gly Arg Gly
                405                 410                 415

Thr Leu Ala Leu Gly Ala Val Gly Phe Met Ser Leu Ala Ser Ala
            420                 425                 430

Phe Val Thr Pro Phe Ser Gly Ile Val Gly Val Ile Ser Gln Ile Met
        435                 440                 445

Ala Phe Ala Thr Tyr Met Arg Lys Ile Cys Glu Met Ile Pro Ala Gly
450                 455                 460

Glu Gly Gly Gly Ala Ser Leu Glu Cys Asp Glu Pro Gly Gly Glu Pro
465                 470                 475                 480

Gly Asp Val Gly Leu Gly Asp Gly Gly Arg Ser Ala Cys Gly Gly Pro
                485                 490                 495
```

```
Ser Gly Asp Glu Ser Gly Asp Gly Ile Leu Glu Arg Leu His Ala Thr
            500                 505                 510
Gly Val Gly Tyr Ser Tyr Thr Ala Phe Asp Ala Pro Val Leu Ser Asp
        515                 520                 525
Val Asp Cys Asp Ile Arg Lys Gly Asp Lys Ile Ala Ile Val Gly Pro
    530                 535                 540
Thr Gly Ser Gly Lys Ser Thr Leu Leu Lys Leu Leu Ala Gly Leu Ile
545                 550                 555                 560
Glu Pro Val Cys Gly Thr Val Thr Ile Asn Gly Gly Cys Arg Ile
                565                 570                 575
Tyr Asp Ala Asp Ser Arg Trp Lys Ala Gly Arg Leu Ala Tyr Val His
            580                 585                 590
Gln Glu Ser Thr Val Phe Asn Glu Thr Leu Arg Asp Asn Ile Thr Leu
        595                 600                 605
His Arg Pro Trp Leu Thr Asp Asp Ile Val Arg Ala Cys Glu Val
    610                 615                 620
Ala Gly Ile Asn Glu Gly Met Met Asp Pro Val Val Gly Leu Asp Ala
625                 630                 635                 640
Met Val Ser Glu Arg Gly Met Asn Leu Ser Gly Gly Gln Arg Gln Lys
                645                 650                 655
Val Ala Ile Ala Arg Ala Val Val Gly Arg Pro Asp Phe Leu Leu Met
            660                 665                 670
Asp Glu Pro Thr Ser Ala Leu Asp Asn Asp Thr Glu Arg His Val Met
        675                 680                 685
Thr Ala Leu Leu Asp Ser Asp Asn Ala Cys Ile Val Val Ala His Arg
    690                 695                 700
Leu Ala Ser Ile Arg Asp Phe Asp Arg Ile His Val Met Asp His Gly
705                 710                 715                 720
Gln Ile Val Glu Ser Gly Thr His Asp Glu Leu Leu Gln Ala Gly Gly
                725                 730                 735
Leu Tyr Ser Arg Leu Tyr Arg Gln Glu
            740                 745

<210> SEQ ID NO 17
<211> LENGTH: 102
<212> TYPE: DNA
<213> ORGANISM: Bifidobacterium longum

<400> SEQUENCE: 17
ccggcgtcgc tgtcgttcgc ggtttccgtt ctgagcgtgt ctttctcggc atgttcggta      60
acggtcgtca cccgacttgc atcctgtggg aactgcaagt ga                       102

<210> SEQ ID NO 18
<211> LENGTH: 33
<212> TYPE: PRT
<213> ORGANISM: Bifidobacterium longum

<400> SEQUENCE: 18

Pro Ala Ser Leu Ser Phe Ala Val Ser Val Leu Ser Val Ser Phe Ser
1               5                   10                  15
Ala Cys Ser Val Thr Val Val Thr Arg Leu Ala Ser Cys Gly Asn Cys
            20                  25                  30
Lys

<210> SEQ ID NO 19
<211> LENGTH: 33
```

```
<212> TYPE: PRT
<213> ORGANISM: artificial
<220> FEATURE:
<223> OTHER INFORMATION: intermediate polypeptide resulting from
      dehydration
<220> FEATURE:
<221> NAME/KEY: MISC_FEATURE
<222> LOCATION: (3)..(3)
<223> OTHER INFORMATION: X is serine or didehydroalanine
<220> FEATURE:
<221> NAME/KEY: MISC_FEATURE
<222> LOCATION: (5)..(5)
<223> OTHER INFORMATION: X is serine or didehydroalanine
<220> FEATURE:
<221> NAME/KEY: MISC_FEATURE
<222> LOCATION: (9)..(9)
<223> OTHER INFORMATION: X is serine or didehydroalanine
<220> FEATURE:
<221> NAME/KEY: MISC_FEATURE
<222> LOCATION: (12)..(12)
<223> OTHER INFORMATION: X is serine or didehydroalanine
<220> FEATURE:
<221> NAME/KEY: MISC_FEATURE
<222> LOCATION: (14)..(14)
<223> OTHER INFORMATION: X is serine or didehydroalanine
<220> FEATURE:
<221> NAME/KEY: MISC_FEATURE
<222> LOCATION: (16)..(16)
<223> OTHER INFORMATION: X is serine or didehydroalanine
<220> FEATURE:
<221> NAME/KEY: MISC_FEATURE
<222> LOCATION: (19)..(19)
<223> OTHER INFORMATION: X is serine or didehydroalanine
<220> FEATURE:
<221> NAME/KEY: MISC_FEATURE
<222> LOCATION: (21)..(21)
<223> OTHER INFORMATION: X is threonine or didehydrobutyrine
<220> FEATURE:
<221> NAME/KEY: MISC_FEATURE
<222> LOCATION: (24)..(24)
<223> OTHER INFORMATION: X is threonine or didehydrobutyrine
<220> FEATURE:
<221> NAME/KEY: MISC_FEATURE
<222> LOCATION: (28)..(28)
<223> OTHER INFORMATION: X is serine or didehydroalanine

<400> SEQUENCE: 19

Pro Ala Xaa Leu Xaa Phe Ala Val Xaa Val Leu Xaa Val Xaa Phe Xaa
1               5                   10                  15

Ala Cys Xaa Val Xaa Val Val Xaa Arg Leu Ala Xaa Cys Gly Asn Cys
                20                  25                  30

Lys

<210> SEQ ID NO 20
<211> LENGTH: 33
<212> TYPE: PRT
<213> ORGANISM: artificial
<220> FEATURE:
<223> OTHER INFORMATION: intermediate polypeptide resulting from
      dehydration
<220> FEATURE:
<221> NAME/KEY: MISC_FEATURE
<222> LOCATION: (14)..(14)
<223> OTHER INFORMATION: X is didehydroalanine
<220> FEATURE:
<221> NAME/KEY: MISC_FEATURE
<222> LOCATION: (16)..(16)
<223> OTHER INFORMATION: X is didehydroalanine
<220> FEATURE:
<221> NAME/KEY: MISC_FEATURE
<222> LOCATION: (21)..(21)
<223> OTHER INFORMATION: X is didehydrobutyrine
<220> FEATURE:
<221> NAME/KEY: MISC_FEATURE
<222> LOCATION: (24)..(24)
<223> OTHER INFORMATION: X is didehydrobutyrine
```

```
<220> FEATURE:
<221> NAME/KEY: MISC_FEATURE
<222> LOCATION: (28)..(28)
<223> OTHER INFORMATION: X is didehydroalanine

<400> SEQUENCE: 20

Pro Ala Ser Leu Ser Phe Ala Val Ser Val Leu Ser Val Xaa Phe Xaa
1               5                   10                  15

Ala Cys Ser Val Xaa Val Val Xaa Arg Leu Ala Xaa Cys Gly Asn Cys
            20                  25                  30

Lys

<210> SEQ ID NO 21
<211> LENGTH: 33
<212> TYPE: PRT
<213> ORGANISM: artificial
<220> FEATURE:
<223> OTHER INFORMATION: polypeptide resulting from dehydration
<220> FEATURE:
<221> NAME/KEY: MISC_FEATURE
<222> LOCATION: (3)..(3)
<223> OTHER INFORMATION: X is serine, didehydroalanine, or alanine
<220> FEATURE:
<221> NAME/KEY: MISC_FEATURE
<222> LOCATION: (5)..(5)
<223> OTHER INFORMATION: X is serine, didehydroalanine, or alanine
<220> FEATURE:
<221> NAME/KEY: MISC_FEATURE
<222> LOCATION: (9)..(9)
<223> OTHER INFORMATION: X is serine, didehydroalanine, or alanine
<220> FEATURE:
<221> NAME/KEY: MISC_FEATURE
<222> LOCATION: (12)..(12)
<223> OTHER INFORMATION: X is serine, didehydroalanine, or alanine
<220> FEATURE:
<221> NAME/KEY: MISC_FEATURE
<222> LOCATION: (14)..(14)
<223> OTHER INFORMATION: X is serine, didehydroalanine, or alanine
<220> FEATURE:
<221> NAME/KEY: MISC_FEATURE
<222> LOCATION: (16)..(16)
<223> OTHER INFORMATION: X is serine, didehydroalanine, or alanine
<220> FEATURE:
<221> NAME/KEY: MISC_FEATURE
<222> LOCATION: (18)..(18)
<223> OTHER INFORMATION: X is cysteine or alanine
<220> FEATURE:
<221> NAME/KEY: MISC_FEATURE
<222> LOCATION: (19)..(19)
<223> OTHER INFORMATION: X is serine, didehydroalanine, or alanine
<220> FEATURE:
<221> NAME/KEY: MISC_FEATURE
<222> LOCATION: (21)..(21)
<223> OTHER INFORMATION: X is threonine, didehydobutyrine, or
     2-aminobutyric acid
<220> FEATURE:
<221> NAME/KEY: MISC_FEATURE
<222> LOCATION: (24)..(24)
<223> OTHER INFORMATION: X is threonine, didehydobutyrine, or
     2-aminobutyric acid
<220> FEATURE:
<221> NAME/KEY: MISC_FEATURE
<222> LOCATION: (28)..(28)
<223> OTHER INFORMATION: X is serine, didehydroalanine, or alanine
<220> FEATURE:
<221> NAME/KEY: MISC_FEATURE
<222> LOCATION: (29)..(29)
<223> OTHER INFORMATION: X is cysteine or alanine
<220> FEATURE:
<221> NAME/KEY: MISC_FEATURE
<222> LOCATION: (32)..(32)
<223> OTHER INFORMATION: X is cysteine or alanine

<400> SEQUENCE: 21

Pro Ala Xaa Leu Xaa Phe Ala Val Xaa Val Leu Xaa Val Xaa Phe Xaa
```

```
                1               5              10              15
Ala Xaa Xaa Val Xaa Val Val Xaa Arg Leu Ala Xaa Xaa Gly Asn Xaa
                20              25              30
Lys

<210> SEQ ID NO 22
<211> LENGTH: 33
<212> TYPE: PRT
<213> ORGANISM: artificial
<220> FEATURE:
<223> OTHER INFORMATION: polypeptide resulting from dehydration
<220> FEATURE:
<221> NAME/KEY: THIOETH
<222> LOCATION: (14)..(18)
<220> FEATURE:
<221> NAME/KEY: MISC_FEATURE
<222> LOCATION: (16)..(16)
<223> OTHER INFORMATION: X is didehydroalanine
<220> FEATURE:
<221> NAME/KEY: MISC_FEATURE
<222> LOCATION: (21)..(21)
<223> OTHER INFORMATION: X is didehydrobutyrine
<220> FEATURE:
<221> NAME/KEY: MOD_RES
<222> LOCATION: (24)..(24)
<223> OTHER INFORMATION: X is Abu
<220> FEATURE:
<221> NAME/KEY: THIOETH
<222> LOCATION: (24)..(29)
<220> FEATURE:
<221> NAME/KEY: THIOETH
<222> LOCATION: (28)..(32)

<400> SEQUENCE: 22

Pro Ala Ser Leu Ser Phe Ala Val Ser Val Leu Ser Val Ala Phe Xaa
1               5              10              15

Ala Ala Ser Val Xaa Val Val Xaa Arg Leu Ala Ala Ala Gly Asn Ala
                20              25              30
Lys

<210> SEQ ID NO 23
<211> LENGTH: 12219
<212> TYPE: DNA
<213> ORGANISM: Bifidobacterium longum

<400> SEQUENCE: 23
ctactccaac ttgacaaaac acagcggtag cgcctgcgcg gttcggcgcg cctgcggccg      60
gccttgcgcc gcggcggggc cggcgatgta gtatccgccc gtccacgggc cgtcttcag     120 ccgtttcggc cggtacggcc ggtaggactc gttctcgttg acgggaacc acgtgtcgcg     180 tttgatctcc ctgccgaccg tcgaggcgtt gcggccgagc atcagaccga tcctgcggat     240
gctggtgccg ttgccgatct cgatctggat gacctggcgt tcctcttccg acaggtgcga     300
acatgcttct cccataggtg caacatccct tcggactggt tatccggaca atctccaatc     360
caacgggtgt tgcactttca attagacaac ggggcgggca tgttcgtacg aaaaacgtct     420
atcatgtgcg ctatggggaa tccaaatgaa atcagactgg cgatagtcga taacgacgac     480
ttcgtgctga tgggtttggc agcgttcttg tcgcgtcatc tgccgaatgt tcggttagct     540
tggaaggcga ataccggaac cgatgctctg gaatatgcga cggatcccgc aaatgaagcg     600
gacattctgc tggttgacat gagtctggag gacatgcccg agacatggt gtgccgggaa     660 atcagaagtc gtaacaggat gttgccgttg ctggcggtga catcgttcag tttaattcgc     720
tatgcgcgac gtgctgctga gggtggtgct caaggcattg tgtcaaaagc tgatttcca     780
```

-continued

```
gcactgtgta aagcggtcaa gctcgtcagc gatggtcata ctctctgtgt tcgagtagga    840
ggggagacta ttggattcga ggatgtagat gctgcatatc atcgtctggt tcgacttccc    900
gtgaatagaa tcgaaagatt gtcggaacgg gaaaaatatg ccatggaact atattcacag    960
tcgtataagc ccactcagat tgcccggatg atggatgttt cggcagggac ggtgaaaacc   1020
tatcttgacc gtgttcagaa caaactccat cttacttcca gagccgaact gattgcctat   1080
tggtggaggc gggaacgatg gtgagacgat tggcaatgga aacgatactt gtggttcgca   1140
agaaatgctt gggagtatcg aaaaaaaatc ttgttctatc gatagtggcc atgacatgtc   1200
ttgccgcatg tatcgccgaa tggattcttg attctcctga gagtttgaat gatgggttta   1260
ttcgcatcgt gtacatgctt gctgtgagta tgttgccgtt atatccggta ccggcaacat   1320
ggggattat cgtcatcgca tttctgaatg aattgatgcc ttgcttatcg caatgcgatg   1380
agtcatgggg tgttctggtg tctcttgcga ttcaaggcta tgctgctgtt tggtggaatg   1440
gtgtgacgga acggtgctg ttgtctatta gcgctttgct gaattatgcg atatatcggg   1500
agaatagtga atttggttcg ttcgatggtt ccattaattt ggtggtgttg ctttggtttg   1560
tgtttctttt aggggtttgg ctacggcaaa ggaacagact tgaaaagaaa aaagagttag   1620
aaaagaaagc tgaaattgtt cgatataact tacagcttgc tgaggggatg catgatgcca   1680
tgtctggtga gttgacacga atgttggtca tagtgcagga aggtatcgat gcatcgaagg   1740
aagaagagct taagcgatgg agaaaattgc agaacggtat caataaggta ttccaagatc   1800
tgcattcggt tatgaattat ctatcggatg atgaccataa acaagatgag gtatttcatg   1860
taagtcttgc cgaacatatt caagctacat tgagtgaaag tgaccgtcgg ttgcatgaca   1920
aagggttttg cggtcattca tctcttcgcg gtgtatccag cgcaatgttg aactcgtgga   1980
atcaaataat cgttaacctg ttgcgtgaaa tttacacgaa tattgaacgc tatgctgaca   2040
aaagtgaata ttccgtcatt gtcacatttt caaataatgc tgttgatatt gttcaggtga   2100
ataaatgtcg acaaaagagt cggcgatgtg tgactttggg agcaagaaaa gggctaagta   2160
tatattcccg tttgatatct ggacaaggag gattcatcag atatgaaaaa gacggcgaag   2220
aatggtcttt ctattgcatg ttaccgctac tgacctaatt tctgatatgg cataatggaa   2280
accatacagg gcatagtgaa tatgttgata tttcttcctc cgttgaactg ttgcttggag   2340
tgctggctga cgctccgaat gtcaaaccaa gtaccgtaag tattaaaagc ggtgttctca   2400
tgagggttcc tttgcgtcgg ggtgtgtcaa tgatcattgc acaacatgga ttcatataaa   2460
agtccttgtc ccctaatggc atacaagtca ttgcgaagcg ggagaaagcg cgtcatgctt   2520
acagtagctc ttcgcctgaa gggcaggaat taggtaagga ggcctatatg agcatcaatg   2580
agaagtccat tgtcggtgaa tccttcgagg atctgtcggc ggccgatatg gcgatgctga   2640
ccggtcgcaa cgatgatggc gtcgcgccgg cgtcgctgtc gttcgcggtt ccgttctga   2700
gcgtgtcttt ctcggcatgt tcggtaacgg tcgtcacccg acttgcatcc tgtgggaact   2760
gcaagtgaac gttgctttac atgggtcagg tatggattgc gtaaaacatc cgacccatac   2820
ctgacacttg ttatcgttaa ggggaagtgg catgaaggcg attctgtttc gtgactgcaa   2880
ggcatgtttc cagtcattca agaactgggg tatggttctt atcattatgg tcacggcaat   2940
attcgtggag atggttgcca gtggcgcagg cattctagac ccatttactt gggctgtctt   3000
ttttggaccg ttttttcatct attcgtcatg ctcggtgatg gtctccatcc tgtatcagga   3060
tttccgagat ggactgtttg agctctatat acagtctggt cgttcctatt ggagctactg   3120
ctggtgtaag tgcctgtttc ctgttatcct gacagtgatt tccgtgcttt tgaatctggc   3180
```

```
tttatgcgt gttttgtcat caggctttca gataaccgct ggagcagatg atgcaattgg   3240
tgctcttatc gtatcagtct taggaacaat cgtctgttct ttgggcgcaa tgccgatggt   3300
ttatgtctcc cggaacagcg atccgacaat ggcacaactg gttttggtgt tgattgcgat   3360
cctgctccaa ttggcatata cgcttgtggt cgtcaacgtg atgccgctgt gcctgttctc   3420
ggtcggttat gtcgtattgg tagtggtcgc catcggtatt tcaaccggag tattctctcg   3480
atattttatc aacaccaata tcgagctgtg acatctactg gattcgaagc ttttggaaag   3540
gtggatttcc atgaccagca tggtggccta tgtcgcttcg cgtaatccgc agtcgcagac   3600
gttgcggtcg gttcgtctga tacaggatgc ggtcagtggg aacattgacg cggaatggac   3660
gattctgacg ccgaatgaca cgacgatctt gccgtcggat ggtactgcga gcgagttttc   3720
caccggtgtc gatcatatcg agctgaacgg actggacgat tccgcccggg tcaaaaaagc   3780
aatcgaacga tgcgattatc tgattctcgg ttcgccgacc tatggccata acgtttccgg   3840
cgacatgaag attctgatgg atcgactcac ctattggggg catttgttcc atctggcggg   3900
caaaccgggc atggcaatgg tcagcgccac aaccaacggg ttccttgaag tcggcgaact   3960
gatgaacgtt catggaat cactgggcat catcattgat gaaaccgcat accacaccac   4020
ttttacgcca ttcgatgagg caatggccga tcagaccgcc gcggccatcg tgcgggcgct   4080
gaacacactg cgggatggcg tcgtgcctga aaccagcgaa aggcaggagc tggcattcca   4140
atcctacaag cgtgactacg cccgacgaga cggtagcgat gcagaatcgc ggtattggcg   4200
ggaacgcggc atgttcgact gtgcgacgtt ccatgaatac gtcgaaacgc ggcggaagct   4260
gccggaatcc gtccacgccg aacggtaggg ggactttcca tgaacggtaa cgttggaacg   4320
acctgggcgg cttctgccac gacccttgag gaacggtgca tggcggcaac cgctatgccg   4380
gatgctttgc gacagtatcg ggcatcgcat gcggaagaca tgctttcggc aacggtggaa   4440
tggaaaaacc gacggaaccc actgcgggac gaggactatc aaggcatcgc cgacgcgctc   4500
ggcgatgacg catccgtggt cgaaaccgtc atcgcggatc gggaacggaa actgagcggc   4560
catgtcgagc cggcatggtc cgttgaactg cagacgattc tgaaccgtta cgacagcgag   4620
gaagagcgag tcgaacgcac ggggtatgcc accgccttcg caccgttcgt cgcgtacgtg   4680
aaagcggaac tgcaagcgca tatgtcggcc tgttcattgc cgatgaatga cgagcgcctt   4740
atcgaacagt gcctgagcgc atacgtcgag cgtctgttga gcatcggatt gaaaaccgtc   4800
gtatgggaat tgcatgtcgc gcgtcaggcc ggttcgttgg gcgacggcga tgcgaagcga   4860
caattgcggc gatatttcga actgctgcc accgacgaat accgtggcca tatgtatgcg   4920
aaatatccgg tactgcttcg ttttgtcacg cagacgacag tccattacat cgatttcgtc   4980
aaggaaatgc tcgaccgcgt atccatggat cgcgacgagc tcgcctcctt cgcaggcgtc   5040
ggcgatgatt tcaggttgga agatatgtcc atcgaccgtg gcgacgcgca cgacggtgga   5100
agagccgtgg ccatgctcac catcggcgga cggaaaatcg tatacaagcc gcgtgacctg   5160
catatccatg agcttttcgc cggattggtg aggcgatgcg aacggacgaa gggtttcctt   5220
ccgatgcgag tgtcggacgt gctgacgaaa tccggctacg cctatgagga attcgtggaa   5280
cacggcacct gcgaggatgc acgtcaggtg gagcgctatt acaccagata cggtcagctg   5340
ctcggattgg tatggctcct gcacggcgac gacatgcacc acgagaacat catcgccagc   5400
ggggaatatc cgatggtcgt cgatttcgag acgatcgcca cgaaccatgt gaccatggac   5460
atgcccgacg gcaccgatgc cgacatccgc gtatccacga tattgcggga ttcactggca   5520
tcctcctgtc tgttgccggc gaaaacggcg atgtcggccg acggtacatc cgtcgacatc   5580
```

-continued

```
agcgccttcg aaaccggtga gcagacgatg cccggcatcg tcgcgtcccc ggtgggattg    5640
gactccgccg atgcccatta cgagaggaac gccgtgacgt tcagcaagga cggctgcgcg    5700
gtgacattgg atgacgccgt tgtggatccg tatcattaca agcgacagat tctccaagga    5760
ttccgcaata cggtcgccgc ggcgatgacc atcgacgcgg atgaatggga tgcgatgctg    5820
tccggcgagg atacgaccgt gcgtgtgctg gtgcgcaaca ccagcgccta cgcccgattt    5880
gcggatttca tccatcatcc gtcggcgttg aaggacatgc tggacgtcga agccatactg    5940
gagaacctgt atgtctaccc attccgtgac aagcgcatct tcgcaagcga ataccggcag    6000
atgctcgccg gggacatccc catgttcacc gcacagctga cgggacatga tctgcacgct    6060
cccgatggaa cgaccattga cggcgtctgc gaacgttcgg tacgcgaacg ggtgcttgac    6120
accatcgggc atcttgacga acaggccgca ttgcaatcgc gcattatccg caacgccttg    6180
cgcatggaac ccggcatgga ggacgcgcat ccgacggctt cggtgtcgtc ggacacggat    6240
gcggagcatt acccaatcga actcggcacg aggatagccg acacggccat cctccaggaa    6300
accgatggca ccgtatcatg gcttacagcg aaccgatccg acaccatggc cgcggacaag    6360
accgtggatg aacggtacga accggggggcg ccgacttcgg gactctacga cggcatggcc    6420
gggacgggca tgttcgccgc cgaactgtat cggcggacac acgatgagcg ctggcgtgac    6480
ctgtgcacgc gtatgatgcg gagtctgatg cgccgcaagg acagaggcat tacgtattcc    6540
ggcttcactt ccggcctgtc gcgaagctat tgcgcgttac gcatggccaa tgccggcatc    6600
acgtcgcccg aagctcgccg ttgcatgacg cagacggttc gtatgctgcc ggcatacatc    6660
gacgatatgc tgccgaagct cctgcagcgc gacaatcctc aaccgtcatt ccatctggat    6720
tacctgaccg gggcgggcag ttcgatcatg ctgtatctgc ggctgtacga cgtattccat    6780
gacatgcgca tagtggaaca aaccagccgg ctggggagaa ccgtcatccg tgcgtttccc    6840
gaaacccagc ggaacgccga cgaatccgat gacatgccgt atccaaccgg tgccgcgcac    6900
ggactggaag gcatggccgt ggcgttctgg aagctctacg cggcgacggg gaatcgcgaa    6960
ttcgccgaat tcgcccgaat gctttggcgg aaatcggacg ctcgaagaag cggtgcgaaa    7020
caggaggacg ccggcaaatg gtgccgtggg aaggtcggcg tgctctgggc acgcaatgag    7080
ctggcggcca ctgccggcgc ggacggcgaa cgtttcttcg aggatgaaaa cggacgggcg    7140
ttcccagaca aggcagatat cacggcgttg cttgggaacg cggattggga cgacgacggc    7200
gtgtgccatg gacgatgcgg catgatcgac accctgatat ccatcggcaa tgccaacggt    7260
gacgaatggt atcgcatgca ggcacagcgt ctgatggacg acatgatcgc gcaggcccgt    7320
tcgtcgggac gtttccggct gaggcaatcc cgtgaattcg tggatctgtc gtacttccaa    7380
gggccggtcg gcgtcgccta cacgatgctt cgtctgaacg acccgtccac gccctccata    7440
ctcgcactgg aaacgcgatg acggacatga cggatacgaa cacaaccgaa tcgacgacaa    7500
ggaaagacaa tatgaccgcc gaccacatca accacgccga ccgcaccgac aacggcgaac    7560
atgccatcat cgccgtcgaa cacgtcacct tcggctacaa gaagaaacag accgtgttgg    7620
aggacatcga cttcaccgtg ccgcaaggcc agtcgctggc gatcctcgga tacaacggcg    7680
tcggcaagac cacgctgttc agactcatcg tcggactgct gcgcccccgt gaagggcgat    7740
gcgtgatcga taggcgtcgg gtgccgtcga tgcgcgacgt gttccagatg accgagaacg    7800
gcaatctcgt cggcacgatg accgtgcgtg acaacatcca cttccggcaa ctgctgttcc    7860
ggtccggcaa gggaatcgcg gacggcggcc ataccgtcga ctcgaaacgg ctggaggatg    7920
agccgctcgt ccgtgccttc gaattggagg ggcatctcga caagaaggtg gcggaactct    7980
```

```
cgaccggtct gcgcaaacgg gtcggcatcg tcgccggcat gctgttcgac ccgcatgtca   8040
tcatgctcga cgagccaagc aacgccattg atccgatcac ccgctcgctg ctcgtcgatt   8100
acgtcaacca gcttcgcgcc gacgagcgca ctttgctcac cgtcacccat gacctcgaat   8160
actgttggaa tgtggccgac cggatcatca tccttgacga caaacacctc gtcaaggata   8220
tgatgctcgc cgaattcgac gactatgagg cgttcaccaa ggcgtccacg ctcgggcgtg   8280
accgcacgca cgtcgacttc ggccttcccg cgcgcggacg gcaagcatga gatcatggcg   8340
tcgtcaccgt gtcccgttta tcgaacaagg cgagcacagc gaatgcgggc tggccgccgc   8400
agcgatgatc ctcgccgcat tcgggcatcc cgtgaccatg gacgagctgc gccgccggta   8460
cggcgctcca cgcggcggac tgagcctcgc gaacatcgta acggtgctgt ccgactccgg   8520
catccgcgta cgcgcggtca cgaccccag cgccgaagcg ttgaaaaccg tcatgacgcc   8580
atgcatcctg cattgggacg acaaccattt cgtcgtgctc gaccattacg catacggccg   8640
attccgcatc gctgacccgg cgaacgggcg ccatgcctat acgcccggcg aactcgcggc   8700
ccactgttct ggcgcggtgc tgattccgca accgacaaac gacggctgcg caaccattcc   8760
catacggcct cgcagcggaa ccgtctccat cctgaccggg ttcctccgcc ggaacatgcc   8820
cgccatcggt ctgagcctgc tgttctcgct cgtcgtccag ggactgacat tgatcgtgcc   8880
cgcaggcacc ggctatatgg tcgaccatgg gtcgctcgcc gcccaaagcg gtttcccgcc   8940
gttggtcgcg acgatgctgc ttgcctcgct gctggtctac tatgcggtcg gcgcgttgaa   9000
caccgtgatg ctcacccgcg tgcaggtgcg attcggacga tacctgtccc gccgatacat   9060
gaccggcgtg ctcgatcggg agttcccgtt cttcgtgaac cgttccggtg gtgacctgat   9120
ctaccgcgcg aacctggtca tggtcgtcga acagatcgtg accggcagtc tgccgtcgac   9180
ggtcgtgtcg atggtgttcc tcgtggtcta cctgatcatg atgatcgcct attcagtgcc   9240
attgacgatg ctgaccctga cggtgtgcgc ggcggtgctc gtcgtatccg tcatttattc   9300
cctgcgcaac aggacgctgg tcgagcgtgc gaccgtcgcg caggctgacg tgcaacgcgc   9360
cttcatcgaa accttctccg gcatcgaaac tgtcaaaagc ctcaatttgg aaagccactg   9420
ctacgaccgc tggtcagcgc gtctgggagc gcagctcgac taccagactc ggcaagggcg   9480
gctttcggca ttgctgtcaa gcctgtcctc ggcgctggtg ttcgtgttgc cgctatgcgt   9540
ggtcgccttc ggcatgacct tcgtgggacg cggcacgctc gcactgggtg ccgtcgtcgg   9600
attcatgtca ttggcgtccg cattcgtcac gccattctcc ggcatcgtcg cgtcatcag   9660 ccagatcatg gcgttcgcca cctatatgcg caagatttgc gagatgattc cgccggtga   9720 aggcggcggt gcgtcgcttg aatgcgacga accgggtggc gaaccgggtg acgtcggact   9780
gggtgacggc ggacggtccg catgtggtgg gccgagtggt gacgaatcgg gtgatggcat   9840
actcgaacgg ttgcatgcca ccggcgtggg atactcgtac acggcgttcg acgctcccgt   9900
tctctccgat gtcgattgcg acatccgcaa aggcgacaag atcgccatcg tcggcccac   9960 tggctcgggc aaaagcacgc tgctgaaact gctcgccgga ctcatcgaac ccgtctgtgg  10020
cacggtgacc atcaacggcg gcggatgccg gatttacgac gcggacagcc gatggaaggc  10080
cggcaggctg gcgtatgtgc atcaggaatc cacggtgttc aacgaaacct gcgcgacaa  10140 tatcacgctg caccgtccgt ggctgacgga tgacgacatc gtcagggcgt gcgaggttgc  10200
cggcatcaac gagggggatga tggatccggt cgtcggcttg gacgccatgg tcagtgaacg  10260
cggcatgaac ctgtccggcg gccaacggca gaaggtcgcc atcgcgcgtg cggtcgtcgg  10320
aagaccggac ttcctactta tggacgaacc caccagtgct ctggacaacg ataccgagcg  10380
```

```
acatgtcatg acggcgttgc tcgactccga caatgcgtgc atcgtcgtgg cgcacagact   10440
cgcatcgatt cgggatttcg accgcatcca tgtcatggat catgggcaga tcgtcgaatc   10500
cggtacgcat gacgaactgc tgcaggccgg cggattgtat tcgcggctgt accggcagga   10560
gtgagtgtcc ccttacaccc ttacgccttt aaacccttac cctttacacc ttatcccttc   10620
caccctcggc tcatgaggcc ccccggattc aatttgtaag cgcaacgctt gtgttcgggc   10680
tggctgcctt cgattgtagc ttggcgatct cctcgtccca tacctcgttg ggcgttttgt   10740
agccgaggag cttcatgggg gtgtcgttga tctccccgac gatcgcgtcg aggtcctcct   10800
gggccaagtc ctcgaacccg gttcctttgg gcagatagcg gcggatcctg ccgttcctgt   10860
tctcgttgct gccacgctgc caggaactgt acgggtcggc gaagtacgtg agcatgccca   10920
gcgcctcgtc caccagcatg tgcaggctcg cctccgtgcc gttgtcccac gtgcggtcga   10980
cgcgcgcggc cggcgggatg tccttgaaga tctcgtattc ggccctggcc gtggcggacg   11040
cgctcttgtc gtcgacgagc cgggcgaaca gcctgcggct cctgcgctcc acctgcgtgt   11100
tcatgcagcg cctcgacggc gcggcgccga ccaccgtgtc cgactgtatt tcgtcaagtc   11160
ggtgtttcgt gtttagtcat gtatttttttt cgggtttagg cagttgcatg cattttcctt   11220
atttttccgg ttgcgcggag gtgttcctgc cgaacatgag ggcctcactg acgcggcggc   11280
tctggccggt gaactcgagg agccgcccgt ggtgcacgat gcggtcgatg atcgctgcgg   11340
cgagtttgtc gtccgcgaag accgtgcccc atttactgaa ctcgatgttc gtggtgaata   11400
tgatgctccg tctttcgtag ctgcccgcga tgatctggta gagcaggcgc gccccgtcga   11460
tgtcgaaggg tacgtagccg aactcgtcca gtatgatcag gtcggcacgg ccgatgtccc   11520
ggagcatcgt ctcgagcgtg ccgtcgcgtt tggccttgcc cagctggagg acgagctcgg   11580
cggtctgatg gaaccgcacg cccagcccca tgtcgatcgc cttcatgccc agcccgatcg   11640
cgagatgtgt ctttccgcgc ccggtcttgc cgtagaacac caggtcctgc gcgcgcggga   11700
tgaaaccgag ccctaggagc tcatcgagca tgtagccgtc ggggagcctg acgttcgtga   11760
agtcgtagcc gtcgagaccc ttgacgacgg ggaaccgggc gcggcgcagg agcctgtcgt   11820
gcttcgcgcg ttccctgttc gccagttccg tgtcgagcag gcggtggacg gcgtcgacct   11880
ggcggggcgt ggcccagccg gcgaattcgt cgatgctcgc cttggagatg aacagcttgc   11940
gggccttctc gtagagccct tcgtccgtct tcgtgttcat cgcccgcctt cctgcacgcc   12000
gacgtccgcg gtgaacgcga tgtcgtattc actcagatcc ggcctgtcat cgtcgtattc   12060 gataccgcc acgccctcgg cgagcctggc cgcgagcagt gtgacaccgg cgcggtccgc   12120
cccgccggtc gattcgagga tggaaagcat cgcctcgacc gcgttcgccc acccggattc   12180
cctgtcaacg cgtttgaggg tctgcagcgc ctcgttgcg                          12219
```

<210> SEQ ID NO 24
<211> LENGTH: 20
<212> TYPE: DNA
<213> ORGANISM: Bifidobacterium longum

<400> SEQUENCE: 24

```
ttaaaccgac atcggtttaa                                                  20
```

<210> SEQ ID NO 25
<211> LENGTH: 96
<212> TYPE: DNA
<213> ORGANISM: Bifidobacterium longum

<400> SEQUENCE: 25

```
gattaagccg ggtttgttgt taagccgggg aacggttcgg ggtcttggtg gctggccgtg    60
tcccatgtgg tttcccggct taacgttccg ggttat                              96
```

```
<210> SEQ ID NO 26
<211> LENGTH: 19
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 26
gaaatcccga aanacnacc                                                 19

<210> SEQ ID NO 27
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(16)
<223> OTHER INFORMATION: n is a, c, g, or t

<400> SEQUENCE: 27
gttgccgatg ttytgncc                                                  18

<210> SEQ ID NO 28
<211> LENGTH: 19
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(16)
<223> OTHER INFORMATION: n is a, c, g, or t

<400> SEQUENCE: 28
gtatgtgatg agcggnagy                                                 19

<210> SEQ ID NO 29
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(16)
<223> OTHER INFORMATION: n is a, c, g, or t

<400> SEQUENCE: 29
accaacggat ttytgngg                                                  18

<210> SEQ ID NO 30
<211> LENGTH: 18
<212> TYPE: DNA
<213> ORGANISM: artificial
<220> FEATURE:
<223> OTHER INFORMATION: primer
<220> FEATURE:
```

```
<221> NAME/KEY: misc_feature
<222> LOCATION: (18)..(18)
<223> OTHER INFORMATION: n is a, c, g, or t

<400> SEQUENCE: 30
aagttcaccg atgaracn                                                    18

<210> SEQ ID NO 31
<211> LENGTH: 19
<212> TYPE: DNA
<213> ORGANISM: artificial
<220> FEATURE:
<223> OTHER INFORMATION: primer

<400> SEQUENCE: 31
gtaacgcaac gartaytcc                                                   19

<210> SEQ ID NO 32
<211> LENGTH: 21
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (20)..(20)
<223> OTHER INFORMATION: n is a, c, g, or t

<400> SEQUENCE: 32
tccccaacta cattathgtn g                                                21

<210> SEQ ID NO 33
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 33
tcaacaccat cngcnacc                                                    18

<210> SEQ ID NO 34
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 34
attggcttat tgctnacn                                                    18

<210> SEQ ID NO 35
<211> LENGTH: 22
<212> TYPE: DNA
```

```
<213> ORGANISM: artificial
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t

<400> SEQUENCE: 35
gactgcttca actgnagdat cc                                              22

<210> SEQ ID NO 36
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t

<400> SEQUENCE: 36
acagtcccaa tacagtaara cn                                              22

<210> SEQ ID NO 37
<211> LENGTH: 21
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 37
ctcaaagaaa ttagangcnc c                                               21

<210> SEQ ID NO 38
<211> LENGTH: 19
<212> TYPE: DNA
<213> ORGANISM: artificial
<220> FEATURE:
<223> OTHER INFORMATION: primer

<400> SEQUENCE: 38
atgaaggcga ttctgtttc                                                  19

<210> SEQ ID NO 39
<211> LENGTH: 19
<212> TYPE: DNA
<213> ORGANISM: artificial
<220> FEATURE:
<223> OTHER INFORMATION: primer

<400> SEQUENCE: 39
tcacagctcg atattggtg                                                  19

<210> SEQ ID NO 40
<211> LENGTH: 18
<212> TYPE: DNA
<213> ORGANISM: artificial
<220> FEATURE:
<223> OTHER INFORMATION: primer
```

```
<400> SEQUENCE: 40
cagcwgccgc ggtaatwc                                                18

<210> SEQ ID NO 41
<211> LENGTH: 15
<212> TYPE: DNA
<213> ORGANISM: artificial
<220> FEATURE:
<223> OTHER INFORMATION: primer

<400> SEQUENCE: 41
acgggcggtg tgtrc                                                   15

<210> SEQ ID NO 42
<211> LENGTH: 18
<212> TYPE: DNA
<213> ORGANISM: artificial
<220> FEATURE:
<223> OTHER INFORMATION: primer

<400> SEQUENCE: 42
atccaacgag caagaacc                                                18

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43
gtgaaatcac cactaccacc                                              20

<210> SEQ ID NO 44
<211> LENGTH: 20
<212> TYPE: DNA
<213> ORGANISM: artificial
<220> FEATURE:
<223> OTHER INFORMATION: primer

<400> SEQUENCE: 44
cacatcttgg aactgcttgg                                              20

<210> SEQ ID NO 45
<211> LENGTH: 19
<212> TYPE: DNA
<213> ORGANISM: artificial
<220> FEATURE:
<223> OTHER INFORMATION: primer

<400> SEQUENCE: 45
cgtacaccga tgaatgacc                                               19

<210> SEQ ID NO 46
<211> LENGTH: 19
<212> TYPE: DNA
<213> ORGANISM: artificial
<220> FEATURE:
<223> OTHER INFORMATION: primer

<400> SEQUENCE: 46
gttcttcgtc acctccacc                                               19

<210> SEQ ID NO 47
<211> LENGTH: 20
<212> TYPE: DNA
```

```
<213> ORGANISM: artificial
<220> FEATURE:
<223> OTHER INFORMATION: primer

<400> SEQUENCE: 47
agtaatgtcc cgaatcctcc                                              20

<210> SEQ ID NO 48
<211> LENGTH: 19
<212> TYPE: DNA
<213> ORGANISM: artificial
<220> FEATURE:
<223> OTHER INFORMATION: primer

<400> SEQUENCE: 48
gacaaaccca agaccctcc                                               19

<210> SEQ ID NO 49
<211> LENGTH: 20
<212> TYPE: DNA
<213> ORGANISM: artificial
<220> FEATURE:
<223> OTHER INFORMATION: primer

<400> SEQUENCE: 49
cgtgcatatc cccattatcc                                              20

<210> SEQ ID NO 50
<211> LENGTH: 20
<212> TYPE: DNA
<213> ORGANISM: artificial
<220> FEATURE:
<223> OTHER INFORMATION: primer

<400> SEQUENCE: 50
gccccaagta cagtctatcc                                              20

<210> SEQ ID NO 51
<211> LENGTH: 19
<212> TYPE: DNA
<213> ORGANISM: artificial
<220> FEATURE:
<223> OTHER INFORMATION: primer

<400> SEQUENCE: 51
cagaacgaac aatcgaacc                                               19

<210> SEQ ID NO 52
<211> LENGTH: 21
<212> TYPE: DNA
<213> ORGANISM: artificial
<220> FEATURE:
<223> OTHER INFORMATION: primer

<400> SEQUENCE: 52
tgtcacagca gattctacag g                                            21

<210> SEQ ID NO 53
<211> LENGTH: 18
<212> TYPE: DNA
<213> ORGANISM: artificial
<220> FEATURE:
<223> OTHER INFORMATION: primer

<400> SEQUENCE: 53
cagcaattcg ttcacagc                                                18
```

```
<210> SEQ ID NO 54
<211> LENGTH: 19
<212> TYPE: DNA
<213> ORGANISM: artificial
<220> FEATURE:
<223> OTHER INFORMATION: primer

<400> SEQUENCE: 54
cgagatcgtc gagctttcc                                                  19

<210> SEQ ID NO 55
<211> LENGTH: 19
<212> TYPE: DNA
<213> ORGANISM: artificial
<220> FEATURE:
<223> OTHER INFORMATION: primer

<400> SEQUENCE: 55
atcagggcga tgaggttgg                                                  19

<210> SEQ ID NO 56
<211> LENGTH: 19
<212> TYPE: DNA
<213> ORGANISM: artificial
<220> FEATURE:
<223> OTHER INFORMATION: primer

<400> SEQUENCE: 56
gagcatcaat gagaagtcc                                                  19

<210> SEQ ID NO 57
<211> LENGTH: 18
<212> TYPE: DNA
<213> ORGANISM: artificial
<220> FEATURE:
<223> OTHER INFORMATION: primer

<400> SEQUENCE: 57
gcaatcaaca ccaaaacc                                                   18
```